(12) United States Patent
Larocca et al.

(10) Patent No.: US 7,148,202 B2
(45) Date of Patent: *Dec. 12, 2006

(54) RECEPTOR-MEDIATED GENE DELIVERY USING BACTERIOPHAGE VECTORS

(75) Inventors: David Larocca, Encinitas, CA (US); Andrew Baird, London (GB); Wendy Johnson, Encinitas, CA (US)

(73) Assignee: Selective Genetics, Inc., San Diego, CA (US)

( * ) Notice: Subject to any disclaimer, the term of this patent is extended or adjusted under 35 U.S.C. 154(b) by 147 days.

This patent is subject to a terminal disclaimer.

(21) Appl. No.: 10/171,407

(22) Filed: Jun. 12, 2002

(65) Prior Publication Data

US 2003/0082143 A1 May 1, 2003

Related U.S. Application Data

(63) Continuation-in-part of application No. PCT/US98/17950, filed on Aug. 28, 1998, now Pat. No. 6,448,083, which is a continuation-in-part of application No. 08/920,396, filed on Aug. 29, 1997, now Pat. No. 6,054,312.

(51) Int. Cl.
*A61K 31/711* (2006.01)
*C12N 15/00* (2006.01)
*C12N 15/11* (2006.01)

(52) U.S. Cl. .................. 514/44; 435/320.1; 536/24.5
(58) Field of Classification Search ................ 435/455, 435/320.1; 530/350, 387.1
See application file for complete search history.

(56) References Cited

U.S. PATENT DOCUMENTS

| | | | | |
|---|---|---|---|---|
| 5,474,935 | A | 12/1995 | Chatterjee et al. | 435/320.1 |
| 5,773,289 | A | 6/1998 | Samulski et al. | 435/320.1 |
| 5,843,742 | A | 12/1998 | Natsoulis et al. | 435/172.3 |
| 5,871,982 | A | 2/1999 | Wilson et al. | 435/172.3 |
| 6,054,312 | A | 4/2000 | Larocca et al. | 435/320.1 |
| 6,323,004 | B1 | 11/2001 | Kang | 435/69.1 |
| 6,448,083 | B1 * | 9/2002 | Larocca et al. | 435/456 |

FOREIGN PATENT DOCUMENTS

| | | |
|---|---|---|
| GB | 2268942 A | 1/1994 |
| WO | WO 92/20791 | 11/1992 |
| WO | WO 95/34648 | 12/1995 |
| WO | WO 96/21007 | 7/1996 |
| WO | WO 97/00271 | 1/1997 |
| WO | WO 97/06435 | 2/1997 |
| WO | WO 98/05344 | 2/1998 |
| WO | WO 98/39482 | 9/1998 |

OTHER PUBLICATIONS

"New Living Colors GFP Mammalian Vectors." Clontechniques, http://www.clontech.com/archive/JUL96UPD/EGFP.html. [Accessed Jun. 20, 2000].

Barry et al., "Toward cell-targeting gene therapy vectors: Selection of cell-binding peptides from random peptide-presenting phage libraries," *Nature Medicine* 2(3):299-305, 1996.

de Kruif et al., "Rapid selection of cell subpopulation-specific human monoclonal antibodies from a synthetic phage antibody library," *Proc. Natl. Acad. Sci. USA* 92:3938-3942, 1995.

Dunn, I. S., "Mammalian cell binding and transfection mediated by surface-modified bacteriophage lambda," *Biochimie* 78:856-861, 1996.

Fisher et al., "Transduction with Recombinant Adeno-Associated Virus for Gene Therapy Is Limited by Leading-Strand Synthesis," *Journal of Virology* 70(1): 520-532, 1996.

Georges et al., "Synthesis of a human insulin gene VII. Synthesis of preproinsulin-like human DNA, its cloning and expression in M13 bacteriophage," *Gene* 27:201-211, 1984.

Goldman et al, "Targeted Gene Delivery to Kaposi'Sarcoma Cells Via the Fibroblast Growth Factor Receptor," *Cancer Research* 57:1447-1451, 1997.

Greenstein et al. Vectors derived from filamentous phages. In Current Protocols in Molecular Biology (Ausubel et al. Eds.) pp. 1.14.4-1.14.5 John Wiley & Sons, New York, 1993.

Hart et al., "Cell Binding and Internalization by Filamentous Phage Displaying a Cyclic Arg-Gly-Asp-containing Peptide," *Journal of Biological Chemistry* 269:12468-12474, 1994.

Hogrete et al., "Cloning in a bacteriophage lambda vector for the display of binding proteins on filamentous phage," *Gene* 137:85091, 1993.

Hoogenboom et al., "Multi-subunit proteins on the surface of filamentous phage: methodologies for displaying antibody (Fab) Heavy and light chains," *Nucleic Acids Research* 19(15): 4133-4137, 1991.

Ishiura et al., "Phage Particle-Medicated Gene Transfer to Cultured Mammalian Cells," *Molecular and Cellular Biology* 2(6):607-616, 1982.

Jespers et al., "λZLG6: A Phage λ Vector for High-Efficiency Cloning and Surface Expression of cDNA Libraries on Filamentous Phage," *Gene* 173(2):179-181, 1996.

Jespers et al., "Surface Experssion and Ligand-Based Selection of cDNAs Fused to Filamentous Phage Gene VI," *Bio/Technology* 13: 378-382, 1995.

Larocca et al., "Gene Transfer to Mammalian Cells Using Genetically Targeted Filamentous Bacteriophage," *FASEB J.* 13:727-734, 1999.

Larocca et al., "Targeted Gene Delivery to Mammalian Cells Via Fibroblast Growth Factor (FGF-2) Display Phage," *Cancer Gene Theraphy* 5(6):S10/PD-31, 1998.

Larocca et al., "Targeting Bacteriophage to Mammalian Cell Surface Receptors for Gene Delivery," *Hum. Gene Ther.* 9:2393-2399, 1998.

(Continued)

*Primary Examiner*—John S. Brusca
(74) *Attorney, Agent, or Firm*—Seed IP Law Group PLLC

(57) ABSTRACT

Filamentous phage particles displaying a ligand on their surface are used to deliver a therapeutic gene to a cell. The ligand is a fusion protein with a phage capsid protein, covalently conjugated to phage particles, or complexed with modified phage particles.

12 Claims, 21 Drawing Sheets

OTHER PUBLICATIONS

Maruyama et al., ".lambda.foo: A .lambda. phage vector for the expression of foreign proteins," *Proc. Natl. Acad. Sci. USA* 91:8273-8277, 1994.

Okayama and Berg, "Bacteriophage Lambda Vector for Transducing a cDNA Clone Library into Mammalian Cells," *Molecular and Cellular Biology* 5(5):1136-1142, 1985.

Orkin et al. Report and recommentations of the panel to assess the NIH investment in research on gene therapy. pp. 1-41, 1995, www.nih.gov/news/panelrep.html.

Pasqualini and Ruoslahti, "Organ targeting *in vivo* using phage display peptide libraries," *Nature* 380:364-366, 1996.

Pasqualini et al., "αv Integrins as receptors for tumor targeting by circulating ligands," *Nature Biotechnology* 15542:546, 1997.

Rubenstein et al., "Subtractive hybridization system using single-stranded phagemids with directional inserts," *Nucleic Acids Research* 18(16): 4833-4842, 1990.

Russell, S. J., "Peptide-displaying phages for targeted gene delivery?" *Nature Medicine* 2(3):276-277, 1996.

Sawyer et al., "Methodology for Selection of Human Antibodies to Membrane Proteins from a Phage-Display Library," *Journal of Immunological Methods* 204:193-203, 1997.

Soderlind et al., "Phage Display Technology in Antibody Engineering: Design of Phagemid Vectors and in vitroMaturation Systems," *Immunological Reviews* 130: 109-124, 1992.

Souriau et al., "A Simple Luciferase Assay for Signal Transduction Activity Detection of Epidermal Growth Factor Displayed on Phage," *Nucleic Acids Research* 25(8):1585-1590, 1997.

Voiculescu, "Aspecte ale interrelatiilor bacteriofagi-celule cucariote," *Bacteriologia, Virusologia, Parazitologia, Epidemiologia XXII*(3): 141-148, 1977 (+ English Translation).

Wu et al., "Development of a Novel Drug-Delivery System Using Bacteriophage MS2 Capsids," *Biochemical Society Transactions* 24:413S, 1996.

Yokoyama-Kobayashi and Kato, "Recombinant f1 Phage Particles Can Transfect Monkey COS-7 Cells by DEAE Dextran Method," *Biochemical and Biophysical Research Communications* 192(2):935-939, 1993.

Yokoyama-Kobayashi and Kato, "Recombinant f1 Phage-Mediated Transfection of Mammalian Cells Using Lipopolyamine Technique," *Analytical Biochemistry* 223:130-134, 1994.

\* cited by examiner

```
                      SEQUENCE LISTING

<160> NUMBER OF SEQ ID NOS: 3

<210> SEQ ID NO 1
<211> LENGTH: 23
<212> TYPE: PRT
<213> ORGANISM: Artificial Sequence
<220> FEATURE:
<223> OTHER INFORMATION: Endosome-disruptive peptides

<400> SEQUENCE: 1

Gly Leu Phe Glu Ala Ile Glu Gly Phe Ile Glu Asn Gly Trp Glu Gly
 1               5                  10                  15

Met Ile Asp Gly Gly Gly Cys
            20

<210> SEQ ID NO 2
<211> LENGTH: 24
<212> TYPE: PRT
<213> ORGANISM: Artificial Sequence
<220> FEATURE:
<223> OTHER INFORMATION: Endosome-disruptive peptide

<400> SEQUENCE: 2

Gly Leu Phe Glu Ala Ile Glu Gly Phe Ile Glu Asn Gly Trp Glu Gly
 1               5                  10                  15

Met Ile Asp Gly Trp Tyr Gly Cys
            20

<210> SEQ ID NO 3
<211> LENGTH: 4
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 2, 3
<223> OTHER INFORMATION: Xaa = Any Amino Acid
<220> FEATURE:
<221> NAME/KEY: VARIANT
<222> LOCATION: 4
<223> OTHER INFORMATION: Xaa = Lys or Arg

<400> SEQUENCE: 3

Lys Xaa Xaa Xaa
 1
```

RECEPTOR-MEDIATED GENE DELIVERY USING BACTERIOPHAGE VECTORS

CROSS-REFERENCE TO RELATED APPLICATIONS

This application is a continuation-in-part application of PCT Application No. PCT/US98/17950, filed Aug. 28, 1998, which claims the benefit of priority from U.S. application Ser. No. 08/920,396, filed Aug. 29, 1997, now U.S. Pat. No. 6,054,312.

TECHNICAL FIELD

The present invention relates generally to gene delivery, and more specifically, to the preparation and use of bacteriophages modified with ligands to deliver genes that alter the phenotype, function, gene expression, or viability of a cell in a therapeutic manner.

BACKGROUND OF THE INVENTION

In one approach, gene therapy attempts to target cells in a specific manner. Thus, a therapeutic gene is linked in some fashion to a targeting molecule in order to deliver the gene into a target cell or tissue. Current methods typically involve linking up a targeting molecule such as a ligand or antibody that recognizes an internalizing receptor to either naked DNA or a mammalian cell virus (e.g. adenovirus) containing the desired gene. When naked DNA is used it must be condensed in vitro into a compact geometry for entry into cells. A polycation such as polylysine is commonly used to neutralize the charge on DNA and condense it into toroid structures. This condensation process, however, is poorly understood and difficult to control, thus, making the manufacturing of homogeneous gene therapy drugs extremely challenging.

Mammalian viruses, in contrast, can package DNA into uniform particles, but, because of their complexity, they are difficult to genetically manipulate and the manufacture of viral particles for gene delivery is costly and time-consuming. Bacteriophages offer an attractive alternative as a natural method for condensing and packaging therapeutic DNA and, because of their simplicity, are relatively easy to genetically manipulate (and retain function). Moreover, because bacteriophage are extremely simplistic entities, large-scale production of phage-based gene-delivery vectors would be easier and less expensive than the production of mammalian viral vectors, for example.

Bacteriophage, such as lambda and filamentous phage, have occasionally been used in efforts to transfer DNA into mammalian cells. In general, transduction of lambda was found to be a relatively rare event and the expression of the reporter gene was weak. In an effort to enhance transduction efficiency, methods utilizing calcium phosphate or liposomes (which do not specifically target a cell surface receptor) were used in conjunction with lambda. Gene transfer has been observed via lambda phage using calcium phosphate co-precipitation (Ishiura, M. et al, *Mol. Cell. Biol.*, 2: 607–616, 1982), or via filamentous phage using DEAE-dextran or lipopolyamine (Yokoyama-Kobayashi and Kato, *Biochem. Biophys. Res. Comm.* 192: 935–939, 1993; Yokoyama-Kobayashi and Kato, *Anal. Biochem.* 223: 130–134, 1994). However, these methods of introducing DNA into mammalian cells are not practical for gene therapy applications, as the transfection efficiency tends to be low, non-specific, and transfection is not only cumbersome, but is promiscuous regarding cell type. More reliable means of targeting vectors to specific cells (or receptors) and of guaranteeing a therapeutically useful degree of gene delivery and expression are thus required, if bacteriophage are to be shaped into vectors useful in therapeutic applications.

Attempts to target filamentous phage to cells using a fusion of a cyclic RGD peptide and a phage coat protein or a peptide-coat protein fusion have met with limited success. Although the phage are targeted and internalized, phage gene expression was neither expected nor reported (Hart et al., *J. Biol. Chem.* 269: 12468–12474, 1994; Barry et al., *Nature Med.* 2: 299–305, 1996). While it is generally understood that the RGD peptide sequence used by Hart et al. binds to integrins, Hart describes RGD mediated uptake of phage as a process similar to phagocytic uptake of bacteria via the protein invasin (an RGD protein); adenoviruses use RGD-integrin binding in conjunction with ligand-receptor binding for internalization. It is therefore not clear that RGD-integrin binding facilitates the entry of the peptide or fusion protein via a receptor mediated-endosomal mechanism, a mechanism which has been shown to yield superior results.

Thus, for gene delivery applications, methods and therapeutic agents that are simple to perform and manufacture, efficient, and target to specific cells would be very beneficial. Similarly, vectors that deliver therapeutically useful quantities of genes of interest via numerous routes of administration—including oral means—would be desirable. In response to these long-felt needs, the present invention provides compositions and methods for gene delivery using bacteriophage that express a ligand and carry a gene of interest, as well as provide other related advantages.

SUMMARY OF THE INVENTION

In one aspect, the invention provides a method of gene delivery, comprising: contacting a mammalian cell with filamentous phage particles presenting a ligand on their surfaces, wherein a vector within the phage encodes a gene product under control of a promoter.

In related aspects, the invention provides methods of treating tumors, smooth muscle cell diseases, or angiogenic diseases, comprising administering a pharmaceutical composition to a patient comprising a physiologically acceptable buffer and filamentous phage particles presenting a ligand on their surfaces, wherein the phage genome encodes a therapeutic gene product under control of a promoter.

In a preferred embodiment, the ligand is a polypeptide reactive with FGF receptor, and in a most preferred embodiment the ligand is FGF-2. In other embodiments, the ligand is an antibody and preferably a single-chain antibody.

The ligand may be genetically fused with a phage capsid protein or chemically conjugated to form a covalent attachment or by sandwich method. Generally, the capsid protein for gene fusion is gene III or gene VIII.

In a preferred embodiment, an endosomal escape moiety is incorporated into the ligand or displayed by other means on the surface of the phages. The ligand or phage may also further comprise a nuclear localization sequence.

In another preferred embodiment, the phage genome is a phagemid.

In preferred embodiments, the therapeutic gene product is selected from the group consisting of protein, ribozyme, and antisense oligonucleotide, and in other embodiments the therapeutic gene product is a cytotoxic agent (e.g., ribosome inactivating protein, such as saporin) or is an antibody that binds to HER2/neu.

In other aspects, the invention provides a pharmaceutical composition comprising a physiologically acceptable buffer and filamentous phage particles presenting a ligand on their surfaces, wherein the phage genome encodes a therapeutic gene product under control of a promoter and filamentous phage particles presenting a ligand on their surfaces, wherein the phage genome encodes a therapeutic gene product under control of a promoter.

These and other aspects of the present invention will become evident upon reference to the following detailed description and attached drawings. In addition, various references are set forth below which describe in more detail certain procedures or compositions (e.g, plasmids, etc.), and are therefore incorporated by reference in their entirety.

BRIEF DESCRIPTION OF THE DRAWINGS

FIG. 1A depicts the parent phage vector with wild type pIII coat protein. The base vector is M13 genome with ampicillin resistance ($Amp^R$) gene and GFP expression cassette inserted into the intergenic region between pIV and pII (MEGFP3). The MEGFP3 vector contains the following elements: ori-CMV, SV40 replication origin and CMV promoter; EGFP, enhanced green fluorescent protein gene; BGH, and a bovine growth hormone polyadenylation sequence. FIG. 1B represents the FGF-pIII fusion display phage (MF2/1G3).

FIG. 7A depicts the amount of phage protein detected using both the empty MEGFP3 vector and the FGF2 fusion construct (FGF2-MEGFP). FIG. 7B depicts the amount of FGF2 detected on the phage having the fusion construct.

DETAILED DESCRIPTION OF THE INVENTION

Figure 1A:
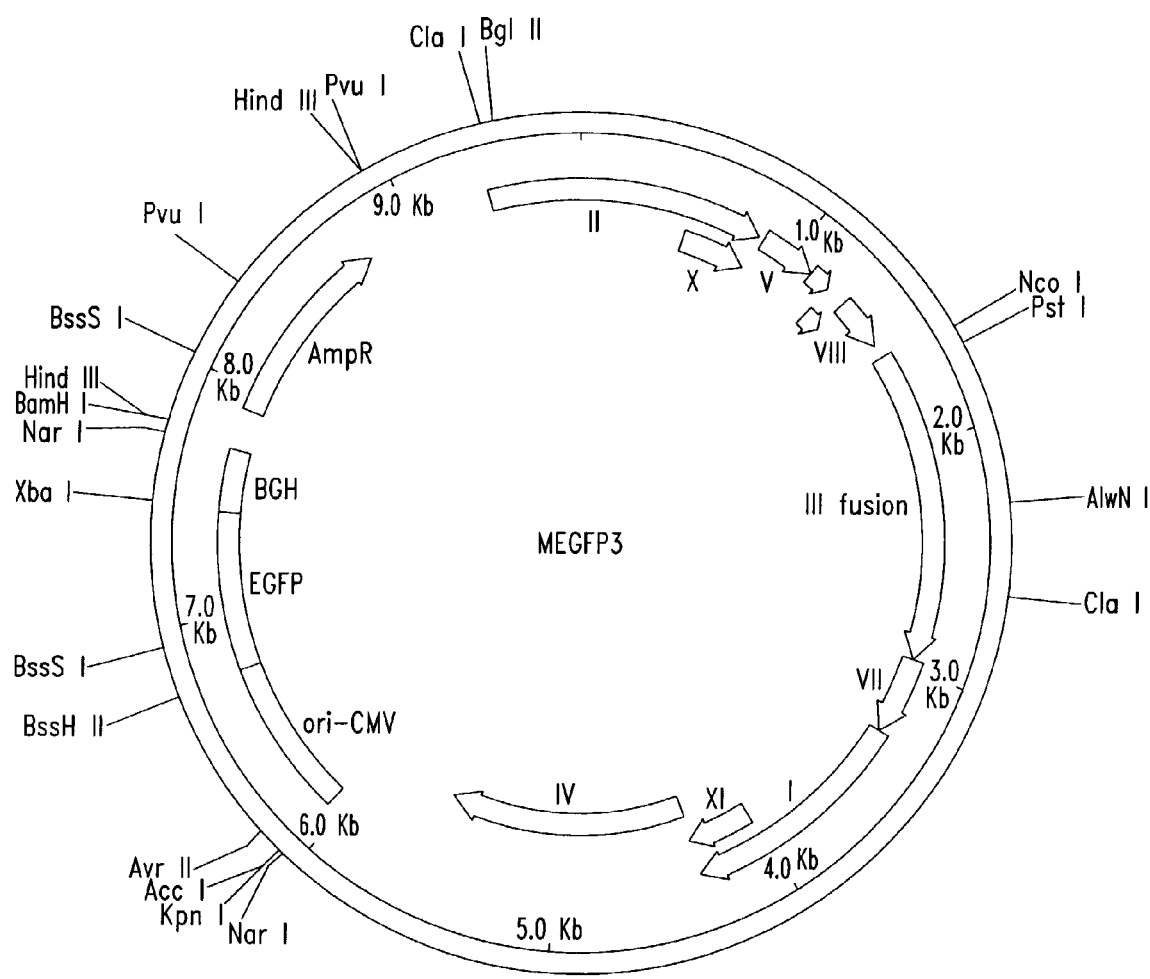
FIGS. 1A and 1B are schematic representations of phage vectors for mammalian cell transduction.

As noted above, the present invention is generally directed to methods of delivering therapeutic agents to target cells and tissues in a site-specific manner and to constructs and compositions useful in such applications. One application of the disclosed invention is in gene replacement or gene enhancement therapy. In simple terms, the vectors and methods described herein may be used in the treatment of individuals whose tissues lack the ability to produce sufficient quantities of certain important molecules and compounds—e.g., necessary enzymes. Another application of the disclosed invention utilizes the ability of the disclosed vectors to target cells with enhanced specificity, which makes such vectors ideal for the treatment of a variety of tumors and other malignancies.

As described in detail herein, preferred vectors for use in the targeted delivery of therapeutic agents include filamentous phage particles expressing one or more preselected ligands on the viral particle surface, irrespective of the manner in which the ligands are attached. Therefore, whether the means of attachment of a ligand is covalent or via a fusion protein, the targeted phage vectors of the present invention are able to deliver therapeutic nucleotide sequences to target cells.

Filamentous phage particles are particularly useful vectors as disclosed herein, in part because they have no native tropism in mammals. Therefore, there is no need to ablate the native tropism of a phage vector to make it useful in gene therapy applications, as is necessary for the more commonly-used retroviral vectors. The phage-based vectors of the present invention also possess numerous other advantages including, for example, the ability to accommodate large payloads; the ability to target specific cellular receptors with precision, without injuring healthy cells; and the ability to deliver therapeutic nucleotide sequences to the nucleus of the target cell, thereby enhancing the expression of the therapeutic sequences in the target cell.

The foregoing characteristics, and others which shall be described in greater detail below, make the vectors described herein particularly attractive for gene therapy applications, as they may readily be engineered to package, transport and deliver expressible genes of choice to the cells, tissues or organs of a patient in need of treatment. As noted above, the vectors and methods disclosed herein are particularly useful in the treatment of disease conditions that are not amenable to more "conventional" therapies.

I. Bacteriophage

A. Filamentous bacteriophages

Filamentous phage encompasses a group of bacteriophages that are able to infect a variety of Gram-negative bacteria through interaction with the tip of the F pilus. Well known filamentous phages include M13, f1, fd, and Ike.

The genomes of these phage are single-stranded DNA, but replicate through a double-stranded form. Phage particles are assembled in the bacteria and extruded into the media. Because the bacteria continue to grow and divide, albeit at a slower rate than uninfected cells, relatively high titers of phage are obtained. Moreover, replication and assembly appear to be unaffected by the size of the genome. As a consequence of their structure and life cycle, the filamentous phage have become a valuable addition in the arsenal of molecular biology tools.

Further development of filamentous phage systems have led to the development of cloning vectors, called phagemids, that combine features of plasmids and phages. Phagemids contain an origin of replication and packaging signal of the filamentous phage, as well as a plasmid origin of replication. Other elements that are useful for cloning and/or expression of foreign nucleic acid molecules are generally also present. Such elements include, without limitation, selectable genes, multiple cloning site, primer sequences. The phagemids may be replicated as for other plasmids and may be packaged into phage particles upon rescue by a helper filamentous phage. As used herein, "filamentous phage particles" refers to particles containing either a phage genome or a phagemid genome. The particles may contain other molecules in addition to filamentous capsid proteins.

Filamentous phages have also been developed as a system for displaying proteins and peptides on the surface of the phage particle. By insertion of nucleic acid molecules into genes for phage capsid proteins, fusion proteins are produced that are assembled into the capsid (Smith, *Science* 228:1315, 1985; U.S. Pat. No. 5,223,409). As a result, the foreign protein or peptide is displayed on the surface of the phage particle. Methods and techniques for phage display are well known in the art (see also, Kay et al., *Phage Display of Peptides and Proteins: A Laboratory Manual*, Academic Press, San Diego, 1996).

B. Vectors

Filamentous phage vectors generally fall into two categories: phage genome and phagemids. Either type of vector may be used within the context of the present invention, preferentially phage genome vectors are utilized. Many such commercial vectors are available. For example, the pEGFP vector series (Clontech; Palo Alto, Calif.), M13mp vectors (Pharmacia Biotech, Sweden), pCANTAB 5E (Pharmacia Biotech), pBluescript series (Stratagene Cloning Systems, La Jolla, Calif.) and others may be used. One particularly useful commercial vector is pEGFP-N1, which contains a green fluorescent protein (GFP) gene under control of the CMV immediate-early promoter. This plasmid also includes an SV40 origin of replication to enhance gene expression by allowing replication of the plasmid to high copy number in cells that make SV40 T antigen.

Other vectors are available in the scientific community (see e.g., Smith, in *Vectors: A Survey of Molecular Cloning Vectors and their Uses*, Rodriquez and Denhardt, eds., Butterworth, Boston, pp 61–84, 1988) or may be constructed using standard methods (Sambrook et al., *Molecular Biology: A Laboratory Approach*, Cold Spring Harbor, N.Y., 1989; Ausubel et al., *Current Protocols in Molecular Biology*, Greene Publishing, NY, 1995) guided by the principles discussed below.

At a minimum, for use in the present invention, the vector must accept a cassette containing a promoter and a therapeutic gene (transgene) in operative linkage. Any promoter that is active in the cells to be transfected can be used. The vector must also have a phage origin of replication and a packaging signal for assembling the vector DNA with the capsid proteins.

Other elements may be incorporated into the construct. In preferred embodiments, the construct includes a transcription terminator sequence, including a polyadenylation sequence, splice donor and acceptor sites, and an enhancer. Other elements useful for expression and maintenance of the construct in mammalian cells or other eukaryotic cells may also be incorporated (e.g., origin of replication). Because the constructs are conveniently produced in bacterial cells, elements that are necessary or enhance propagation in bacteria are incorporated. Such elements include an origin of replication, selectable marker and the like (see discussion below).

The promoter that controls expression of the transgene should be active or activatable in the targeted cell. Within the present invention, the targeted cell may be mammalian, avian, plant, and the like. Most applications of the present invention will involve transfection of mammalian cells, including human, canine, feline, equine, and the like. The choice of the promoter will depend in part upon the targeted cell type and the degree or type of control desired. Promoters that are suitable within the context of the present invention include, without limitation, constitutive, inducible, tissue specific, cell type specific, temporal specific, or event-specific.

Examples of constitutive or nonspecific promoters include the SV40 early promoter (U.S. Pat. No. 5,118,627), the SV40 late promoter (U.S. Pat. No. 5,118,627), CMV early gene promoter (U.S. Pat. No. 5,168,062), bovine papilloma virus promoter, and adenovirus promoter. In addition to viral promoters, cellular promoters are also amenable within the context of this invention. In particular, cellular promoters for the so-called housekeeping genes are useful (e.g., β-actin). Viral promoters are generally stronger promoters than cellular promoters.

Tissue specific promoters are particularly useful for expression in endothelial cells. By using one of this class of promoters, an extra margin of specificity can be attained. For example, endothelial-specific promoters are especially useful in targeting proliferative diseases involving endothelial cells. Examples of tissue or cell specific promoters include lymphoid cell specific, fibroblast cell specific, liver specific, kidney specific, hepatocyte specific and the like.

Inducible promoters may also be used. These promoters include MMTV LTR (PCT WO 91/13160), inducible by dexamethasone, metallothionein, inducible by heavy metals, and promoters with cAMP response elements, inducible by cAMP, heat shock, promoter. By using an inducible promoter, the nucleic acid may be delivered to a cell and will remain quiescent until the addition of the inducer. This allows further control on the timing of production of the gene product.

Event-type specific promoters are active or up-regulated only upon the occurrence of an event, such as tumorigenicity or viral infection. The HIV LTR is a well known example of an event-specific promoter. The promoter is inactive unless the tat gene product is present, which occurs upon viral infection. Some event-type promoters are also tissue-specific.

Additionally, promoters that are coordinately regulated with a particular cellular gene may be used. For example, promoters of genes that are coordinately expressed when a particular FGF receptor gene is expressed may be used. Then, the nucleic acid will be transcribed when the FGF receptor, such as FGFR1, is expressed, and not when FGFR2 is expressed. This type of promoter is especially useful when one knows the pattern of FGF receptor expression in a particular tissue, so that specific cells within that tissue may be killed upon transcription of a cytotoxic agent gene without affecting the surrounding tissues.

Examples of promoters discussed herein include promoters for alphafetoprotein, alpha actin, myo D, carcinoembryonic antigen, VEGF-receptor (GenBank Accession No. X89776); FGF receptor; TEK or tie 2 (GenBank Accession No. L06139); tie (GenBank Accession Nos. X60954; S89716); urokinase receptor (GenBank Accession No. S78532); E- and P-selectins (GenBank Accession Nos. M64485; L01874); VCAM-1 (GenBank Accession No. M92431); endoglin (GenBank Accession No. HSENDOG); endosialin (Rettig et al., PNAS 89:10832, 1992); alpha V-beta3 integrin (Villa-Garcia et al., *Blood* 3:668, 1994; Donahue et al., *BBA* 1219:228, 1994); endothelin-1 (GenBank Accession Nos. M25377; J04819; J05489); ICAM-3 (GenBank Accession No. S50015); E9 antigen (Wang et al., *Int. J Cancer* 54:363, 1993); von Willebrand factor (GenBank Accession Nos. HUMVWFI;. HUMVWFA); CD44 (GenBank Accession No. HUMCD44B); CD40 (GenBank Accession Nos. HACD40L; HSCD405FR); vascular-endothelial cadherin (Martin-Padura et al., *J. Pathol.* 175:51, 1995); notch 4 (Uyttendaele et al., *Development* 122:2251, 1996) high molecular weight melanoma-associated antigen; prostate specific antigen-1, probasin, FGF receptor, VEGF receptor, erb B2; erb B3; erb B4; MUC-1; HSP-27; int-1; int-2, CEA, HBEGF receptor; EGF receptor; tyrosinase, MAGE, IL-2, IL-2 receptor; prostatic acid phosphatase, probasin, prostate specific membrane antigen, alpha-crystallin, EGFR, PDGF receptor, integrin receptor, α-actin, SM1 and SM2 myosin heavy chains, calponin-h1, SM22 alpha angiotensin receptor, IL-1, IL-2, IL-3, IL-4, IL-5, IL-6, IL-7, IL-8, IL-9, IL-10, IL-11, IL-12, IL-13, IL-14, immunoglobulin heavy chain, immunoglobulin light chain, CD4, and the like are useful within the context of this invention.

In addition to the promoter, repressor sequences, negative regulators, or tissue-specific silencers may be inserted to reduce non-specific expression of the cytocide or prodrug. Multiple repressor elements may be inserted in the promoter region. Repression of transcription is independent on the orientation of repressor elements or distance from the promoter. One type of repressor sequence is an insulator sequence. Such sequences inhibit transcription (Dunaway et al., *Mol. Cell Biol* 17: 182–9, 1997; Gdula et al., *Proc. Natl. Acad. Sci.* USA 93:9378–83, 1996, Chan et al., *J Virol* 70: 5312–28, 1996; Scott and Geyer, *EMBO J* 14: 6258–67, 1995; Kalos and Fournier, *Mol Cell Biol* 15: 198–207, 1995; Chung et al., *Cell* 74: 505–14, 1993) and will silence background transcription.

Negative regulatory elements have been characterized in the promoter regions of a number of different genes. The repressor element functions as a repressor of transcription in the absence of factors, such as steroids, as does the NSE in the promoter region of the ovalbumin gene (Haecker et al., *Mol. Endocrinology* 9:1113–1126, 1995). These negative regulatory elements bind specific protein complexes from oviduct, none of which are sensitive to steroids. Three different elements are located in the promoter of the ovalbumin gene. Oligonucleotides corresponding to portions of these elements repress viral transcription of the TK reporter. One of the silencer elements shares sequence identity with silencers in other genes (TCTCTCCNA).

Repressor elements have also been identified in the promoter region of collagen II gene. Gel retardation studies showed that nuclear factors from HeLa cells bind specifically to DNA fragments containing the silencer region, whereas chondrocyte nuclear extracts did not show any binding activity (Savanger et al., *J. Biol. Chem.* 265(12): 6669–6674, 1990). Repressor elements have also been shown to regulate transcription in the carbamyl phosphate synthetase gene (Goping et al., *Nucleic Acid Research* 23(10):1717–1721, 1995). This gene is expressed in only two different cell types, hepatocytes and epithelial cells of the intestinal mucosa. Negative regulatory regions have also been identified in the promoter region of the choline acetyltransferase gene, the albumin promoter (Hu et al, *J. Cell Growth Differ.* 3(9):577–588, 1992), phosphoglycerate kinase (PGK-2) gene promoter (Misuno et al, *Gene* 119(2): 293–297, 1992), and in the 6-phosphofructo-2-kinase/fructose-2, 6-bisphosphatase gene, in which the negative regulatory element inhibits transcription in non-hepatic cell lines (Lemaigre et al, *Mol. Cell Biol.* 11(2):1099–1106). Furthermore, the negative regulatory element Tse-1 has been identified in a number of liver specific genes, including tyrosine aminotransferase (TAT). TAT gene expression is liver specific and inducible by both glucocorticoids and the cAMP signaling pathway. The cAMP response element (CRE) has been shown to be the target for repression by Tse-1 and hepatocyte-specific elements (Boshart et al, *Cell* 61(5): 905–916, 1990).

In preferred embodiments, elements that increase the expression of the desired product are incorporated into the construct. Such elements include internal ribosome binding sites (IRES; Wang and Siddiqui, *Curr. Top. Microbiol. Immunol* 203:99, 1995; Ehrenfeld and Semler, *Curr. Top. Microbiol. Immunol.* 203:65, 1995; Rees et al, *Biotechniques* 20:102, 1996; Sugimoto et al., *Biotechnology* 12:694, 1994). IRES increase translation efficiency. As well, other sequences may enhance expression. For some genes, sequences especially at the 5' end inhibit transcription and/or translation. These sequences are usually palindromes that can form hairpin structures. Any such sequences in the nucleic acid to be delivered are generally deleted. Expression levels of the transcript or translated product are assayed to confirm or ascertain which sequences affect expression. Transcript levels may be assayed by any known method, including Northern blot hybridization, Rnase probe protection and the like. Protein levels may be assayed by any known method, including ELISA.

In preferred embodiments, the phage has an origin of replication suitable for the transfected cells. Viral replication systems, such as EBV ori and EBNA gene, SV40 ori and T antigen, or BPV ori, may be used. Other mammalian replication systems may be interchanged. As well, the replication genes may cause high copy number. Expression of therapeutic genes from the phage genome may be enhanced by increasing the copy number of the phage genome. In one method, the SV40 origin of replication is used in the presence of SV40 T antigen to cause several hundred thousand copy number. The T antigen gene may be already present in the cells, introduced separately, or included in the phage genome under the transcriptional control of a suitable cell promoter. Other viral replication systems for increasing copy number can also be used, such as EBV origin and EBNA.

In another aspect of the present invention, hybrid vectors are provided which exhibit particularly advantageous features. For example, provided herein are hybrid phage vectors, such as a hybrid adeno-associated virus (AAV)/phagemid. Adeno-associated viruses are discussed in more detail below. An AAV-phage hybrid vector combines selected elements of both vector systems, providing a vector that is simple to produce in bacteria with no packaging limit, while allowing infection of quiescent cells combined with integration into the host chromosome. Vectors containing many of the appropriate elements are readily available, and can be further modified by standard methodologies to include the necessary sequences. For example, the phagemid pAAV/SVneo, ATCC Accession No. 68065, contains AAV ITR sequences and an F1 origin of replication.

Adeno-associated virus (AAV) is a defective member of the parvovirus family. The AAV genome is encapsulated as a single-stranded DNA molecule of plus or minus polarity (Berns and Rose, *J. Virol.* 5:693–699, 1970; Blacklow et al, *J. Exp. Med.* 115:755–763, 1967). Strands of both polarities are packaged, but in separate virus particles (Berns and Adler, *Virology* 9:394–396, 1972) and both strands are infectious (Samulski et al, *J. Virol.* 61:3096–3101, 1987). The single-stranded DNA genome of the human adeno-associated virus type 2 (AAV2) is 4681 base pairs in length and is flanked by inverted terminal repeated sequences of 145 base pairs each (Lusby et al, *J. Virol.* 41:518–526, 1982; Muzyczka, *Curr. Top. Microbiol. Immunol.* 158:97–129, 1992). In addition, the viral rep protein appears to mediate non-homologous recombination through the ITRs (Giraud et al, *J. Virol.* 69:6917–6924, 1995; Linden et al, *Proc. Natl. Acad. Sci.* USA 93:7966–7972, 1996). Accordingly, as parvoviral genomes have ITR sequences at each end which play a role in recombination and which are generally required for parvoviral replication and packaging, the vectors of the present invention generally contain all or a portion of at least one of the ITRs or a functional equivalent thereof.

Adeno-associated viruses may be readily obtained and their use as vectors for gene delivery has been described in, for example, Muzyczka, *Curr. Top. Microbiol. Immunol.* 158:97–129, 1992; U.S. Pat. No. 4,797,368, and PCT Application WO 91/18088. Construction of AAV vectors is described in a number of publications, including U.S. Pat. No. 5,173,414; Lebkowski et al., *Mol. Cell. Biol.* 8:3988–3996, 1988; Tratschin et al., *Mol. Cell. Biol.* 5(11): 3251–3260; Hermonat and Muzyczka, *Proc. Nat'l. Acad. Sci.* USA 81:6466–6470, 1984; U.S. Pat. Nos. 5,871,982, 5,773,289, 5,843,742, and 5,474,935; and PCT Application Nos. WO 98/45462 and WO 98/48005, all of which are incorporated herein by reference.

AAV-2 can be propagated as a lytic virus or maintained as a provirus, integrated into host cell DNA (Cukor et al., in "The Parvoviruses," Berns ed., Plenum Publishing Corp., N.Y. pp. 33–66, 1984). Although under certain conditions AAV can replicate in the absence of helper virus (Yakobson et a., *J. Virol.* 61:972–981, 1987), efficient replication requires co-infection with either adenovirus (Atchinson et al., *Science* 194:754–756, 1965; Hoggan, *Fed. Proc. Am. Soc. Exp. Biol.* 24:248, 1965; Parks et al., *J. Virol.* 1:171–180, 1967); herpes simplex virus (Buller et al., *J. Virol.* 40:241–247, 1981) or cytomegalovirus, Epstein-Barr virus, or vaccinia virus. Hence the classification of AAV as a "defective" virus.

The present invention, provides hybrid bacteriophage vectors (such as AAV-M13 vectors) that are produced in bacteria. Once purified, the bacteriophage particle containing the bacteriophage and AAV sequences are used to transfect mammalian cells. Following internalization, the AAV sequences result in integration of the transgene into the chromosome of the target cells. Accordingly, production of AAV-phage vector genomes as phage particles solves enhanced production, since phage may be produced by bacteria, and the packaging limitation of traditional AAV vectors, since phage can package DNA of at least 42 Kb or greater. Furthermore, the hybrid vector of the present invention also provides increased safety, because if the transgene insert exceeds about 4.7 Kb, viral particles cannot form and therefore such vectors could not be "rescued" by subsequent viral infection.

In related embodiments, the present invention provides an AAV-phage vector that is designed to produce functional AAV viral particles upon co-infection with a "rescue" virus, such as an adenovirus. In this embodiment, the AAV-phage particle enters the cell as a "phage particle", but once inside, produces AAV particles that infect surrounding cells. This method can thus be used to amplify gene delivery effectiveness in a target organ or tissue. Briefly, in this approach, a ligand displaying phage particle containing a AAV-phage vector which contains a transgene of interest as well as ligand fused to the pIII or pVIII coat protein is used to transduce a cell. Concurrent with or subsequent to contacting the cells with the transgene containing AAV-phage particle, a ligand displaying helper AAV-phage is also used to supply the rep and cap genes for viral particle formation. Following transduction with the appropriate bacteriophage, the cell is infected with a "rescue" virus, such as an adenovirus, which allows viral particles to form and infect neighboring cells. Alternatively, the rep and cap functions can be supplied on the helper adenoviral genome.

In other preferred embodiments, peptides or other moieties that allow or promote the escape of the vectors (and any molecule attached thereto or enclosed therein) from the endosome are incorporated and expressed on the surface of the bacteriophage. Such "other moieties" include molecules that are not themselves peptides but which have the ability to disrupt the endosomal membrane, thereby facilitating the escape of the vector, and molecules that otherwise mimic the endosomal escape properties of the within-described peptide sequences (see, e.g., published PCT Publication No. WO 96/10038 and Wagner et al., *PNAS* 89:7934–7938, 1992, the disclosures of which are incorporated by reference herein).

Peptide sequences that confer the ability to escape the endosome are particularly preferred. Such sequences are well known and can be readily fused covalently or genetically to a coat protein, such as gene III or gene VIII of filamentous phage. Although fusion of one or more peptide sequences to a coat protein is described herein as a preferred embodiment, it should be understood that other methods of attachment—and other moieties besides peptides—are useful as disclosed herein.

Thus, an example of a dual display filamentous phage presents a ligand (e.g., FGF) as a fusion to gene III and an endosomal escape peptide fused to gene VIII. The locations of the ligand and escape sequences are interchangeable and furthermore may reside in the same fusion protein. Escape sequences that are suitable include, without limitation, the following exemplary sequences: a peptide of *Pseudomonas* exotoxin (Donnelly, et al., *PNAS*, 90, 3530–3534, 1993); influenza peptides such as the HA peptide and peptides derived therefrom, such as peptide FPI3; Sendai Virus fusogenic peptide; the fusogenic sequence from HIV gp1 protein; Paradaxin fusogenic peptide; and Melittin fusogenic peptide (see published PCT Publication No. WO 96/41606, the disclosures of which are incorporated by reference herein.) Examples of two other endosome-disruptive peptides, sometimes called fusogenic peptides, are:

```
GLFEAIEGFIENGWEGMIDGGGC; and    (SEQ. ID No. 1)
GLFEAIEGFIENGWEGMIDGWYGC.       (SEQ. ID No. 2)
```

Other peptides useful for disrupting endosomes may be identified by various general characteristics. For example, endosome-disrupting peptides are often about 25–30 residues in length, contain an alternating pattern of hydrophobic domains and acidic domains, and at low pH (e.g., pH 5) form amphipathic α-helices. The endosome-disruptive peptide may be present as single or multiple copies at the N- or C-terminus of the ligand.

Escape peptides may also be selected using a molecular evolution strategy. Briefly, in one strategy, a library of random peptides is engineered into the gene VIII protein of a phage vector that has a ligand fused to gene III and that carries a detectable (e.g., GFP) or selectable marker (e.g., drug resistance). Mammalian cells are infected with the library and the cells selected by detection of the marker. The cells that have the most efficient endosomal escape sequence should have the highest expression or most resistance. Multiple rounds of selection may be performed to reduce the complexity of the recovered peptide encoding genes. The peptide genes are recovered and engineered into the phage vectors.

In addition, or alternatively, membrane-disruptive peptides may be incorporated into the complexes. For example, adenoviruses are known to enhance disruption of endosomes. Virus-free viral proteins, such as influenza virus hemagglutinin HA-2, also disrupt endosomes and are useful in the present invention. Other proteins may be tested in the assays described herein to find specific endosome disrupting agents that enhance gene delivery. In general, these proteins and peptides are amphipathic (see Wagner et al., *Adv. Drug. Del. Rev.* 14:113–135, 1994).

Another sequence that may be included in a vector is a sequence that facilitates trafficking proteins into the nucleus. For enhanced expression, it is preferred that the therapeutic nucleotide sequence is trafficked to the nucleus. These so-called nuclear translocation or nuclear localization sequences (NLS) are generally rich in positively charged amino acids. Because the carboxyl terminus of gene VIII protein of filamentous phage already carries a positive charge, increased charge and likeliness of nuclear transport may be enhanced by fusing known mammalian cell NLS sequences to the gene VIII protein. NLS fusions to other coat proteins of filamentous phage may be substituted. The NLS may be fused to a capsid protein distinct from a ligand/capsid fusion.

Examples of NLS sequences include those resembling the short basic NLS of the SV40 T antigen; the bipartite NLS of nucleoplasmin; the ribonucleoprotein sequence A1; the small nuclear ribonucleoprotein sequence U1A, and human T-lymphocyte virus-1 Tax protein. Other useful NLS sequences include the HIV matrix protein NLS; and the nuclear translocation components importin/hSRP1 and Ran/TC4; the consensus sequence KXX(K/R) (SEQ ID NO: 3) flanked by Pro or Ala; or the NLS from antennapedia (See, WO 96/41606).

In some instances, nucleic acid condensing peptides are linked to non-basic nuclear localization sequences which function to transport nucleoprotein. Examples of such sequences include influenza nucleoprotein and HIV MA protein. Other useful NLS include hnRNP A1 protein, a protein which transports ribonucleoprotein complexes. Another useful NLS is included in peptides such as NBC1 and NBC2, which also function to condense nucleic acid. (See, WO 96/41606) The present invention thus contemplates use of the foregoing sequences as well as the others disclosed herein.

A random peptide library of sequences may be screened for novel sequences that promote nuclear translocation. Briefly, in one such method a library of random peptide genes is fused to filamentous phage genes VIII, VII, or IX and screened for efficient nuclear translocation by assay of infected cells for reporter gene expression or drug selection.

Additional factors that enhance expression of the transgene may be included. Such factors may be identified by a method in which sequences are fused to phage coat proteins and the phage are selected on the basis of efficient reporter gene expression. Known DNA repair enzymes or polymerases from mammalian cells or single stranded DNA viruses are candidate sequences.

Phage that present the ligand as a fusion with a phage coat protein are engineered to contain the appropriate coding regions. For the filamentous phages, usually genes III and VIII are used. Other capsid proteins may be substituted. Techniques for inserting ligand coding sequence into a phage gene are well known (see e.g., Sambrook et al., supra; Ausubel et al, supra).

In certain embodiments, propagation or stable maintenance of the construct may be desirable or may be necessary to attain a sufficient amount or concentration of the gene product for effective gene therapy. Examples of replicating and stable eukaryotic origins of replication are known.

II. Ligands

As used herein, "ligand" refers to any peptide, polypeptide, protein or non-protein, such as a peptidomimetic, that is capable of binding to a cell-surface molecule and internalizing. Internalization through an endosomal pathway is a preferred mode of entry. As used herein, to "bind to a receptor" refers to the ability of a ligand to specifically recognize and detectably bind to a receptor, as assayed by standard in vitro assays.

Within the context of this invention, the ligand is conjugated to a protein of a bacteriophage, either as a fusion protein or through chemical conjugation, and is used to deliver a nucleic acid payload (i.e., therapeutic gene) to a cell. Numerous molecules are known that that bind a specific receptor and are internalized, generally by way of endosomes. Yet other molecules are antibodies and antibody derivatives. In addition, methods are provided for selection of other ligands that satisfy the criteria presented above.

Fragments of these ligands may be used within the present invention, so long as the fragment retains the ability to bind to the appropriate cell surface molecule. Likewise, ligands with substitutions or other alterations, but which retain binding ability, may also be used. As well, a particular ligand refers to a polypeptide(s) having an amino acid sequence of the native ligand, as well as modified sequences, (e.g., having amino acid substitutions, deletions, insertions or additions compared to the native protein) as long as the ligand retains the ability to bind to its receptor on an endothelial cell and be internalized.

Ligands also encompass muteins that possess the ability to bind to its receptor expressing cells and be internalized. Such muteins include, but are not limited to, those produced by replacing one or more of the cysteines with serine as described herein. Typically, such muteins will have conservative amino acid changes. DNA encoding such muteins will, unless modified by replacement of degenerate codons, hybridize under conditions of at least low stringency to native DNA sequence encoding the wild-type ligand.

DNA encoding a ligand may be prepared synthetically based on known amino acid or DNA sequence, isolated using methods known to those of skill in the art (e.g., PCR amplification), or obtained from commercial or other sources. DNA encoding a ligand may differ from the above sequences by substitution of degenerate codons or by encoding different amino acids. Differences in amino acid sequences, such as those occurring among the homologous ligand of different species as well as among individual organisms or species, are tolerated as long as the ligand binds to its receptor. Ligands may be isolated from natural sources or made synthetically, such as by recombinant means or chemical synthesis.

It is not necessary that the ligands used in the context of this invention retain any of its in vivo biological activities, other than binding a receptor on a cell and be internalized. However, it may be desirable in certain contexts for a ligand to manifest certain of its biological activities. For example, if VEGF is used as a carrier for DNA encoding a molecule useful in wound healing, it would be desirable that VEGF exhibit vessel permeability activity and promotion of fibroblast migration and angiogenesis. In the examples, FGF muteins with reduced mitogenic activity have been constructed by site-directed mutagenesis. Non- or reduced-mitogenic proteins can also be constructed by swapping the receptor-binding domain with the receptor-binding domain of a related protein. By way of example, the domain of FGF2 may be swapped with the receptor-binding domain of FGF7 to create an FGF that does not cause proliferation and may alter the binding profile. If the ligand has been modified so as to lack one or more biological activities, binding and internalization may still be readily assayed by any one of the following tests or other equivalent tests. Generally, these tests involve labeling the ligand, incubating it with target cells, and visualizing or measuring intracellular label. For example, briefly, the ligand may be fluorescently labeled with FITC or radiolabeled with $^{125}$I, incubated with cells and examined microscopically by fluorescence microscopy or confocal microscopy for internalization. It will be apparent from the teachings provided within the subject application which of the biological activities are desirable to maintain.

A. Proteins that Bind to Cells and Internalize

The ligands may be produced by recombinant or other means in preparation for attachment to phage capsid proteins. The DNA sequences and methods to obtain the sequences of these ligands are well known. (see GenBank). Based on the DNA sequences, the genes may be synthesized either synthetically (for small proteins), amplified from cell genomic or cDNA, isolated from genomic or cDNA libraries and the like. Restriction sites to facilitate cloning into the phage or phagemid vector may be incorporated, such as in primers for amplification.

Such molecules include, without limitation, proteins that bind cancer cells, endothelial cells, cardiovascular cells, cells in the eye and the like. Such ligands include growth factors and cytokines. Many growth factors and families of growth factors share structural and functional features and may be used in the present invention. Families of growth factors include fibroblast growth factors FGF-1 through FGF-15, and vascular endothelial growth factor (VEGF). Other growth factors, such as PDGF (platelet-derived growth factor), TGF-α (transforming growth factor), TGF-β, HB-EGF, angiotensin, bombesis, erythopoietin, stem cell factor, M-CSF, G-CSF, GM-CSF, and endoglin also bind to specific identified receptors on cell surfaces and may be used in the present invention. Cytokines, including interleukins, CSFs (colony stimulating factors), and interferons, have specific receptors, and may be used as described herein.

For example, ligands and ligand/receptor pairs include urokinase/urokinase receptor (GenBank Accession Nos. X02760/X74309); α-1,3 fucosyl transferase, α1-antitrypsin/E-selectin (GenBank Accession Nos. M98825, D38257/M87862); P-selectin glycoprotein ligand, P-selectin ligand/P-selectin (GenBank Accession Nos. U25955, U02297/L23088), VCAM1/NVLA-4 (GenBank Accession Nos. X53051/X16983); E9 antigen (Blann et al., *Atherosclerosis* 120:221, 1996)/TGFβ receptor; Fibronectin (GenBank Accession No. X02761); type I α1-collagen (GenBank Accession No. Z74615), type I β2-collagen (GenBank Accession No. Z74616), hyaluronic acid/CD44 (GenBank Accession No. M59040); CD40 ligand (GenBank Accession No. L07414)/CD40 (GenBank Accession No. M83312); EFL-3, LERTK-2 ligands (GenBank Accession Nos. L37361, U09304) for elk-1 (GenBank Accession No. M25269); VE-cadherin (GenBank Accession No. X79981); ligand for catenins; ICAM-3 (GenBank Accession No. X69819) ligand for LFA-1, and von Willebrand Factor (GenBank Accession No. X04385), fibrinogen and fibronectin (GenBank Accession No. X92461) ligands for $\alpha_v\beta_3$ integrin (GenBank Accession Nos. U07375, L28832).

Other ligands include CSF-1 (GenBank Accession Nos. M11038, M37435); GM-CSF (GenBank Accession No. X03021); IFN-α (interferon) (GenBank Accession No. A02076; WO 8502862-A); IFN-γ (GenBank Accession No. A02137; WO 8502624-A); IL-1-α (interleukin 1 alpha) (GenBank Accession No. X02531, M15329); IL-1-β (interleukin 1 beta) (GenBank Accession No. X02532, M15330, M15840); IL-1 (GenBank Accession No. K02770, M54933, M38756); IL-2 (GenBank Accession No. A14844, A21785, X00695, X00200, X00201, X00202); IL-3 (GenBank Accession No. M14743, M20137); IL-4 (GenBank Accession No. M13982); IL-5 (GenBank Accession No. X04688, J03478); IL-6 (GenBank Accession No. Y00081, X04602, M54894, M38669, M14584); IL-7 (GenBank Accession No. J04156); IL-8 (GenBank Accession No. Z11686); IL-10 (GenBank Accession No. X78437, M57627); IL-11 (GenBank Accession No. M57765 M37006); IL-13 (GenBank Accession No. X69079, U10307); TNF-α (Tumor necrosis factor) (GenBank Accession No. A21522); TNF-β (GenBank Accession No. D12614); and GP30 ligand (S68256) for erbB2.

Still other ligands include PDGF (GenBank Accession No. X03795, X02811), angiotensin (GenBank Accession No. K02215), and all RGD-containing peptides and proteins, such as ICAM-1 (GenBank Accession No. X06990) and VCAM-1 (GenBank Accession No. X53051) that bind to integrin receptors. Other ligands include TNFα (GenBank Accession No. A21522, X01394), IFN-γ (GenBank Accession No. A11033, A11034), IGF-I (GenBank Accession No. A29117, X56773, S61841, X56774, S61860), IGF-II (GenBank Accession No. A00738, X06159, Y00693), atrial natriuretic peptide (GenBank Accession No. X54669), endothelin-1 (GenBank Accession No. Y00749), coagulation factor Xa (GenBank Accession No. L00395, L00396, L29433, N00045, M14327), TGF-β1 (GenBank Accession No. A23751), IL-1α (GenBank Accession No. X03833), IL-1β (GenBank Accession No. M15330), and endoglin (GenBank Accession No. X72012).

The family of FGF proteins presently includes FGF-1 (acidic FGF or aFGF), FGF-2 (basic FGF or bFGF), FGF-3 (int-2), FGF-4 (hst-1/K-FGF), FGF-5, FGF-6 (hst-2), FGF-7 (keratinocyte growth factor or KGF), FGF-8, FGF-9, FGF-11 (WO 96/39507), FGF-13 (WO 96/39508), FGF-14 (WO 96/39506), and FGF-15 (WO 96/39509). Other polypeptides that are reactive with an FGF receptor, that is any polypeptide that specifically interacts with an FGF receptor, preferably the high affinity FGF receptor, and is transported by way of endosomes into the cell by virtue of its interaction with the FGF receptor are suitable within the present invention.

B. Antibodies to Receptors that Internalize

Antibodies to molecules expressed on the surface of cells are useful within the context of the present invention as long as the antibody is internalized following binding. Such antibodies include, but are not limited to, antibodies to FGF receptors, VEGF receptors, urokinase receptor, E- and P-selectins, VCAM-1, PDGF receptor, TGF receptor, endosialin, alpha$_v$, beta$_3$ integrin, LFA-1, E9 antigen, CD40, cadherins, and elk-1. Antibodies that are specific to cell surface molecules expressed by cells are readily generated as monoclonals or polyclonal antisera. Many such antibodies are available (e.g., from American Type Culture Collection, Rockville, Md.). Alternatively, antibodies to ligands that bind/internalize may also be used. In such a strategy, the phage particles will have antibody on their surface, which will then be complexed to the ligand (see further discussion below).

Within the context of the present invention, antibodies are understood to include monoclonal antibodies, polyclonal antibodies, anti-idiotypic antibodies, antibody fragments (e.g., Fab, and F(ab')$_2$, F$_v$ variable regions, or complementarity determining regions). Antibodies are generally accepted as specific against indolicidin analogues if they bind with a K$_d$ of greater than or equal to $10^{-7}$M, preferably greater than of equal to $10^{-8}$M. The affinity of a monoclonal antibody or binding partner can be readily determined by one of ordinary skill in the art (see Scatchard, *Ann. N.Y Acad. Sci.* 51:660–672, 1949). Once suitable antibodies have been obtained, they may be isolated or purified by many techniques well known to those of ordinary skill in the art.

Commercially available antibodies to cell surface molecules may be used if they internalize. Briefly, antibodies are raised by immunization of mice, rats, rabbits or other animals with normal, tumorigenic, or cultured cells. Various immunization protocols may be found in for example, Harlow and Lane *Antibodies: A Laboratory Manual*, Cold Spring Harbor Laboratory, 1988 and Coligan et al. *Current Protocols in Immunology*, Greene Publishing, 1995. Following immunization, spleen or lymph nodes are collected for generating hybridomas or serum is collected for polyclonal antibodies. Hybridomas are preferred (see, U.S. Pat. Nos. RE 32,011, 4,902,614, 4,543,439, and 4,411,993; Harlow and Lane, supra; and Coligan et al., supra; for protocols). Antibody-secreting hybridomas are grown, and the antibodies are tested for binding to the immunizing cells by ELISA, section staining, flow cytometry, confocal microscopy and the like.

Positive antibodies are further tested for internalization. One assay that is used is a test for an antibody to kill cells. Briefly, the test hybridoma antibody and test cells are incubated. Unbound antibody is washed away. A second stage antibody, such as an anti-IgG antibody, conjugated to saporin is incubated with the test cells. Cell killing is assessed by any known assay, including trypan blue exclusion, MTT uptake, fluorescein diacetate staining, and the like.

Other techniques may also be utilized to construct monoclonal antibodies (see Huse et al., *Science* 246:1275–1281, 1989; Sastry et al., *Proc. Natl. Acad Sci* USA 86:5728–5732, 1989; Alting-Mees et al., *Strategies in Molecular Biology* 3:1–9, 1990; describing recombinant techniques). These techniques include cloning heavy and light chain immunoglobulin cDNA in suitable vectors, such as λImmunoZap(H) and λImmunoZap(L). These recombinants may be screened individually or co-expressed to form Fab fragments or antibodies (see Huse et al., supra; Sastry et al., supra). Positive plaques may subsequently be converted to a non-lytic plasmid that allows high level expression of monoclonal antibody fragments from *E. coli*.

Similarly, portions or fragments, such as Fab and Fv fragments, of antibodies may also be constructed utilizing conventional enzymatic digestion or recombinant DNA techniques to yield isolated variable regions of an antibody. Within one embodiment, the genes which encode the variable region from a hybridoma producing a monoclonal antibody of interest are amplified using nucleotide primers for the variable region. In addition, techniques may be utilized to change a "murine" antibody to a "human" antibody, without altering the binding specificity of the antibody.

C. Selection of other Ligands

Other receptor-binding ligands may be used in the present invention. Any protein, peptide, analogue, peptidomimetic or fragment thereof that binds to a cell-surface receptor and is internalized may be used. These ligands may be identified and selected by a method such as phage display (see, for example, U.S. Pat. No. 5,223,409; and co-pending application "Methods using phage display for selecting internalizing ligands for gene delivery", filed Aug. 29, 1997.)

Briefly, in this method, DNA sequences are inserted into the gene III or gene VIII gene of a filamentous phage, such as M13. Several vectors with multicloning sites have been developed for insertion (McLafferty et al., *Gene* 128:29–36, 1993; Scott and Smith, *Science* 249:386–390, 1990; Smith and Scott, *Methods Enzymol.* 217:228–257, 1993). The inserted DNA sequences may be randomly generated or be variants of a known binding domain for binding target cells. Single chain antibodies may readily be generated using this method. Generally, the inserts encode from 6 to 20 amino acids. The peptide encoded by the inserted sequence is displayed on the surface of the bacteriophage. Bacteriophage expressing a binding domain for the target cells are selected for by binding to cells or preferably by expression of a detectable or selectable transgene encoded by the bacteriophage genome.

For transgene selection or detection methods, the cells are grown in selective medium (e.g., containing drug) or isolated on the basis of expression (e.g., flow cytometry). The insert DNA is recovered, generally by amplification of lysed cells, analyzed (e.g., DNA sequence analysis) and used in the present invention (Barry et al., supra). Eluted phage are propagated in the bacteria host. In any of these methods, further rounds of selection may be performed to select for a few phage binding with high affinity. The DNA sequence of the insert in the binding phage is then determined. Once the predicted amino acid sequence of the binding peptide is known, sufficient peptide for use in chemical conjugate may be made by recombinant means or synthetically and by recombinant means for use as a fusion protein. The peptide may be generated as a tandem array of two or more peptides, in order to maximize affinity or binding.

D. Modifications of Receptor-Binding Internalized Ligands

The ligands for use herein may be customized for a particular application. Means for modifying proteins is provided below. Briefly, additions, substitutions and deletions of amino acids may be produced by any commonly employed recombinant DNA method. Modified peptides, especially those lacking proliferative function, and chimeric peptides, which retain their specific binding and internalizing activities, are also contemplated for use herein. Modifications also include the addition or deletion of residues, such as the addition of a cysteine to facilitate conjugation and to form conjugates that contain a defined molar ratio (e.g, 1:1) of the polypeptides (see, e.g., U.S. Pat. No. 5,175,147; PCT Application No. WO 89/00198, U.S. Ser.

No. 07/070,797; PCT Application No. WO 91/15229; and U.S. Ser. No. 07/505,124). Still other useful modifications include adding sequence that are subject to post-translational modification (e.g., myristylation, palmatylation, phophorylation, ribosylation) that improve or alter protein function, stability or the like.

Modification of the polypeptide may be effected by any means known to those of skill in this art. The preferred methods herein rely on modification of DNA encoding the polypeptide and expression of the modified DNA. DNA encoding one of the receptor-binding internalized ligands discussed above may be mutagenized using standard methodologies. For example, cysteine residues that are responsible for aggregate formation may be deleted or replaced. If necessary, the identity of cysteine residues that contribute to aggregate formation may be determined empirically, by deleting and/or replacing a cysteine residue and ascertaining whether the resulting protein aggregates in solutions containing physiologically acceptable buffers and salts. In addition, fragments of these receptor-binding internalized ligands may be constructed and used. The binding region of many of these ligands have been delineated. For example, the receptor binding region of FGF2 has been identified by mutation analysis and FGF peptide agonists/antagonists to reside between residues 33–77 and between 102–129 of the 155 amino acid form (Baird et al., *PNAS* 85:2324; Erickson et al, *Biochem.* 88:3441). Exons 1–4 of VEGF are required for receptor binding. Fragments may also be shown to bind and internalize by any one of the tests described herein.

Mutations may be made by any method known to those of skill in the art, including site-specific or site-directed mutagenesis of DNA encoding the protein and the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., *Meth. Enzymol.* 15:3, 1987). In general, site-directed mutagenesis is performed by preparing a single-stranded vector that encodes the protein of interest (i.e., a member of the FGF family or a cytotoxic molecule, such as a saporin). An oligonucleotide primer that contains the desired mutation within a region of homology to the DNA in the single-stranded vector is annealed to the vector followed by addition of a DNA polymerase, such as *E. coli* DNA polymerase I (Klenow fragment), which uses the double stranded region as a primer to produce a heteroduplex in which one strand encodes the altered sequence and the other the original sequence. The heteroduplex is introduced into appropriate bacterial cells and clones that include the desired mutation are selected. The resulting altered DNA molecules may be expressed recombinantly in appropriate host cells to produce the modified protein.

Suitable conservative substitutions of amino acids are well-known and may be made generally without altering the biological activity of the resulting molecule. For example, such substitutions are generally made by interchanging within the groups of polar residues, charged residues, hydrophobic residues, small residues, and the like. If necessary, such substitutions may be determined empirically merely by testing the resulting modified protein for the ability to bind to and internalize upon binding to the appropriate receptors. Those that retain this ability are suitable for use in the conjugates and methods herein. As such, an amino acid residue of a receptor-binding internalized ligand is non-essential if the polypeptide that has been modified by deletion or alteration of the residue possesses substantially the same ability to bind to its receptor and internalize a linked agent as the unmodified polypeptide.

E. Peptidomimetic Ligands

Ligands or fragments thereof that bind to a cell-surface receptor and are internalized, but which are mimetics of "true" polypeptides, are also contemplated for use in the present invention. Thus, in one aspect, the invention contemplates the preparation and use of non-peptide peptidomimetics useful for mimicking the activity of peptides, which makes peptidomimetics additional sources of targeting ligands that may be attached to the phage-based vectors of the present invention.

Methods of generating and identifying peptidomimetics useful as described herein are known in the art; (see, e.g., WO 93/17032). For example, the aforementioned application describes a process of preparing peptidomimetic compounds useful for mimicking the activity of peptides and described the peptide-like activity of one such mimetic. Similarly, the production of peptidomimetic drugs via utilizing chemically modified moieties to mimic antibody structure, based on conformation studies, is described in U.S. Pat. No. 5,331,573. Methods of testing the drugs so prepared is also disclosed therein. Peptidomimetics of antibodies are thus useful as disclosed herein, not only as ligands but as molecules useful in linking phage particles to targeting ligands.

Other useful peptidomimetic molecules useful as ligands and/or "linkers" herein are described in published PCT Publication No. WO 92/20704; Brandt, et al., *Antimicrob Agents Chemother,* 40:1078, 1996; Sepp-Lorenzino, et al., *Cancer Res,* 55:5302, 1995; and Chander et al., *J Pharm Sci,* 84:404, 1995.

Notwithstanding the fact that such mimetics are not true peptides, various covalent and non-covalent means of linking such peptidomimetic molecules to phage coat proteins may be used as disclosed herein.

F. Expression Vectors for Production of Ligands

As used herein, "operative linkage" or operative association of two nucleotide sequences refers to the functional relationship between such sequences. Nucleotide sequences include, but are not limited to, DNA encoding a product, DNA encoding a signal sequence, promoters, enhancers, transcriptional and translational stop sites, and polyadenylation signals. For example, operative linkage of DNA encoding a cytocide to a promoter refers to the physical and functional relationship between the DNA and the promoter such that transcription of the DNA is initiated from the promoter by an RNA polymerase that specifically recognizes, binds to, and transcribes the DNA.

Host organisms include those organisms in which recombinant production of heterologous proteins have been carried out, such as bacteria (for example, *E. coli*), yeast (for example, *Saccharomyces cerevisiae* and *Pichia pastoris*), mammalian cells, and insect cells. Presently preferred host organisms are *E. coli* bacterial strains.

The DNA construct encoding the desired protein is introduced into a plasmid for expression in an appropriate host. In preferred embodiments, the host is a bacterial host. The sequence encoding the ligand is preferably codon-optimized for expression in the particular host. Thus, for example, if human FGF-2 is expressed in bacteria, the codons would be optimized for bacterial usage. For small coding regions, the gene can be synthesized as a single oligonucleotide. For larger proteins, splicing of multiple oligonucleotides, mutagenesis, or other techniques known to those in the art may be used. The sequences of nucleotides in the plasmids that are regulatory regions, such as promoters and operators, are operationally associated with one another for transcription. The sequence of nucleotides encoding the growth factor or growth factor-chimera may also include DNA encoding a secretion signal, whereby the resulting peptide is a precursor protein. The resulting processed protein may be recovered from the periplasmic space or the fermentation medium.

The plasmids used herein include a promoter in operative association with the DNA encoding the protein or polypeptide of interest and are designed for expression of proteins in a bacterial host. Suitable promoters for expression of proteins and polypeptides herein are widely available and are well known in the art. Inducible promoters or constitutive promoters that are linked to regulatory regions are preferred. Such promoters include, but are not limited to, the T7 phage promoter and other T7-like phage promoters, such as the T3, T5 and SP6 promoters, the trp, lpp, and lac promoters, such as the lacUV5, from *E. coli*; the P10 or polyhedron gene promoter of baculovirus/insect cell expression systems (see, e.g., U.S. Pat. Nos. 5,243,041, 5,242,687, 5,266,317, 4,745,051, and 5,169,784) and inducible promoters from other eukaryotic expression systems. For expression of the proteins such promoters are inserted in a plasmid in operative linkage with a control region such as the lac operon.

Preferred promoter regions are those that are inducible and functional in *E. coli*. Examples of suitable inducible promoters and promoter regions include, but are not limited to: the *E. coli* lac operator responsive to isopropyl β-D-thiogalactopyranoside (IPTG; see, et al. Nakamura et al., *Cell* 18:1109–1117, 1979); the metallothionein promoter metal-regulatory-elements responsive to heavy-metal (e.g., zinc) induction (see, e.g., U.S. Pat. No. 4,870,009 to Evans et al.); the phage T7lac promoter responsive to IPTG (see, e.g., U.S. Pat. No. 4,952,496; and Studier et al., *Meth. Enzymol.* 185:60–89, 1990) and the TAC promoter.

The plasmids also preferably include a selectable marker gene or genes that are functional in the host. A selectable marker gene includes any gene that confers a phenotype on bacteria that allows transformed bacterial cells to be identified and selectively grown from among a vast majority of untransformed cells. Suitable selectable marker genes for bacterial hosts, for example, include the ampicillin resistance gene (Amp$^r$), tetracycline resistance gene (Tc$^r$) and the kanamycin resistance gene (Kan$^r$). The kanamycin resistance gene is presently preferred.

The plasmids may also include DNA encoding a signal for secretion of the operably linked protein. Secretion signals suitable for use are widely available and are well known in the art. Prokaryotic and eukaryotic secretion signals functional in *E. coli* may be employed. The presently preferred secretion signals include, but are not limited to, those encoded by the following *E. coli* genes: ompA, ompT, ompF, ompC, beta-lactamase, and alkaline phosphatase, and the like (von Heijne, *J. Mol. Biol.* 184:99–105, 1985). In addition, the bacterial pelB gene secretion signal (Lei et al., *J. Bacteriol.* 169:4379, 1987), the phoA secretion signal, and the cek2 functional in insect cell may be employed. The most preferred secretion signal is the *E. coli* ompA secretion signal. Other prokaryotic and eukaryotic secretion signals known to those of skill in the art may also be employed (see, e.g., von Heijne, *J. Mol. Biol.* 184:99–105, 1985). Using the methods described herein, one of skill in the art can substitute secretion signals that are functional in either yeast, insect or mammalian cells to secrete proteins from those cells.

In preferred embodiments, the DNA plasmids also include a transcription terminator sequence. The entire transcription terminator may be obtained from a protein-encoding gene, which may be the same or different from the inserted gene or the source of the promoter.

Particularly preferred plasmids for transformation of *E. coli* cells include the pET expression vectors (see U.S Pat. No. 4,952,496; available from Novagen, Madison, Wis.). Such plasmids include pET 11a, which contains the T7lac promoter, T7 terminator, the inducible *E. coli* lac operator, and the lac repressor gene; pET 12a–c, which contains the T7 promoter, T7 terminator, and the *E. coli* ompT secretion signal; and pET 15b, which contains a His-Tag™ leader sequence for use in purification with a His column and a thrombin cleavage site that permits cleavage following purification over the column, the T7-lac promoter region and the T7 terminator.

Other preferred plasmids include the pKK plasmids, particularly pKK 223-3, which contains the tac promoter (Pharmacia Biotech). Plasmid pKK has also been modified by replacement of the ampicillin resistance gene with a kanamycin resistance cassette (Pharmacia Biotech). Other plasmids include the pIN-IIIompA plasmids (see U.S. Pat. No. 4,575,013), which have a cloning site linked in transcriptional reading frame with four functional fragments derived from the lipoprotein gene of *E. coli* and an ompA signal sequence Baculovirus vectors, such as pBlueBac (also called pJVETL and derivatives thereof), particularly pBlueBac III (Invitrogen, San Diego, Calif.) may be used for expression of the polypeptides in insect cells. A DNA construct may be made in a baculovirus vector and then co-transfected with wild type virus into sf9 insect cells from *Spodoptera frugiperda* (see, e.g., Luckow et al., *Bio/technology* 6:47–55, 1988, and U.S. Pat. No. 4,745,051).

Expression vectors compatible with eukaryotic cells, preferably those compatible with mammalian cells, can also be used to form the recombinant nucleic acid molecules for use in the present invention. Mammalian cell expression vectors are well known in the art and are available from several commercial sources. Typically, such vectors are provided containing convenient restriction sites for insertion of the desired DNA segment, and provide the signals required for gene expression in a mammalian cell. Typical of such vectors are the pREP series vectors and pEBVhis available from Invitrogen (San Diego, Calif.), the vectors pTDT1 (ATCC #31255), pCP1 (ATCC #37351) and pJ4W (ATCC #37720) available from the American Type Culture Collection (ATCC), and the like.

Successfully transformed cells, i.e., cells that contain a nucleic acid molecule of the present invention, can be identified by well known techniques. For example, cells resulting from the introduction of an rDNA of the present invention can be subjected to assays for detecting the presence of specific rDNA using a nucleic acid hybridization method such as that described by Southern, *J. Mol. Biol.* 98:503, 1975 or Berent et al., *Biotech.* 3:208, 1985. In addition to directly assaying for the presence of rDNA, successful transformation can be confirmed by well known immunological methods for the presence of expressed protein. For example, cells successfully transformed with an expression vector produce proteins which then can be assayed directly by immunological methods or for the presence of the function of the expressed protein.

Other suitable mammalian expression vectors are well known and may be readily obtained from a variety of sources. (See, e.g., Ausubel et al., 1995; Sambrook et al., supra; Invitrogen, San Diego, Calif.; Novagen, Madison, Wis.; Pharmacia Biotech; and others.)

In various preferred embodiments, the DNA fragment is replicated in bacterial cells, preferably in *E. coli*. The preferred DNA fragment also includes a bacterial origin of replication. Preferred bacterial origins of replication include, but are not limited to, the fl-ori and cot E1 origins of replication. Preferred hosts contain chromosomal copies of DNA encoding T7 RNA polymerase operably linked to an inducible promoter, such as the lacUV promoter (see U.S. Pat. No. 4,952,496). Such hosts include, but are not limited to, lysogens *E. coli* strains HMS174(DE3)pLysS, BL21 (DE3)pLysS, HMS174(DE3) and BL21(DE3). Strain BL21 (DE3) is preferred.

The DNA fragments provided may also contain a gene coding for a repressor protein, which is capable of repressing the transcription of a promoter that contains a binding site for the repressor protein. The promoter can be derepressed by altering the physiological conditions of the cell. Preferred repressor proteins include, but are not limited to the *E. coli* lacI repressor responsive to IPTG induction, the temperature sensitive $\lambda$ cI857 repressor, and the like.

In one preferred embodiment described herein, the "plasmid" is phagemid pEGFP-N1 (Clontech; Palo Alto, Calif.), which contains a green fluorescent protein (GFP) gene under control of the CMV immediate-early promoter. The CMV promoter is highly active in a large variety of mammalian cell lines; however, other mammalian cell promoters can be used. Examples of other useful promoters active in mammalian cells include viral promoters (e.g retroviral LTRs, MMTV LTR, HIV LTR, SV40 early and late promoters, Bovine Papilloma Virus, BPV) or non-viral inducible promoters (e.g. metallothionein, heat shock, steroid hormone responsive promoters). Still other promoters include those that are constitutive (e.g. Beta Actin) or tissue-specific (e.g. alphafetoprotein (AFP), carcinoembryonic antigen (CEA), alpha actin, and Myo D). Additional useful promoters are described elsewhere herein.

Preferably, the phagemid also includes an SV40 origin of replication to enhance gene expression. Other viral replication systems can also be used; for example, EBV origin and EBNA or BPV are useful as disclosed herein.

A preferred *E. coli* strain in which to propagate phagemids is the *E. coli* host strain DH5αF'. Useful systems according to the present invention may further benefit from the use of helper bacteriophage. For example, the M13 helper M13K07 is particularly useful in conjunction with the aforementioned bacterial strains.

Methods of preparing phagemid particles are known in the art and may appropriately be modified depending on the system utilized, as those of skill in the art will appreciate. (See, e.g., Sambrook et al., *Molecular Cloning: A Laboratory Manual*, Cold Spring Harbor Press, 1989; Rider et al., in *Phage Display of Peptides and Proteins: A Laboratory Manual*, Academic Press, 1996).

III. Construction of Ligand-Modified Bacteriophage

A variety of constructs and methods may readily be adapted for use in the linking of a phage to a ligand for use in the specific targeting and delivery of a therapeutic moiety or agent. Thus, phage present a ligand that is part of a fusion protein, direct chemical linkage, or by sandwich. Exemplary methods for modifying bacteriophage to present ligands are described below. Ligands are prepared as discussed herein by any suitable method, including recombinant DNA technology, isolation from a suitable source, purchase from a commercial source, or chemical synthesis. Various preferred methods and modifications to ligands that may facilitate the linkage between the ligand and the phage protein are disclosed in published PCT Publication No. WO 96/36362.

For example, DNA encoding the polypeptide ligands may be isolated, synthesized or obtained from commercial sources or prepared as described herein. Expression of recombinant polypeptides may be performed as described herein; and DNA encoding these polypeptides may be used as the starting materials for the methods herein. DNA may be prepared synthetically based on the amino acid or DNA sequence or may be isolated using methods known to those of skill in the art, such as PCR, probe hybridization of libraries, and the like or obtained from commercial or other sources.

A. Generation of Fusion Proteins

Fusion proteins of the present invention preferably comprise a gene encoding all or a receptor-binding polypeptide portion of a ligand (e.g., FGF2) genetically fused or linked to the coat protein-encoding gene of a bacteriophage particle using methods known to those of skill in the art (see, e.g., Smith and Scott *Meth Enymol*, 217:228–257, 1993; Kay et al., *Phage Display of Peptides and Proteins: A Laboratory Manual*, Academic Press, 1996). Preferably, the phage is a filamentous phage; M13 is described herein as an exemplary preferred embodiment. Preparation of a fusion protein comprising M13 gene III or VIII coat protein is described herein.

It should also be noted that it is preferred that, when the phage vectors are assembled, ligand-phage coat fusion proteins are the predominant species. Generally, the copy number of ligand-phage coat fusions relative to wild type coat protein may be readily controlled by displaying the fusion at high copy number (type 3 or type 8 vectors) or at low copy number (type 3+3 or type 8+8 vectors).

Nucleotide sequences for the ligands are readily available (e.g., from GenBank) or may be synthesized or isolated by standard techniques. The ligand coding regions are inserted into the phage vectors using well-known methods.

Nucleotide sequences encoding ligand-phage fusions may also be further modified via the insertion of a mammalian reporter gene, in order to further verify binding and internalization, as well as expression of the nucleic acid payload. One exemplary mammalian reporter gene is EGFP; others include the sequences for β-galactosidase, luciferase, human growth hormone (HGH), and secreted alkaline phosphatase. Methods of preparing and using such sequences as described herein are known to those of skill in the art. (See, e.g., Sambrook et al., *Molecular Cloning: A Laboratory Manual*, Cold Spring Harbor Press, 1989.)

In various preferred embodiments, the expression cassette also includes an origin of replication. The SV40 ori is particularly useful for generating high copy number replication in cell lines containing T antigen (e.g., COS cells). A variety of useful methods and protocols are available which employ this and other origins of replication (see, e.g., Sambrook et al., Id).

Ligand-coat protein fusions may be tested for phage binding to the relevant receptor (e.g. a cognate receptor to the ligand) via known methods such as ELISA. Binding and internalization of the fusion is readily assayed via art-recognized methods such as immunohistochemistry (Barry et al., *Nature Med.* 2: 299–305, 1996; Li, *Nature Biotech.* 15: 559–563, 1997).

The modified phage may further be tested for transduction of the reporter gene into the cells—preferably mammalian cells—by adding the phage to the cell cultures for a predetermined amount of time; depending on the protocol and reporter used, the number of cells expressing the reporter gene product at a subsequent, predetermined time is readily assessed using known methods. For example, if the reporter gene is EGFP, which is translated into green fluorescent protein (GFP) when gene delivery and expression occur, one may readily measure the number of autofluorescing cells several hours later. Results are readily quantitated. For example, if fluorescent reporters are used, flow cytometry is particularly useful to measure the distribution of cells expressing the fluorescent reporter gene in the population and by fluorometry of cell extracts to measure total amounts of reporter protein expressed.

A variation of the aforementioned procedure involves the construction of a fusion protein including all or a portion of an antibody molecule and a phage protein—thereby producing a phage protein-antibody conjugate. Although preparation of a single-chain antibody-phage coat protein fusion is described as exemplary, other antibodies and fragments thereof are also useful as disclosed.

In general, an antibody or portion thereof—e.g., a mAb, Fab, or ScFv—is either prepared via direct synthesis (e.g., using splice site overlap extension PCR, with the optional addition of restriction sites at the 5' and 3' ends of the sequence) or it is selected and isolated from ascites and is thereafter purified via known methods, such as affinity chromatography. If only the Fab fragment is to be used, an antibody harvested from the ascites is further modified according to standard protocols to produce the Fab—e.g., through the use of papain digestion.

One exemplary antibody which specifically targets the FGF receptor is the 11A8 antibody derived from the 11A8 hybridoma. 11A8 recognizes ECDR1 by Western blot, can immunoprecipitate FGFRs from extracts of SK-HEP-1 and SK-MEL-28, a melanoma cell. Antibody 11A8 also stains SK-HEP-1 cells on the cell surface. Receptor-binding fragments and variants of 11A8 and similar, receptor-binding antibodies—preferably, antibodies that also internalize—may also be non-covalently (or covalently) attached to the phage coat in order that they may function as useful ligands, as described herein. Other antibodies (and fragments thereof) that specifically target cellular receptors, preferably those antibodies and fragments thereof that bind and internalize may be identified and synthesized according to the methods disclosed herein and via use of other methods described in the art.

Amplified heavy and light chain product is cloned into the expression vector. The expression vector chosen preferably contains appropriate promoters and convenient restriction sites, as well. The resultant protein may optionally be expressed as both N-terminal and C-terminal fusion protein. In addition, flexible linkers may be added between the antibody and the ligand to help favor proper protein folding. Use of smaller antibody fragments—e.g. Fab or ScFv—likely facilitates folding even further. The expression, purification and evaluation of antibody-phage fusion proteins is readily accomplished in host cells—e.g., in bacteria—using known protocols.

Alternatively, one may fuse two monospecific antibodies or immunologically active portions thereof with different phage coat proteins, wherein each antibody is directed against the same receptor, or against different receptors. Such a construct may be useful in situations in which the expressed cellular receptors are polymorphic and the use of phage vectors targeted to two or more of said polymorphisms would have a higher likelihood of delivering payload to the desired cells. Preparation of a fusion between phage coat protein and bispecific antibodies is also within the scope of the present invention.

As a result, gene delivery vectors targeted to one or more receptors may readily be prepared according to the within-disclosed methods. Alternatively, the fused antibody portion(s) are directed to other ligands as opposed to specific receptors, rather than targeting the antibody/ies to the relevant receptors directly. Such a procedure may be particularly useful in situations in which a ligand's ability to bind its cognate receptor is dependent upon the ability of the ligand to attain a specific secondary or tertiary structure that would not be readily achievable if the ligand were incorporated into a ligand-phage fusion protein.

For example, chimeric antibodies including receptor-binding ligands in place of their constant region, such as those described in published PCT Publication No. WO 91/14438 are useful as disclosed herein. Moreover, bispecific antibodies generated as described in published UK Patent App. No. GB 2197323, are also preferred for use as described herein. Further, bridging antibodies such as those described in published PCT Publication No. WO 92/08801 may be useful in the treatment of conditions in which a "timed-release" of therapeutic nucleotide sequences is desired. Thus, use of bispecific antibodies which link the phage vector to the target cell pending the co- or subsequent administration of vectors carrying highly specific proteases, ribozymes or deoxyribozymes that release the bound vectors, thereby freeing them to bind directly to their targeted receptor and internalize the vector, is also contemplated within the scope of the present invention.

To be useful in targeting bacteriophage vectors, the recombinant fusion protein must bind the cognate receptor. Fusion proteins may be analyzed for their binding capacity in an ELISA, according to known techniques. To test the functionality of the receptor binding domain, binding and internalization assays may be performed on receptor-positive cells and binding specificity is determined by including unlabeled fusion protein as a competitor per standard protocols.

In one exemplary method, internalization of a fusion protein is determined by pre-incubating receptor-positive cells with labeled fusion protein, washing cells to remove unbound labeled protein, and conducting further incubations at predetermined temperatures and for various time intervals to allow receptor internalization. Following the removal of surface-bound radiolabeled protein, cells are lysed and radioactivity is determined in the cell lysate. The analysis will determine the capacity of the fusion protein to bind its cognate receptor in the context of a fusion protein.

In order to facilitate the attachment of a ligand sequence to a phage sequence, the phage protein may be modified at the molecular level. Thus, a nucleotide sequence encoding a therapeutic molecule, toxin, or other regulatory molecule may be operatively linked for expression to a phage nucleotide sequence—particularly to a sequence encoding a structural protein. For example, protein III or protein VIII of filamentous phage (e.g. M13) may be modified via attachment of a heterologous nucleotide sequence to the C-terminus of the gene encoding said protein. Alternatively, one or more heterologous sequences may be inserted at an internal site—i.e., within the phage coat protein sequence. Various methods of preparing such fusions are available in the art and are contemplated by the present invention.

Finally, it should also be appreciated that phage proteins may be modified via means that are not precisely "immunologic" or "genetic." Modification of phage proteins via means other than those exemplified herein is fully within the scope of the present invention. For example, useful filamentous phage-based vectors of the present invention may undergo chemical alteration of their coat proteins, e.g., in a manner that affects the vector's immunogenicity, in order to regulate the uptake and persistence of the vector in the cells of an individual to whom the within-disclosed therapeutic constructs and compositions are administered. Methods of making such alterations to proteins via chemical and physical means (e.g. heat shock) are known to those of skill in the art and may readily be ascertained in the relevant literature.

B. Use of Antibodies to Link Vector and Ligand

A variation of the procedures recited above, which are directed toward the preparation of fusion proteins, is the use of bispecific antibodies or fragments thereof—e.g., in the form of bispecific ScFv's—to target a phage to a particular cellular receptor, using an antibody or portion thereof that is raised against phage coat protein and linking that antibody to one that has been raised against a ligand. Although this is not quite the same as the construction of a fusion protein, various techniques summarized above (e.g. with respect to the preparation of an ScFv) are useful in preparing bispecific antibodies for use as described herein.

In another embodiment, a fusion protein comprising phage coat protein and a monospecific antibody is useful in linking a phage vector to a ligand. Preparation of an antibody or fragment thereof is readily understood in the art; also see Section A above. The antibody portion of the antibody-fusion protein is preferably raised against a preselected ligand—e.g., one which is not easily incorporated into a fusion protein, perhaps due to conformational difficulties. Such an antibody-phage coat fusion may then be-utilized to bind a ligand that targets a specific receptor to the phage vector, for the purpose of delivering a payload to a cell expressing the relevant cognate receptor.

C. Use of Avidin-Biotin to Link Bacteriophage to Ligand

One method for targeting the phage to cellular receptors is to link the phage to the ligand via avidin-biotin, which may be performed essentially as follows. A ligand-phage complex is assembled in the presence of test cells at 0° C., and followed by incubation at 37° C. to allow internalization. A ligand molecule is conjugated to biotin at the single free sulfhydryl group using biotin-BMCC (Pierce; Rockford, Ill.) according to the manufacturer's suggested protocol. Unreacted biotin is removed by passing the reaction over a PD-10 desalting column.

Cultured cells—e.g., COS cells—are incubated for a predetermined time period (e.g., 24 hours) prior to phage addition. Cells are washed and biotinylated ligand is added (often on ice) thereafter, and the preparation is incubated for a predetermined period of time. Avidin (e.g. Neutravidin, a neutral carbohydrate-stripped avidin; Pierce, Rockford, Ill.) is added and the cell wash is repeated. Biotinylated anti-phage antibody—such as anti-M13 antibody, when the phage is M13—is then added and incubated for a predetermined time period. The cell wash is then repeated and a sufficient quantity of colony forming units are added to each receptacle or well, followed by further incubation, preferably on ice. The cells are washed again, resuspended in fresh media and are allowed to incubate further for an appropriate period of time and at a predetermined temperature. Expression of the agent encoded by the therapeutic nucleic acid sequence transported by the phage vector is thereafter monitored. In various preferred embodiments, the vector further comprises a reporter gene, such as EGFP, which may readily be monitored via fluorescence microscopy or via a fluorescence activated cell sorter (FACS), according to standard techniques.

D. Covalent Linkages/Chemical Conjugation

1. Linkage of Ligands to Bacteriophage Using Polycations

A ligand may alternatively be linked to a polycation such as polylysine, which then binds to phagemid particles as a result of the interaction between the positively-charged polycation and negatively-charged phage. In one exemplary procedure, a ligand is covalently linked to polylysine using S-2-pyridyl disulfide (SPDP) according to known protocols (see, e.g., Sosnowski et al. *J. Biol. Chem.* 271: 33647–33653, 1996). Phagemid particles are then mixed with ligand-polylysine or polylysine alone and allowed to stand at room temperature for a predetermined period of time prior to testing the conjugates in cultured cells, or prior to ex vivo or in vivo administration. In order to verify expression, a reporter sequence may be included in the ligand-polylysine-phage construct; fluorescent markers such as GFP and fluorescein are particularly useful for in vitro assays.

In the context of an assay procedure, the treated cells are examined by conventional means—e.g. fluorescent microscopy or FACS. If the reporter sequence is EGFP, autofluorescent GFP positive cells are then counted in order to confirm that the GFP gene (and nucleotide sequences appended thereto) has been successfully transduced into the cells via phage linked to the ligand via polylysine. This method of phage transduction is an attractive alternative to the use of the avidin-biotin system described herein.

2. Linkage of Ligands to Bacteriophage Using Crosslinking Reagents

The coat proteins of a bacteriophage, preferably a filamentous bacteriophage, may be conjugated directly to a ligand using heterobifunctional crosslinking reagents. For example, a free lysine at the N-terminus of the gene VIII coat protein of M13 phage is available for chemical modification (Armstrong et al, *EMBO J.* 2: 1641–1646, 1983) and may conveniently be employed for that purpose. In general, the procedure may be described as follows.

Phage particles are first thiolated—e.g., via the addition of SPDP—for a predetermined period of time and at a predetermined temperature. Unreacted reagent is removed; the ligand is then reacted with thiolated phage. Free ligand is removed, and the phage linked to the ligand are further purified according to standard protocols. In similar procedures, N-succinimidyl S-acetylthioacetate (SATA) and other suitable heterobifunctional chemical reagents may be used to introduce the thiol function, rather than SPDP, pursuant to art-recognized methods. For example, the selected linker or linkers is (are) linked to the receptor-binding internalized ligands by chemical reaction, generally relying on an available thiol or amine group on the receptor-binding internalized ligands. Heterobifunctional linkers are particularly suited for chemical conjugation and include such molecules as m-maleimidobenzoyl-N-hydroxysulfosuccinimide ester, N-succinimidyl-(4-iodoacetyl)amino-benzoate, and N-succinimidyl-3-(2-pyridyldithio)propionate. (See, e.g., published UK Pat. App. Nos. GB 2268492, 2253626, and 2257431, the disclosures of which are incorporated by reference herein.)

The linkage of a ligand to phage protein is readily confirmed by polyacrylamide gel electrophoresis and immunoblotting of phage proteins. For example, under non-reducing conditions, the ligand-modified gene VIII protein is shifted from its apparent molecular mass in unlinked form to a significantly greater apparent molecular mass when linkage has been successful. The addition of reducing agent to the sample buffer disrupts the disulfide linkage and yields free ligand and gene VIII protein.

The chemically modified ligand-phage constructs may then be assayed for their ability to transduce mammalian cells. Ligand-modified phagemid particles bearing an expression cassette containing a promoter and a reporter sequence are added to plated cells in multiwell plates, for example. The cells are assayed for marker protein expression at a predetermined interval following the addition of the ligand-phage constructs.

3. Additional Linking Methods

Another means of chemically linking a ligand to a phage particle comprises the expression of a specific reactive moiety on the surface of a phage particle, wherein that moiety is then conjugated specifically and directly to the selected ligand. Examples of reactive moieties that may readily be engineered into the surface protein of a phage particle include various binding proteins, protein A, cysteine, and a wide variety of reactive groups, to name but a few examples. (See, e.g, published UK Pat. App. Nos. GB 2268492 and 2257431, the disclosures of which are incorporated herein by reference.)

Methods of engineering such moieties onto the surface of a phage particle are available in the art and have also been disclosed in preceding sections. For example, site-specific mutagenesis techniques may be utilized to alter the amino acid residue sequence of the phage coat protein, thereby facilitating the binding of a ligand to the relevant site(s). Thereafter, the preselected ligand (e.g. a polypeptide that binds an FGF receptor) is conjugated to the phage surface via the reactive moiety. In addition to FGFR-binding polypeptides, other useful ligands which may be conjugated to the phage particle surface include antibodies and fragments thereof (e.g. 11A8), including single-chain antibodies, and cysteine, to name a few examples.

Still other ligands can be attached to the phage surface coat proteins. The size of fusions to coat proteins can be small as in small random peptides of 6 (Scott and Smith, *Science*, 249: 386–390, 1990) to 38 amino acids (Kay, *Gene* 128: 59–65, 1993) in length from which peptides that bind cell surface receptors have been isolated. Protein molecules such as antibody Fab fragments (~50 kDa) have also been fused to phage coat proteins. Whole proteins such as alkaline phosphatase, bovine pancreas trypsin inhibitor, trypsin, β lactamase, cytokine IL3 and glutathione-S-transferase, PDGF receptor (Chiswell and McCafferty, *Trends Biotechnol.* 10: 80, 1992) and IgE ectodomain (Robertson, *J. Biol. Chem.* 268: 12736, 1993) have also been fused to surface of phage. For an up-to-date reference list of proteins displayed on phage, see www.unc.edu/depts/biology/bkay/phagedisplay/html. The expression of small peptides on the phage surface is highly efficient whereas large peptides are expressed from about 50 copies to less than 1 copy per phage.

E. Propagation of Modified Phage

Modified phage are propagated as described by Sambrook et al. Suitable host bacteria that carry the F' episome are grown from an isolated colony to mid-log phase growth. Bacteriophage isolates can be picked from plaques that form on a lawn of infected host cells grown on semi-solid medium. The turbid plaques are slower growing infected cells that are visible to the naked eye against a lawn of more dense uninfected bacteria. Phage stocks can be prepared in liquid culture from well isolated plaques. About ⅒ of the phage from a single plaque are used to infect 50 μl of host bacteria in 2 ml of medium. The culture is incubated at 37° C. for 5–6 hours at constant agitation. Longer incubation times are avoided to prevent deletion mutants. The bacteria are pelleted by microcentrifugation and the supernatant transferred to a fresh tube. The titer of the phage in the supernatant should be about $10^{12}$ pfu/ml and can be stored at 4° C. or indefinitely at −20° C.

IV. Tranducing Genes

A transducing gene, as used herein, refers to a gene which encodes a detectable product in the target cell. Preferentially, the transducing gene is a therapeutic gene. A "therapeutic nucleic acid" or "therapeutic gene" describes any nucleic acid molecule used in the context of the invention that effects a treatment, generally by modifying gene transcription or translation. It includes, but is not limited to, the following types of nucleic acids: nucleic acids encoding a protein, ribozyme, antisense nucleic acid, DNA intended to form triplex molecules, protein binding nucleic acids, and small nucleotide molecules. As such, the product of the therapeutic gene may be DNA or RNA. These genes sequences may be naturally-derived sequences or recombinantly derived. A therapeutic nucleic acid may be used to effect genetic therapy by serving as a replacement for a defective gene, by encoding a therapeutic product, such as TNF, or by encoding a cytotoxic molecule, especially an enzyme, such as saporin. The therapeutic nucleic acid may encode all or a portion of a gene, and may function by recombining with DNA already present in a cell, thereby replacing a defective portion of a gene. It may also encode a portion of a protein and exert its effect by virtue of co-suppression of a gene product.

As discussed above, the therapeutic gene is provided in operative linkage with a selected promoter, and optionally in operative linkage with other elements that participate in transcription, translation, localization, stability and the like.

The therapeutic nucleotide composition of the present invention is from about 20 base pairs to about 100,000 base pairs in length. Preferably the nucleic acid molecule is from about 50 base pairs to about 50,000 base pairs in length. More preferably the nucleic acid molecule is from about 50 base pairs to about 10,000 base pairs in length. Even more preferably, it is a nucleic acid molecule from about 50 pairs to about 4,000 base pairs in length.

Such nucleic acid compositions may be delivered by the bacteriophage of this invention by a variety of methods including, for example, in vitro, in vivo, and ex vivo transduction methodologies.

A. Gene Replacement or Enhancement

Nucleic acids for delivery also include DNA molecules that encode proteins to replace defective genes or provide factors to combat certain diseases or syndromes. Many genetic defects are caused by a mutation in a single gene. Introduction of the wild-type gene will serve to alleviate the deficiency or genetic abnormality. Such genes include HPRT, adenosine deaminase, LDL receptor, Factor IX, Factor VIII, growth hormone, von Willebrand factor, PTH (parathyroid hormone), M-CSF, TGF-β, PDGF, VEGF, FGF, IGF, BMP (bone morphogenic protein), collagen type VII, fibrillin, Insulin, cystic fibrosis transmembrane conductance regulator, adenosine deaminase, and the like.

For example, in ischemia, endothelial and smooth muscle cells fail to proliferate. A construct that expresses FGF, alone or in combination with FGF protein to give short-term relief and induce FGF receptor, can be used to combat effects of ischemia. In such a case, FGF gene with a leader sequence to promote secretion is preferable. As well, the FGF gene is preferably driven by a constitutive promoter.

In addition, certain angiogenic diseases suffer from a paucity of angiogenic factor and thus be deficient in microvessels. Certain aspects of reproduction, such as ovulation, repair of the uterus after menstruation, and placenta development depend on angiogenesis. For reproductive disorders with underlying angiogenic dysfunction, a construct that expresses FGF, VEGF, or other angiogenic factors, may be beneficial.

Cytokine immunotherapy is a modification of immunogene therapy and involves the administration of tumor cell vaccines that are genetically modified ex vivo or in vivo to express various cytokine genes. In animal tumor models, cytokine gene transfer resulted in significant antitumor immune response (Fearon, et al., *Cell* 60: 387–403, 1990; Wantanabe, et al., *Proc. Nat. Acad. Sci.* USA, 86: 9456–9460, 1989). Thus, in the present invention, the phages are used to deliver DNA encoding a cytokine, such as IL-12, IL-10, IL-2, GM-CSF, INF-γ, or an MHC gene, such as HLA-B7. Delivery of these genes will modulate the immune system, increasing the potential for host antitumor immunity. Alternatively, DNA encoding co-stimulatory molecules, such as B7.1 and B7.2, ligands for CD28 and CTLA-4 respectively, can also be delivered to enhance T cell mediated immunity. These genes can be co-delivered with cytokine genes, using the same or different promoters and optionally with an internal ribosome binding site. Similiarly, α-1,3-galactosyl transferase expression on tumor cells allows complement-mediated cell killing.

As well, acquired or complex multispecific diseases, such as renal failure-induced erythropoietin deficiency, Parkinson's disease (dopamine deficiency), adrenal insufficiency, immune deficiencies, cyclic neutropenia, could be treated using a therapeutic gene delivered by a ligand. In some cases, vascular growth is desirable. As smooth muscle cells underlie the vasculature, delivery of endothelial growth factors, such as FGFs, especially FGF-2, VEGF, tie1, and tie2, through smooth muscle cells is advantageous.

B. Genes Encoding Protein Cytocides (Including Prodrugs)

A cytocide-encoding agent is a nucleic acid molecule (e.g., DNA or RNA) that, upon internalization by a cell, and subsequent transcription (if DNA) and[/or] translation into a product is cytotoxic or cytostatic to a cell, for example, by inhibiting cell growth through interference with protein synthesis or through disruption of the cell cycle. Such a product may act by cleaving rRNA or ribonucleoprotein, inhibiting an elongation factor, cleaving mRNA, or other mechanism that reduces protein synthesis to a level such that the cell cannot survive. The product may be a protein, ribozyme, deoxyribozyme, antisense, and the like.

Examples of suitable products include, without limitation, saporin, the ricins, abrin, other ribosome inactivating proteins (RIPs), *Pseudomonas* exotoxin, inhibitors of DNA, RNA or protein synthesis, antisense nucleic acids, other metabolic inhibitors (e.g., DNA cleaving molecules), prodrugs (e.g., thymidine kinase from HSV and bacterial cytosine deaminase), light-activated porphyrin, ricin, ricin A chain, maize RIP, gelonin, diphtheria toxin, diphtheria toxin A chain, trichosanthin, tritin, pokeweed antiviral protein (PAP), mirabilis antiviral protein (MAP), Dianthins 32 and 30, abrin, monordin, bryodin, shiga, a catalytic inhibitor of protein biosynthesis from cucumber seeds (see, e.g., WO 93/24620), *Pseudomonas* exotoxin, biologically active fragments of cytotoxins and others known to those of skill in this art.

DNA molecules that encode an enzyme that results in cell death or renders a cell susceptible to cell death upon the addition of another product are preferred. Ribosome-inactivating proteins (RIPs), which include ricin, abrin, and saporin, are plant proteins that catalytically inactivate eukaryotic ribosomes. Ribosome-inactivating proteins inactivate ribosomes by interfering with the protein elongation step of protein synthesis. For example, the ribosome-inactivating protein saporin is an enzyme that cleaves rRNA and inhibits protein synthesis. Other enzymes that inhibit protein synthesis are especially well suited for use in the present invention. Any of these proteins, if not derived from mammalian sources, may use mammalian-preferred codons. Preferred codon usage is exemplified in *Current Protocols in Molecular Biology*, infra, and Zhang et al. (*Gene* 105:61, 1991).

A nucleic acid molecule encoding a prodrug may alternatively be used within the context of the present invention. Prodrugs are inactive in the host cell until either a substrate or an activating molecule is provided. As used herein, a "prodrug" is a compound that metabolizes or otherwise converts an inactive, nontoxic compound to a biologically, pharmaceutically, therapeutically, of toxic active form of the compound or is modified upon administration to yield an active compound through metabolic or other processes. Most typically, a prodrug activates a compound with little or no cytotoxicity into a toxic compound. Two of the more often used prodrug molecules, both of which are suitable for use in the present invention, are HSV thymidine kinase and *E. coli* cytosine deaminase.

Briefly, a wide variety of gene products which either directly or indirectly activate a compound with little or no cytotoxicity into a toxic product may be utilized within the context of the present invention. Representative examples of such gene products include HSVTK (herpes simplex virus thymidine kinase) and VZVTK (varicella zoster virus thymidine kinase), which selectively phosphorylate certain purine arabinosides and substituted pyrimidine compounds. Phosphorylation converts these compounds to metabolites that are cytotoxic or cytostatic. For example, exposure of the drugs gancyclovir, acyclovir, or any of their analogues (e.g., FIAU, FIAC, DHPG) to cells expressing HSVTK allows conversion of the drug into its corresponding active nucleotide triphosphate form.

Other gene products that may be utilized within the context of the present invention include *E. coli* guanine phosphoribosyl transferase, which converts thioxanthine into toxic thioxanthine monophosphate (Besnard et al., *Mol. Cell. Biol.* 7:4139–4141, 1987); alkaline phosphatase, which converts inactive phosphorylated compounds such as mitomycin phosphate and doxorubicin-phosphate to toxic dephosphorylated compounds; fungal (e.g., *Fusarium oxysporum*) or bacterial cytosine deaminase, which converts 5-fluorocytosine to the toxic compound 5-fluorouracil (Mullen, *PNAS* 89:33, 1992); carboxypeptidase G2, which cleaves glutamic acid from para-N-bis (2-chloroethyl) aminobenzoyl glutamic acid, thereby creating a toxic benzoic acid mustard; and Penicillin-V amidase, which converts phenoxyacetabide derivatives of doxorubicin and melphalan to toxic compounds (see generally, Vrudhula et al., *J. of Med. Chem.* 36(7):919–923, 1993; Kern et al., *Canc. Immun. Immunother.* 31(4):202–206, 1990). Moreover, a wide variety of Herpesviridae thymidine kinases, including both primate and non-primate herpes viruses, are suitable. Such herpes viruses include Herpes Simplex Virus Type 1 (McKnight et al., *Nuc. Acids Res* 8:5949–5964, 1980), Herpes Simplex Virus Type 2 (Swain and Galloway, *J. Virol.*

46:1045–1050, 1983), Varicella Zoster Virus (Davison and Scott, *J. Gen. Virol.* 67:1759–1816, 1986), marmoset herpes virus (Otsuka and Kit, *Virology* 135:316–330, 1984), feline herpes virus type 1 (Nunberg et al., *J. Virol.* 63:3240–3249, 1989), pseudorabies virus (Kit and Kit, U.S. Pat. No. 4,514, 497, 1985), equine herpes virus type 1 (Robertson and Whalley, *Nuc. Acids Res.* 16:11303–11317, 1988), bovine herpes virus type 1 (Mittal and Field, *J. Virol.* 70:2901–2918, 1989), turkey herpes virus (Martin et al., *J. Virol.* 63:2847–2852, 1989), Marek's disease virus (Scott et al., *J. Gen. Virol.* 70:3055–3065, 1989), herpes virus saimiri (Honess et al., *J. Gen. Virol.* 70:3003–3013, 1989) and Epstein-Barr virus (Baer et al., *Nature* (London) 310:207–311, 1984). Such herpes viruses may be readily obtained from commercial sources such as the American Type Culture Collection ("ATCC"; Manassas, Va.).

Furthermore, as indicated above, a wide variety of inactive precursors may be converted into active inhibitors. For example, thymidine kinase can phosphorylate nucleosides (e.g., dT) and nucleoside analogues such as ganciclovir (9-{[2-hydroxy-1-(hydroxymethyl)ethoxy] methyl} guanosine), famciclovir, buciclovir, penciclovir, valciclovir, acyclovir (9-[2-hydroxy ethoxy)methyl] guanosine), trifluorothymidine, 1-[2-deoxy, 2-fluoro, beta-D-arabino furanosyl]-5-iodouracil, ara-A (adenosine arabinoside, vivarabine), 1-beta-D-arabinofuranoxyl thymine, 5-ethyl-2'-deoxyuridine, 5-iodo-5'-amino-2,5'-dideoxyuridine, idoxuridine (5-iodo-2'-deoxyuridine), AZT (3' azido-3' thymidine), ddC (dideoxycytidine), AIU (5-iodo-5' amino 2', 5'-dideoxyuridine) and AraC (cytidine arabinoside). Other gene products may render a cell susceptible to toxic agents. Such products include tumor necrosis factor, viral proteins, and channel proteins that transport drugs.

Moreover, a cytocide-encoding agent may be constructed as a prodrug, which when expressed in the proper cell type is processed or modified to an active form. For example, the saporin gene may be constructed with an N- or C-terminal extension containing a protease-sensitive site. The extension renders the initially translated protein inactive and subsequent cleavage in a cell expressing the appropriate protease restores enzymatic activity.

The DNA sequences of these products are well known (see GenBank). A nucleic acid molecule encoding one of the may be isolated by standard methods, such as amplification (e.g., PCR), probe hybridization of genomic or cDNA libraries, antibody screenings of expression libraries, chemically synthesized or obtained from commercial or other sources.

Additional types of cytocides that may be delivered according to the methods of the present invention are antibody molecules that are preferably expressed within the target cell; hence, these antibody molecules have been given the name "intrabodies." Conventional methods of antibody preparation and sequencing are useful in the preparation of intrabodies and the nucleic acid sequences encoding same; it is the site of action of intrabodies that confers particular novelty on such molecules. (For a review of various methods and compositions useful in the modulation of protein function in cells via the use of intrabodies, see published International Application No. WO 96/07321.)

Intrabodies are antibodies and antibody derivatives (including single-chain antibodies or "SCA") introduced into cells as transgenes that bind to and incapacitate an intracellular protein in the cell that expresses the antibodies. As used herein, intrabodies encompass monoclonals, single chain antibodies, V regions, and the like, as long they bind to the target protein. Intrabodies to proteins involved in cell replication, tumorigenesis, and the like (e.g., HER2/neu, VEGF, VEGF receptor, FGF receptor, FGF) are especially useful.

For example, antibodies to HER2/neu (also called erbB-2) may be used to inhibit the function of this protein. HER2/neu has a pivotal role in the progression of certain tumors, human breast, ovarian and non-small lung carcinoma. Thus, inhibiting the function of HER2/neu may result in slowing or halting tumor growth (see, e.g. U.S. Pat. No. 5,587,458.) In view of the fact that HER2/neu is a receptor protein, it may also function as the "target" of an antibody conjugated to the surface of a phage particle, as further described elsewhere in this specification.

C. Antisense and Ribozymes

The conjugates provided herein may also be used to deliver a ribozyme, antisense, and the like to targeted cells. Such products include antisense RNA, antisense DNA, ribozymes, deoxyribozymes, triplex-forming oligonucleotides, and oligonucleotides that bind proteins. The nucleic acids can also include RNA trafficking signals, such as viral packaging sequences (see e.g., Sullenger et al. *Science* 262:1566, 1994).

Nucleic acids and oligonucleotides for use as described herein can be synthesized by any method known to those of skill in this art (see, e.g., WO 93/01286, U.S. application Ser. No. 07/723,454; U.S. Pat. Nos. 5,218,088; 5,175,269; 5,109,124). Identification of oligonucleotides and ribozymes for use as antisense agents and DNA encoding genes for targeted delivery for genetic therapy involve methods well known in the art. For example, the desirable properties, lengths and other characteristics of such oligonucleotides are well known. Antisense oligonucleotides may be designed to resist degradation by endogenous nucleolytic enzymes using linkages such as phosphorothioate, methylphosphonate, sulfone, sulfate, ketyl, phosphorodithioate, phosphoramidate, phosphate esters, and the like (see, e.g., Stein in: *Oligodeoxynucleotides. Antisense Inhibitors of Gene Expression*, Cohen, Ed, Macmillan Press, London, pp. 97–117, 1989); Jager et al., *Biochemistry* 27:7237, 1988).

Antisense nucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. Nos. 5,168,053; 5,190,931; 5,135,917; 5,087,617). Triplex molecules refer to single DNA strands that bind duplex DNA forming a co-linear triplex molecule, thereby preventing transcription (see, e.g., U.S. Pat. No. 5,176,996).

Particularly useful antisense nucleotides and triplex molecules are molecules that are complementary or bind to the sense strand of DNA or mRNA that encodes a protein involved in cell proliferation, such as an oncogene or growth factor, (e.g., bFGF, int-2, hst-1/K-FGF, FGF-5, hst-2/FGF-6, FGF-8). Other useful antisense oligonucleotides include those that are specific for IL-8 (see, e.g., U.S. Pat. No. 5,241,049), c-src, c-fos H-ras (lung cancer), K-ras (breast cancer), urokinase (melanoma), BCL2 (T-cell lymphoma), IGF-1 (glioblastoma), IGF-1 receptor (glioblastoma), TGF-β1, and CRIPTO EGF receptor (colon cancer). These particular antisense plasmids reduce tumorigenicity in athymic and syngeneic mice.

A ribozyme is an RNA molecule that specifically cleaves RNA substrates, such as mRNA, resulting in inhibition or interference with cell growth or expression. There are at least five known classes of ribozymes involved in the cleavage and/or ligation of RNA chains. Ribozymes can be targeted to any RNA transcript and can catalytically cleave that transcript (see, e.g., U.S. Pat. No. 5,272,262; U.S. Pat. No. 5,144,019; and U.S. Pat. Nos. 5,168,053, 5,180,818, 5,116,742 and 5,093,246).

In addition, inhibitors of inducible nitric oxide synthase (NOS) and endothelial nitic oxide synthase are cytocides that are useful for delivery to cells. Nitric oxide (NO) is implicated to be involved in the regulation of vascular growth and tone in arterosclerosis. NO is formed from L-arginine by nitric oxide synthase (NOS) and modulates immune, inflammatory and cardiovascular responses.

As described elsewhere herein, the phage vectors of the present invention may be used to deliver a variety of therapeutic sequences to target cells. In various embodiments, the therapeutic sequences encode or comprise enzymatic DNA and/or RNA molecules that are able to cleave other nucleic acid molecules, including DNA molecules, RNA molecules, and hybrids thereof. Thus, expression vectors useful in such embodiments are also contemplated herein. (See, e.g., Published International Application Nos. WO 92/06693, WO 96/17086, and WO 95/31551; and U.S. Pat. Nos. 4,987,071, 5,580,967 and 5,595,873, the disclosures of which are incorporated by reference herein.)

Briefly, using enzymatic RNA molecules ("ribozymes") as an example, a method of forming an enzymatic RNA molecule expression vector includes providing a vector comprising nucleic acid encoding a first ribozyme and providing a single-stranded DNA molecule encoding a second ribozyme. The single-stranded DNA is then allowed to anneal to form a partial duplex DNA which can be filled in by treatment with an appropriate enzyme, such as a DNA polymerase in the presence of dNTPs, to form a duplex DNA which can then be ligated to the vector.

Large vectors resulting from use of this method can then be selected to insure that a high copy number of the single-stranded DNA encoding the second enzymatic RNA molecule is incorporated into the vector. Suitable restriction endonuclease sites may also be provided to ease the construction of such a vector in DNA vectors or in requisite DNA vectors of an RNA expression system.

The present invention also features expression vectors including a nucleic acid segment encoding an enzymatic DNA or RNA molecule, preferably in a manner which allows expression of that NA molecule within a target cell. Thus, in general, an expression vector useful in conjunction with ribozymes or deoxyribozymes includes a bacterial, viral or eukaryotic promoter within a plasmid, cosmid, phagemid, virus, viroid, or phage vector. Other suitable vectors include double-stranded DNA (dsDNA), partially double-stranded DNA, dsRNA, partially dsRNA, or single-stranded RNA (ssRNA) or DNA (ssDNA). It should also be appreciated that useful vectors according to the present invention need not be circular.

It is also preferred that an enzymatic NA molecule-encoding nucleotide sequence is transcriptionally linked to a promoter sequence. For example, a vector according to the present invention may comprise an enzymatic RNA molecule under the control of a viral promoter, such as an Epstein-Barr Virus (EBV) promoter. A variety of viral promoters useful for this purpose are known in the art; see, eg., those described in published PCT Application No. WO 93/23569, the disclosures of which are incorporated by reference herein.

In another variation, one or more additional enzymatic RNA molecule-encoding nucleotide sequences are also included in the vector; said additional enzymatic RNA molecule-encoding sequences may be located on either side, or both sides, of a nucleotide sequence encoding the first enzymatic RNA molecule. Preferably, there are intervening nucleotides or nucleotide sequences between successive enzymatic RNA molecule-encoding sequences.

If delivery of a vector comprising a ribozyme or deoxyribozyme construct to a eukaryotic cell is desired, cellular splicing mechanisms within the target cell(s) may be utilized or integrated to cleave out the therapeutic second enzymatic RNA molecule(s) by encoding recognition sequences for the second enzymatic RNA molecules within the flanking sequences of the expressed transcript. Multiple copies of the releasing first enzymatic RNA molecule may be provided to enhance release of the second (i.e. therapeutic) enzymatic RNA molecule if the turnover rate is slower than the degradation rate of the second enzymatic RNA molecule.

A method of forming enzymatic RNA molecule expression vectors and for producing enzymatic RNA molecules are further described in the aforementioned published applications and issued patents, the disclosures of which are incorporated by reference herein.

V. Formulations and Administration of Delivery Vehicles

The conjugates and complexes provided herein are useful in the treatment and prevention of various diseases, syndromes, and hyperproliferative disorders, such as restenosis, other smooth muscle cell diseases, tumors, such as melanomas, ovarian cancers, neuroblastomas, pterygii, secondary lens clouding, and the like. As used herein, "treatment" means any manner in which the symptoms of a condition, disorder or disease are ameliorated or otherwise beneficially altered. Treatment also encompasses any pharmaceutical use of the compositions herein. As used herein, "amelioration" of the symptoms of a particular disorder refers to any lessening, whether permanent or temporary, lasting or transient, that can be attributed to or associated with administration of the composition.

In certain embodiments, the compositions of the present invention may be used to treat angiogenesis-dependent diseases. In these diseases, vascular growth is excessive or allows unwanted growth of other tissues by providing blood supply. These diseases include angiofibroma, arteriovenous malformations, arthritis, atherosclerotic plaques, corneal graft neovascularization, delayed wound healing, diabetic retinopathy, granulations due to burns, hemangiomas, hemophilic joints, hypertrophic scars, neovascular glaucoma, nonunion fractures, Osler-weber syndrome, psoriasis, pyogenic granuloma, retrolental fibroplasia, scleroderma, solid tumors, trachoma, and vascular adhesions.

By inhibiting vessel formation (angiogenesis), unwanted growth may be slowed or halted, thus ameliorating the disease. In a normal vessel, a single layer of endothelial cells lines the lumen, and growth of the vessel requires proliferation of endothelial cells and smooth muscle cells.

As well, the phages of the present invention may be used to treat tumors. In these diseases, cell growth is excessive or uncontrolled. Tumors suitable for treatment within the context of this invention include, but are not limited to, breast tumors, gliomas, melanomas, prostate cancer, hepatomas, sarcomas, lymphomas, leukemias, ovarian tumors, thymomas, nephromas, pancreatic cancer, colon cancer, head and neck cancer, stomach cancer, lung cancer, mesotheliomas, myeloma, neuroblastoma, retinoblastoma, cervical cancer, uterine cancer, and squamous cell carcinoma of skin. For such treatments, ligands are chosen to bind to cell surface receptors that are generally preferentially expressed in tumors.

Through delivery of the compositions of the present invention, unwanted growth of cells may be slowed or halted, thus ameliorating the disease. The methods utilized herein specifically target and kill or halt proliferation of tumor cells having receptors for the ligand on their surfaces.

The phages may also be used to treat or prevent atherosclerosis and stenosis, a process and the resulting condition that occurs following angioplasty in which the arteries become reclogged. Generally, treatment of atherosclerosis involves widening a stenotic vascular lumen, permitting greater blood flow and oxygenation to the distal tissue. Unfortunately, these procedures induce a normal wound healing response in the vasculature that results in restenosis. Of the three components to the normal vascular response to injury, thrombosis, elastic recoil and smooth muscle cell proliferation, anti-thrombotics/platelet inhibitors and vascular stents effectively address acute/subacute thrombosis and elastic recoil, respectively. However, no therapy can modify the vascular remodeling that is due to proliferation of smooth muscle cells at the lesion, their deposition of extracellular matrix and the subsequent formation of a neointima. Accordingly, phage could be used to deliver therapeutic nucleic acids or proteins that would inhibit restenosis.

Wound response also occurs after other interventions, such as balloon angioplasty of coronary and peripheral vessels, with or without stenting; carotid endarterectomies; vein grafts; and synthetic grafts in peripheral arteries and arteriovenous shunts. Although the time course of the wound response is not well defined, if the response can be suppressed for a short term (approximately 2 weeks), a long term benefit is achieved.

In certain embodiments, the bacteriophages of the present invention may be used to treat a variety of genetic abnormalities, such as deficiencies of important functional enzymes. Examples of such diseases include Gaucher's disease (glucocerebrosidase deficiency), mucopolysaccharidosis (beta-glucuronidase deficiency), hyperammonemia (orinithine transcarbamylase defiency), and others.

One skilled in the art would appreciate that the phages of the present invention can be delivered in vivo by administration to an individual, typically via systemic administration (e.g., oral, intravenous, intraperitoneal, intramuscular, subdermal, or intracranial fusion) or topical application (e.g., dermis and mucosal membranes). Using targeted ligands, the bacteriophage of the present invention are capable of targeting a specific cell type for transduction.

Alternatively, the phages of the present invention can be delivered to cells ex vivo. Ex vivo treatment envisions withdrawal or removal of a population of cells from a patient, transduction with bacteriophages containing therapeutic nucleic acids, and re-implantation into the body of a patient. Exemplary procedures for performing generalized ex vivo gene therapy are described in U.S. Pat. Nos. 5,399, 346 and 5,665,350. In addition, cells that have been transduced with phages ex vivo may be reintroduced into the patient or animal as described by a variety of methodologies. See, e.g., U.S. Pat. Nos. 5,399,346, 5,665,350, PCT Publication No. WO 92/15676 (claiming priority to U.S. Ser. No. 667,169), PCT Publication No. WO 90/06997 (claiming priority to U.S. Ser. No. 283,586).

Exemplary cell populations, for ex vivo transduction, include bone marrow cells, liver cells, pancreatic cells, all hemopoetic cells, and umbilical blood and cells. Such cells may be processed to purify the desired cell population for transduction, for example to obtain a specified subset of cells for transduction. Preferred methods of purification include various cell sorting techniques, such as antibody panning, FACS, and affinity chromatography using a matrix coupled to antibodies specifically reactive with the desired subset of cells. Isolated cells may then be transduced and re-introduced to a patient or, alternatively, the cells may be expanded in culture prior to re-introduction.

A. Preparation of Pharmaceutical Agents

Pharmaceutical carriers or vehicles suitable for administration of the conjugates and complexes provided herein include any such carriers known to those skilled in the art to be suitable for the particular mode of administration. In addition, the bacteriophage may be formulated as the sole pharmaceutically active ingredient in the composition or may be combined with other active ingredients.

The bacteriophage can be administered by any appropriate route, for example, orally, parenterally, including intravenously, intradermally, subcutaneously, or topically, in liquid, semi-liquid or solid form and are formulated in a manner suitable for each route of administration. Preferred modes of administration depend upon the indication treated.

The bacteriophage may be formulated into pharmaceutical compositions suitable for local, intravenous and systemic application. Time release formulations are also desirable. Effective concentrations of the bacteriophage are mixed with a suitable pharmaceutical carrier or vehicle. As used herein an "effective amount" of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

The phage vectors of the present invention are particularly well-suited for oral administration and possess the ability to deliver therapeutic gene sequences on a systemic level, unlike most of the gene delivery vectors presently in testing and in use. As noted previously, phage are able to withstand harsh environments and conditions such as those common to the mammalian digestive tract; thus, they are ideally suited for oral/systemic formulations and administration. An additional advantage of the presently-disclosed vectors is the fact that many of the ligands described as preferred embodiments herein are protease-resistant; such ligands are particularly preferred for use in formulations and compositions designed for oral/systemic administration.

Therapeutically effective concentrations and amounts may be determined empirically by testing the conjugates and complexes in known in vitro and in vivo systems, such as those described here; dosages for humans or other animals may then be extrapolated therefrom. The bacteriophage is included in the pharmaceutically acceptable carrier in an amount sufficient to exert a therapeutically useful effect in the absence of undesirable side effects on the patient treated. The phage may be delivered as pharmaceutically acceptable salts, esters or other derivatives of the conjugates include any salts, esters or derivatives that may be readily prepared by those of skill in this art using known methods for such derivatization and that produce compounds that may be administered to animals or humans without substantial toxic effects. It is understood that number and degree of side effects depends upon the condition for which the conjugates and complexes are administered. For example, certain toxic and undesirable side effects are tolerated when treating life-threatening illnesses, such as tumors, that would not be tolerated when treating disorders of lesser consequence.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of toxicity such as sodium chloride or dextrose. Parental preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art.

The phage can also be mixed with other active materials that do not impair the desired action or with materials that supplement the desired action.

The phage may be prepared with carriers that protect them against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others. For example, the composition may be applied during surgery using a sponge, such as a commercially available surgical sponges (see, e.g., U.S. Pat. Nos. 3,956,044 and 4,045,238) that has been soaked in the phage. The phage may also be applied in pellets (such as Elvax pellets(ethylene-vinyl acetate copolymer resin). Preferential carriers in this regard include a gene-activated matrix (GAM), as described in PCT Publication No. WO 97/38729 (claiming priority to U.S. Ser. No. 08/631,334) and PCT Publication No. WO 95/22611 (claiming priority to U.S. Ser. No. 08/199,780, and 08/316,650). Briefly, a gene-activated matrix is any matrix material containing DNA encoding a therapeutic agent, for example, bacteriophage of this invention. Further, such gene-activated matrices are preferentially derived from any bio-compatible material.

If oral administration is desired, the phage should be provided in a composition that protects it from the acidic environment of the stomach, for example in an enteric coating or in combination with an antacid. Alternatively, freeze-dried bacteria that are "infected" with the phage may be used for oral administration purposes, as they have the capacity to propagate in the intestine and release the phage.

Oral compositions will generally include an inert diluent or an edible carrier and may be compressed into tablets or enclosed in gelatin capsules. Tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring. When the dosage unit form is a capsule, it can contain, in addition to material of the above type, a liquid carrier such as a fatty oil.

Finally, the compounds may be packaged as articles of manufacture containing packaging material, one or more conjugates and complexes or compositions as provided herein within the packaging material, and a label that indicates the indication for which the conjugate is provided.

B. Testing of Constructs

The nucleic acid delivery vehicles may be assessed in any number of in vitro and in vivo model systems. As discussed herein and shown in the examples, the phage should bind to a cell in a specific manner and internalize (likely through endosomal pathway). Moreover, the transgene should be expressed by the host (targeted) cells. Thus, appropriate assays include, without limitation, a binding assay to verify that the phages attach to target cell, a displacement assay to show that phage can be displaced by excess free ligand, an internalization assay to demonstrate that phage are internalized (Barry et al., supra; Dunn, supra; and Hart et al., supra), and a functional assay to show that transgene is active in host cell (See e.g., U.S. Ser. No. 09/141,631 corresponding to U.S. Provisional Ser. No. 60/057,067).

The following examples are offered by way of illustration, and not by way of limitation.

EXAMPLES

Example 1

Preparation of Phagemid Particles

The phagemid pEGFP-N1 (Clontech; Palo Alto, Calif.) contains a green fluorescent protein (GFP) gene under control of the CMV immediate-early promoter. The CMV promoter is highly active in a large variety of mammalian cell lines, however, other mammalian cell promoters can be used. The RC-CMVb phagemid is a derivative of pRC-CMV (InVitrogen; San Diego, Calif.). The *E. coli* lacZ gene was inserted into the pRC-CMV phagemid at the EcoRV site of the multicloning site downstream from the CMV promoter to make pRC-CMVb. Both phagemids contain three origins of DNA replication: the pUC origin for replication as a double-stranded plasmid in *E. coli*; the f1 origin for replication as single-stranded phage DNA, and the SV40 origin for high copy number replication in COS-1 (large T-antigen containing) mammalian cells. They also contain the neomycin phosphotransferase gene, regulated by the SV40 early gene promoter, which confers resistance to the antibiotic G418 when expressed in mammalian cells (Southern and Berg, *J. Mol. Appl. Genet.* 1:327–341, 1982).

Phagemid pEGFP-N1 is propagated in the *E. coli* host strain, DH5αF' to allow for super infection with the M13 helper bacteriophage, M13K07. Phagemid particles are prepared according to known methods (see for example, Sambrook et al., *Molecular Cloning: A Laboratory Manual*, Cold Spring Harbor Press, 1989; and Rider et al. in *Phage Display of Peptides and Proteins: A Laboratory Manual*, Academic Press, 1996). A fresh bacterial colony containing pEGFP-N1 is suspended in 3 ml of 2×YT medium, M13K07 is added to a final titer of $2 \times 10^7$ pfu/ml and the culture incubated for 1 hour at 37° C. Kanamycin is added to a final concentration of 70 μg/ml and incubation continued for 14–18 hours. The bacterial culture is pelleted at 12,000×g for 10 minutes, and the supernate is transferred to a fresh tube. The phagemid particles are precipitated by the addition of ⅓ volume of 30% polyethylene glycol (PEG)-1.5M NaCl. The solution is vortexed and chilled for 1 hour on ice or overnight at 4° C. The phage are pelleted by centrifugation at 12,000×g for 10 minutes at 4° C. The pellet is thoroughly drained and resuspended in ¹/₁₀ original volume of PBS (phosphate buffered saline pH 7.4). The PEG precipitation is repeated and the pellet resuspended in 1/20 volume of PBS. The phagemid suspension is heat pasteurized at 65° C. for 5 minutes, filtered through a 0.45 uM filter, and stored at 4° C.

Example 2

Preparation of Modified Vectors for Mammalian Cell Transduction

A mammalian expression cassette is inserted into a phage or phagemid vector and is used to detect ligand mediated phage entry via reporter gene expression in mammalian cells. A type 3 filamentous phage vector is modified for transduction of mammalian cells by insertion of a GFP expression cassette consisting of a CMV mammalian transcriptional promoter, the green fluorescent protein gene from pEGFP-N1 (Clontech; Palo Alto, Calif.), and a bovine growth hormone transcriptional terminator and polyadenylation signal to make the vector, MEGFP3 (see FIG. 1A). The mammalian expression cassette also contains an SV40 origin of replication adjacent to the CMV promoter. Similar constructs for monitoring entry and subsequent expression of phage genomes in mammalian cells are constructed from other known phage or phagemid vectors including pCANTAB 5 E (Pharmacia Biotech; Piscataway, N.J.) or M13 type 3 or 33 for gene III fusions (see Kay, B. K. et al., *Phage Display of Peptides and Proteins: A Laboratory Manual*, Academic Press, 1996, McConnell, S. J. et al., *Mol. Divers.* 1: 165–176, 1996) and M13 type 8 or 88 vector for fusions to gene VIII protein (Roberts et al., *Methods Enzymol.* 267:68–82,1996; Markland, W. et al., *Gene* 109: 13–19, 1991).

Example 3

Linkage of FGF to Phagemid Particles Using Avidin-Biotin

One method for targeting the phage to FGF receptors is to link the phage to FGF via avidin-biotin. This FGF-phage complex is assembled in the presence of test cells at 0° C., and followed by incubation at 37° C. to allow internalization. A mutated FGF, FGF2–3 (Cys at residue 96 is mutated to Ser) (Sosnowski et al., *J. Biol. Chem.* 271: 33647–33653, 1996) is conjugated to biotin at the single free sulfhydryl group using biotin-BMCC (Pierce; Rockford, Ill.) according the manufacturer's suggested protocol. Unreacted biotin is removed by passing the reaction over a PD-10 desalting column. Where relevant, biotinylated transferrin was purchased from Sigma (St. Louis, Mo.) and biotinylated EGF was purchased from Molecular Probes (Eugene, Oreg.).

COS cells are incubated in 12 well plates at 20,000 cells/well for approximately 24 hours prior to phage addition. Cells are washed 2× in ice cold PBS/FBS (PBS with 2% fetal bovine serum). Following, 1.2 µg of B-FGF (biotinylated FGF) is added on ice for 15 minutes. Neutravidin (NAV; a neutral carbohydrate stripped avidin; Pierce, Rockford, Ill.) is added at 10 µg/ml in 1 ml of PBS/FBS for 15 minutes on ice. The cell wash is repeated and biotinylated anti-M13 antibody (Sheep anti-M13-biotin, 5 Prime→3 Prime, Inc.; Boulder, Colo.) is added at 10 µg/ml in 1 ml of PBS/FBS for 15 minutes on ice. The cell wash is repeated and $10^8$ colony forming units are added to each well in 1 ml of PBS/FBS for 1 hour on ice. The cells are washed again, resuspended in fresh media and returned to the incubator at 37° C. GFP expression in cells is monitored by fluorescence microscopy (Nikon Diaphot inverted microscope) using the fluorescein (FITC) filter set.

In one experiment, about 30–35 GFP-expressing cells autofluorescing cells are observed per well after 72 hours. Fewer autofluorescing cells are observed as the number of phage added is decreased. No positively fluorescing cells are observed at $10^5$ CFU or less of phage per well.

The results of control experiments are shown in Table 1. Treatment with a single-stranded nuclease (mung bean nuclease; New England Biolabs, Mass.) did not significantly affect the efficiency of GFP expression indicating that the transfection occurs via intact phage and is not due to contaminating free single-stranded phage genome DNA. Similar results are obtained using DNase I, a single and double stranded nuclease, in place of mung bean nuclease. The addition of 2 µg of EGFP-N1 DNA instead of phage does not result in any GFP positive cells, indicating that GFP infection is not due to internalization of contaminating plasmid DNA in the phage preparations.

TABLE 1

| Treatment | Number of autofluorescing cells/well (72 h) |
|---|---|
| FGF-Biotin + Avidin + Biotin-Anti-M13 Ab | 35 |
| DNase | 32 |
| Omit FGF-Biotin | 1 (large multinucleated) |
| Omit Anti-M13 Ab | 1 (large multinucleated) |
| Omit NAV | 0 |

As indicated, the appearance of GFP-expressing cells is dependent on the presence of biotinylated-FGF, NAV and anti-M13 antibody (Table 1). Including biotinylated-FGF and NAV only or anti-M13 and NAV only results in greatly reduced transfection efficiency (1 positive cell vs 35 per well). No positive cells are seen when the NAV addition step is omitted or when equivalent titers of phage alone are added.

Figure 2:
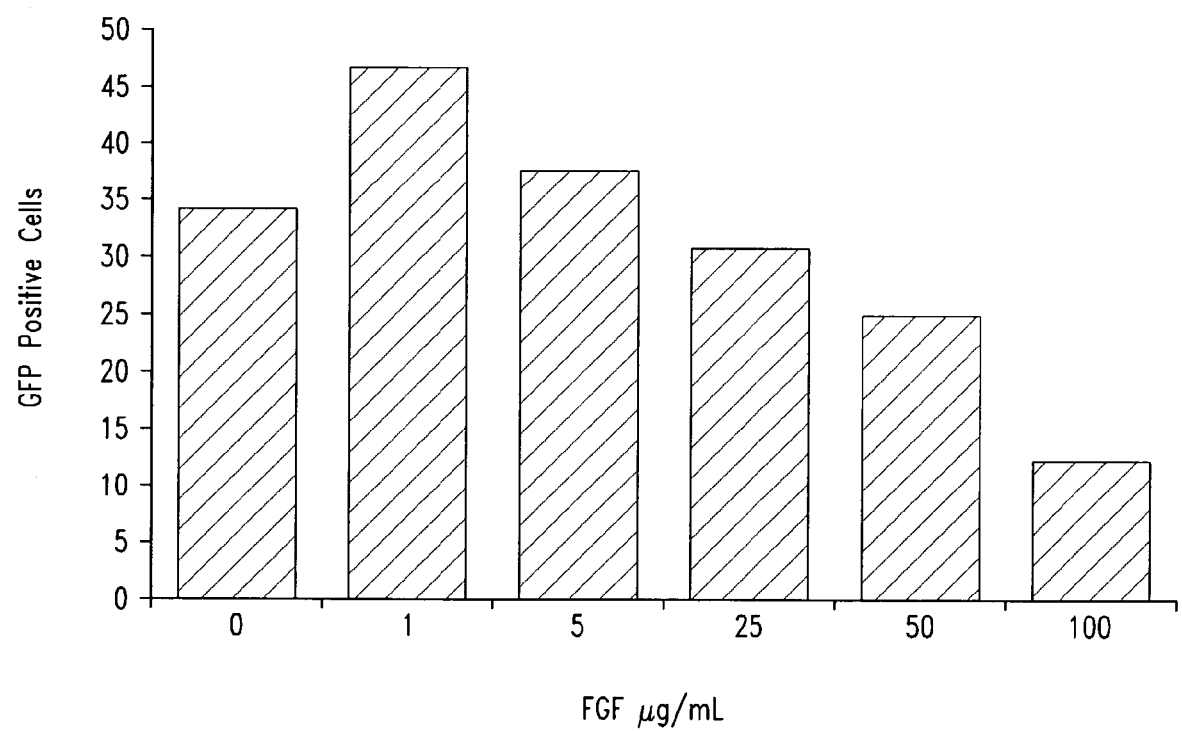
FIG. 2 is a graph displaying the number of cells expressing green fluorescent protein when FGF-phage are incubated with cells in the presence of increasing amounts of free FGF.

When free FGF (non-biotinylated) is added to compete with biotinylated FGF, phage uptake is inhibited (FIG. 2). Free FGF is added 5 minutes prior to biotinylated FGF in increasing concentrations. As presented in FIG. 2, the number of autofluorescing cells is inhibited in a dose dependent manner as more FGF is added. These results indicate that the internalization of phage is mediated by the interaction of the biotinylated FGF with its receptor.

In another experiment, COS cells are incubated in 6 well plates at densities of 40,000 cells/well 24 hours prior to phage addition. The FGF2 phage complex was assembled at the cell surface, using a modification of the procedure described by Moro et al. for antibody tumor targeting (Moro et al., *Cancer Res.* 57: 1922–1928, 1997). The cells were washed twice with ice cold PBS/FBS (PBS with 2% fetal bovine serum) and biotinylated FGF, biotinylated transferrin, or biotinylated EGF was added for 15 minutes. Neutravidin (NAV), a neutral carbohydrate stripped avidin (Pierce, Rockford, Ill.) was then added to bind the biotinylated FGF2 at the cell surface in ice cold PBS/FBS for another 15 minutes and the cells were washed again. Fifteen minutes after adding an aliquot of biotinylated anti-M13 antibody (Rabbit anti-M13-biotin, Sigma; St. Louis, Mo.) (30 µg/ml) to react with the NAV-biotinylated FGF2 complex at the cell surface, the cells were washed and phage added in PBS/FBS. After one hour on ice, the cells were washed, put into fresh culture media and returned to the incubator at 37° C.

to permit internalization. In some instances chloroquine (50–100 μM) was included in media for 2 hours following removal of phage.

Both GFP and β-galactosidase expression were assessed in phagemid particle-treated and COS-1 control cells at 72 hours after the addition of phagemid particles. The expression of GFP in phage-treated cells was measured by counting the number of autofluorescent cells. The cells were washed two times in PBS/FBS and 1 ml of Dulbecco's PBS was added to each well. Fluorescent cells were detected directly in the culture plates using an epifluorescent inverted microscope (Nikon Diaphot) equipped with a fluorescein isothiocyanate (FITC) filter set. GFP experiments were done in triplicate and repeated at least once.

β-galactosidase in lysates was determined from phagemid particle-treated cells using the luminescent β-galactosidase assay system from Clontech (Palo Alto, Calif.) according to manufacturers suggested protocol. The cells were washed in PBS, scraped into 1.5 ml microtubes, and pelleted protein concentrations measured in the lysates. Endogenous enzyme activity was measured in non-transfected COS cell extract and subtracted from each reading. β-galactosidase experiments were done in duplicate wells and repeated at least once.

Figure 3A:
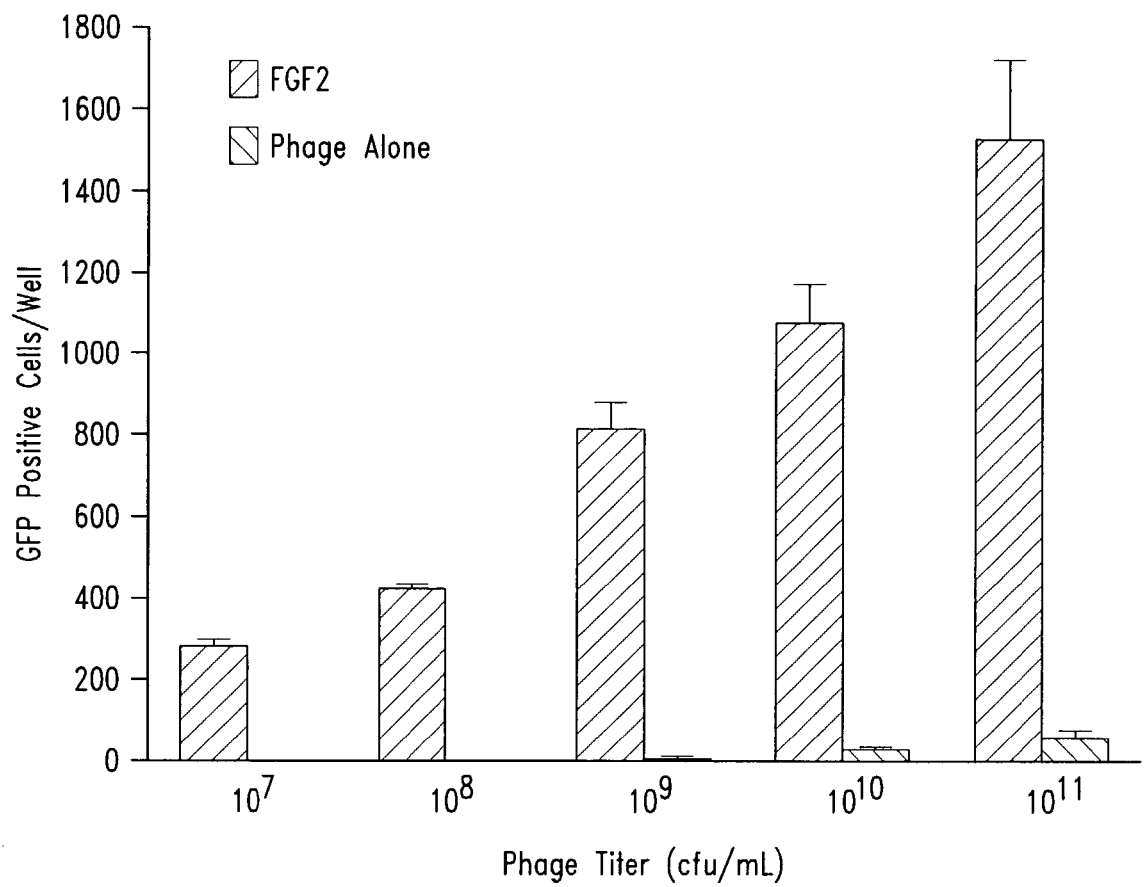
FIGS. 3A and 3B are graphs demonstrating the expression of reporter genes GFP (3A) and βGal (3B) in target cells as a function of phage titer.
Figure 3B:
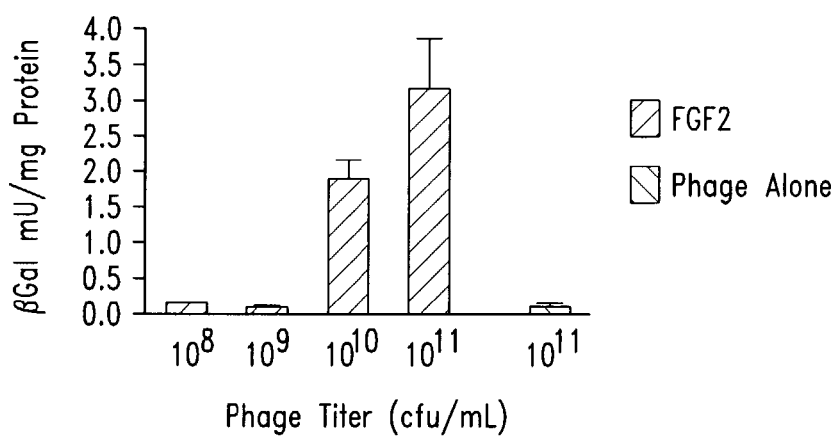

In a typical experiment, 250–1800 (depending on phage titer used, see the dose dependent response graph in FIG. 3A) GFP-expressing and autofluorescing cells are observed per well after 72 hours post FGF2 targeting to COS-1 cells. As demonstrated by FIG. 3A, as little as $10^7$ phage (m.o.i. of 250) resulted in the detection of GFP-expressing cells. As is demonstrated by FIG. 3B, more RC-CMVβ-phagemid particles were required to detect transgene activity, indicating that the total cell lysate β-galactosidase assay was less sensitive than detection of GFP-positive cells by direct observation.

Figure 4A:
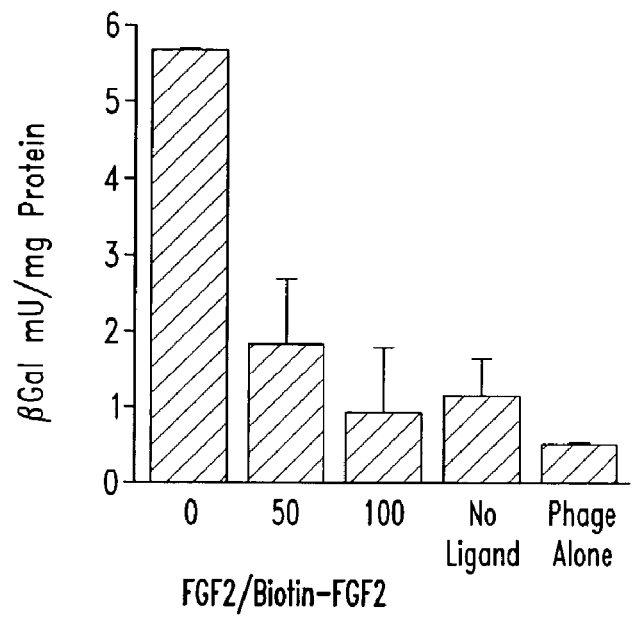
FIGS. 4A–4D are graphical representation demonstrating the specificity of FGF2 targeting.
Figure 4B:
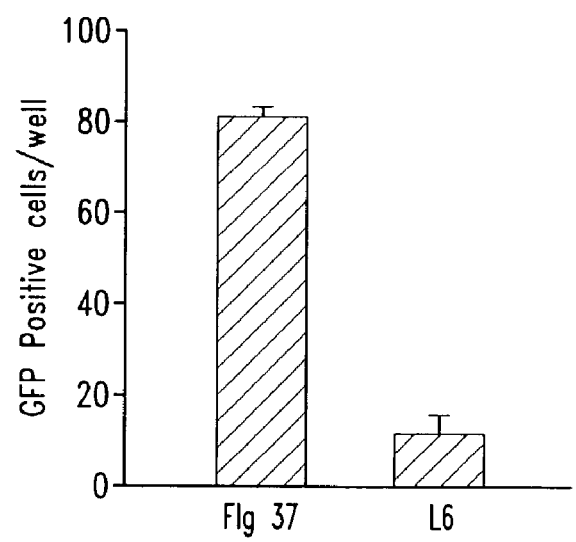
Figure 4C:
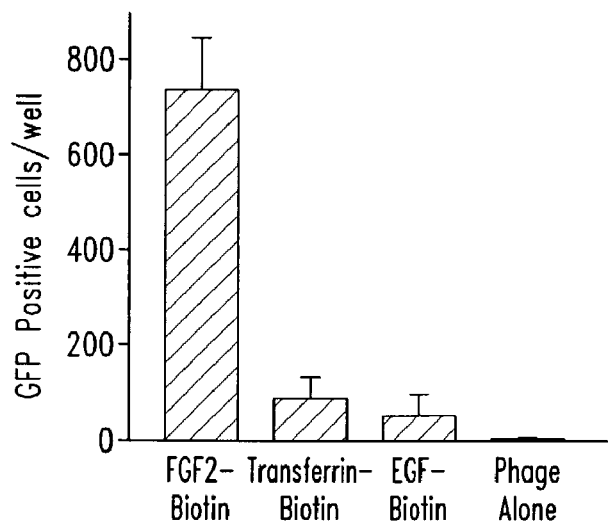

The results of several control experiments are depicted in FIGS. 4A–4C. When increasing amounts of FGF2 were used to compete with targeted phage binding, a 100-fold molar excess of free FGF2 successfully blocked the phagemid particle-dependent transfection of COS-1 cells (FIG. 4A). Non-specific transduction seen with phage alone was not affected by the addition of the same amount of free FGF2 (not shown). To further investigate the possibility that transduction of cells by FGF2-targeted phage delivery was dependent on the high-affinity FGF receptor, phage particles were targeted to L6 rat myoblast cells, a cell line that lacks high-affinity FGF2 receptors (Olwin and Hauschka, *J. Cell Biochem.* 39: 443–454, 1989; available from ATCC; Manassas, Va.) and compared the response to a stable transfectant of L6 (F1g37) that constitutively overexpresses FGFR1 (obtained from Dr. Murray Korc, UCI; Irvine, Calif.; also readily created by those skilled in the art). As shown in FIG. 4B, the presence of high-affinity FGF2 receptors facilitates the FGF2-targeted phage gene transfer. A greater transduction efficiency was observed in the FGFR-positive F1g37 cells than the parent L6 cells and no GFP positive cells were observed for either cell line in the absence of NAV. A comparison between FGF2 targeting and 2 other targeting ligands, transferrin (Zatloukal et al., 1992) and EGF (Watkins et al., *Gene Ther.* 4: 1004–1012, 1997) is also easily performed. Both are relatively inefficient at delivering phage to COS-1 cells for gene expression. The number of GFP-expressing cells is markedly reduced when biotinylated FGF2 is substituted by biotinylated transferrin or biotinylated EGF (FIG. 4C).

Example 4

Iintracellular Trafficking

Figure 4D:
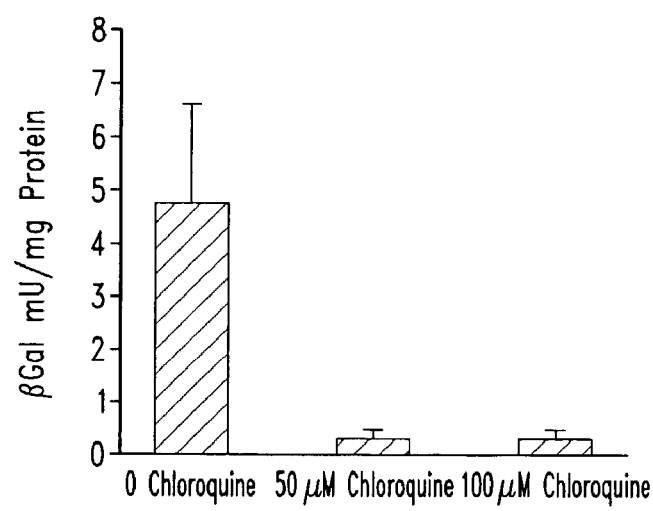

COS cells were treated with chloroquine as described in Sosnowski et al. (*J. Biol. Chem.* 271: 33647–33653, 1996), typically at concentrations of 50 to 100 μM for 2 hours. Sosnowski et al. demonstrate a potentiating effect of chloroquine when FGF2 targets naked plasmid DNA, however, when chloroquine is used in combination with transduction of cells by FGF2-targeted phagemid particles, the chloroquine unexpectedly had an inhibitory effect on transduction of the target cells (FIG. 4D).

Example 5

Linkage of FGF to Phagemid Particles Using PolyLysine

In this example, FGF is linked to polylysine, which then binds to phagemid particles as a result of the interaction between positively charged polylysine and negatively charged phage.

FGF is covalently linked to poly-D-lysine (average polymer length of 84) using S-2-pyridyl disulfide (SPDP) as described by Sosnowski et al. (*J. Biol. Chem.* 271: 33647–33653, 1996). The EGFP-N1 phagemid particles are mixed with 5 μg of FGF-polylysine or 2.5 μg of polylysine alone (the FGF-polylysine is approximately 50% polylysine by weight) and allowed to stand at room temperature for 30 minutes prior to addition to COS cells that are grown in 12 well plates. Cells are examined at 72 hours by fluorescent microscopy, and autofluorescent GFP positive cells counted.

Figure 5:
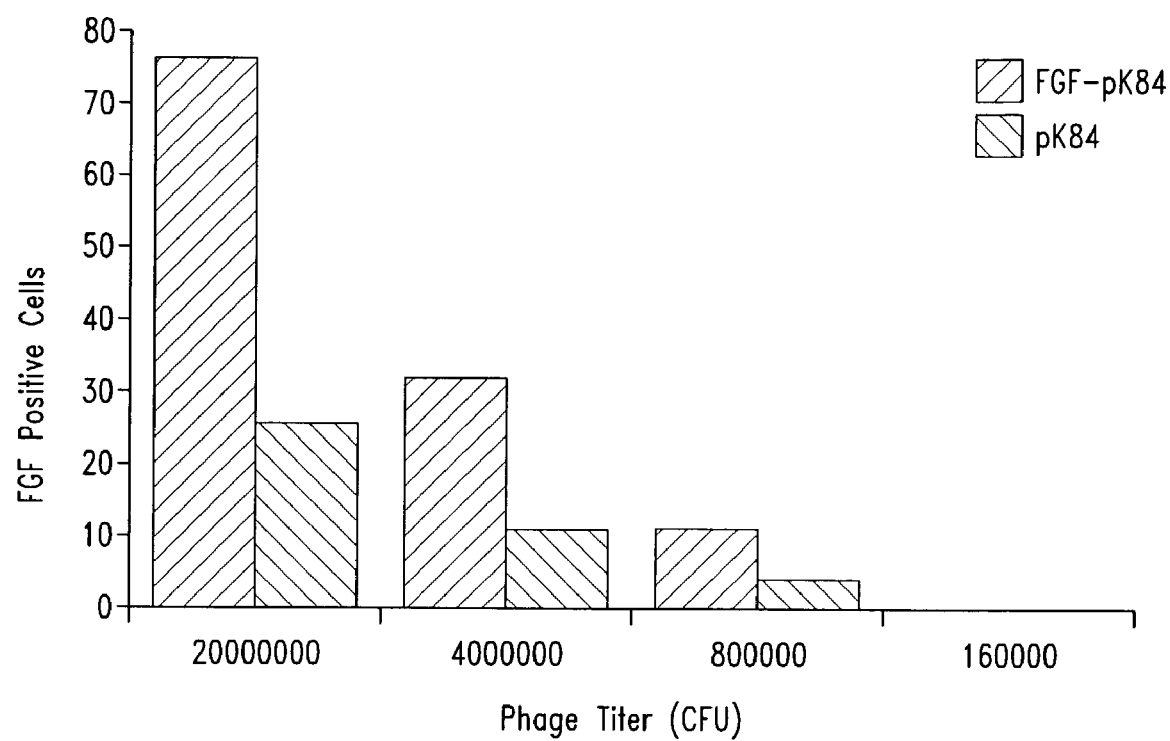
FIG. 5 is a graph displaying the number of FGF positive cells resulting from incubation of polylysine+phage or FGF–polylysine+phage.

As shown in FIG. 5, the GFP gene is transduced into COS cells via phage in the presence of FGF-polylysine. Increasing phage titer results in an increase in GFP positive cells. About one-third of the GFP positive cells represent background due to non-specific uptake of phage coated with polylysine alone.

Example 6

Covalent Linkage of FGF to Phagemid Particles

In this example, the coat proteins of M13 phage are conjugated directly to FGF using heterobifunctional crosslinking reagents. A free lysine at the N-terminus of the gene VIII coat protein is available for chemical modification (Armstrong et al, *EMBO J.* 2: 1641–1646, 1983). In this method, phage particles are first thiolated by the addition of 3–30 molar excess of SPDP in 0.1M phosphate buffer pH 7.5, 0.1M NaCl for 30 minutes at 23° C. Unreacted reagent is removed by gel filtration. The FGF2–3 mutein of FGF is then reacted with thiolated phage in a 2–10 fold molar excess for 24 hours at 23° C. Free FGF2–3 is removed by gel filtration. Phage linked to FGF are further purified by heparin-Sepharose column affinity chromatography.

The linkage of FGF to phage protein is confirmed by polyacrylamide gel electrophoresis and immunoblotting of phage proteins. Under non-reducing conditions, the FGF modified gene VIII protein is shifted from an apparent molecular mass of 5,500 Da to 23,500 Da. The addition of reducing agent to the sample buffer disrupts the disulfide linkage and yields free FGF (~8,000 Da) and gene VIII protein.

The chemically modified FGF-phage are assayed for the ability to transduce mammalian cells. FGF modified pEGFP-N1 phagemid particles bearing the CMV-GFP expression cassette are added to COS cells plated at 20,000 cells/well in 12 well plates. The cells are assayed for GFP expression by fluorescence microscopy 72 hours after the addition of phage.

Example 7

Genetic Fusion of FGF to Phage Coat Protein

Figure 1B:
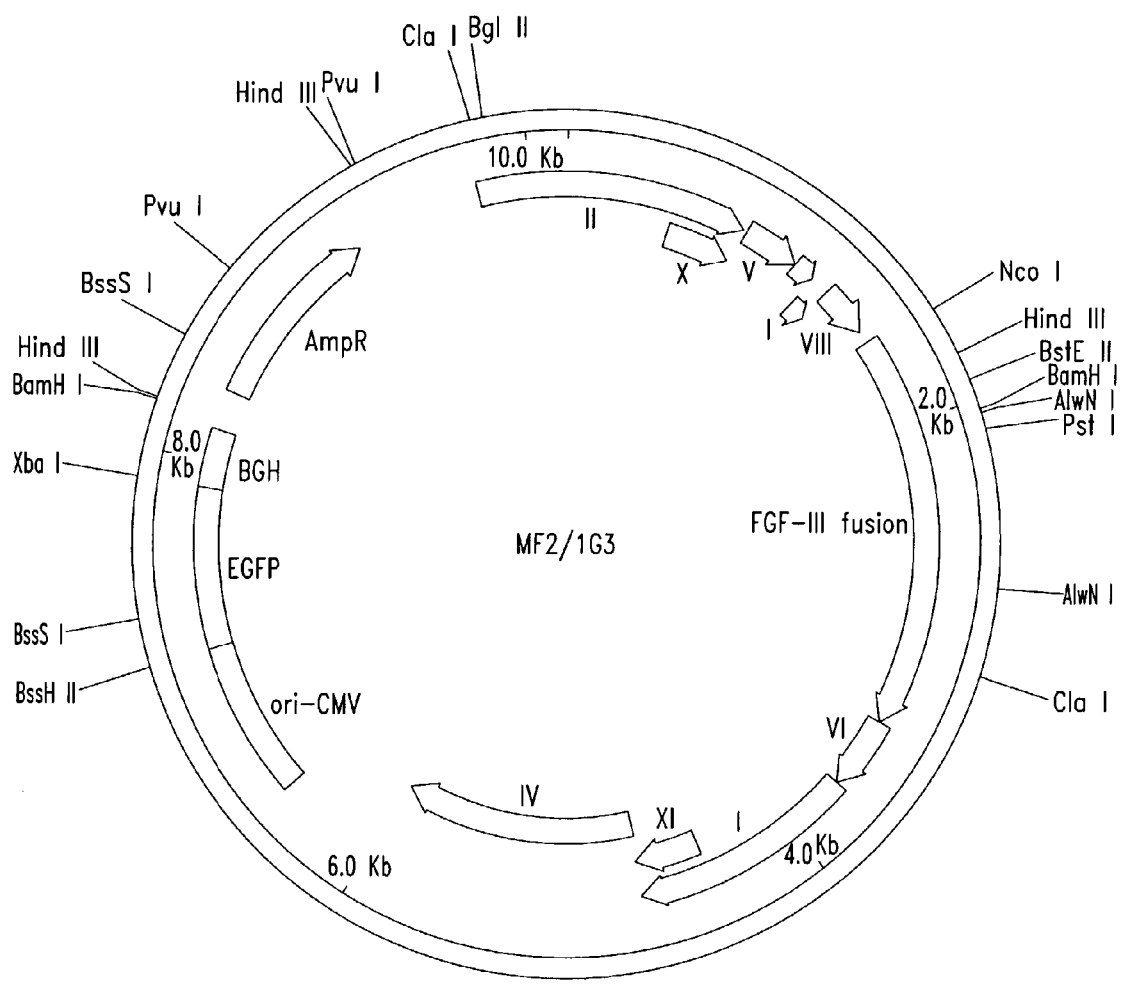

In the following examples, a phage that displays FGF2 on its surface is used to bind to the FGF2 receptor on mammalian cells and be internalized. An FGF2 gene is subcloned into the modified M13 phage type 3 vector, MEGFP3 (FIG. 1A), to create the ligand display phage, MF2/1G3 (see FIG. 1B). The MEGFP3 vector has been modified with a mammalian expression cassette designed to express the reporter gene GFP to monitor mammalian cell transduction by the phage. Transduction results can then be quantitated using flow cytometry (FACscan, Becton Dickinson, Mountain View, Calif.) to measure the distribution of GFP expressing cells in the population and by fluorometry of cell extracts to measure total GFP produced. Other vectors include pCANTAB 5 E (Pharmacia Biotech; Piscataway, N.J.) or M13 type 3 or 33 for gene III fusions (see Kay et al., *Phage Display of Peptides and Proteins: A Laboratory Manual*, Academic Press, 1996, McConnell et al., *Mol. Divers.* 1: 165–176, 1996). Similarly, FGF2–3 is cloned into M13 type 8 or 88 vector for fusion to gene VIII protein (Roberts et al., *Methods Enzymol.* 267:68–82, 1996; Markland et al., *Gene* 109:13–19, 1991).

Figure 6:
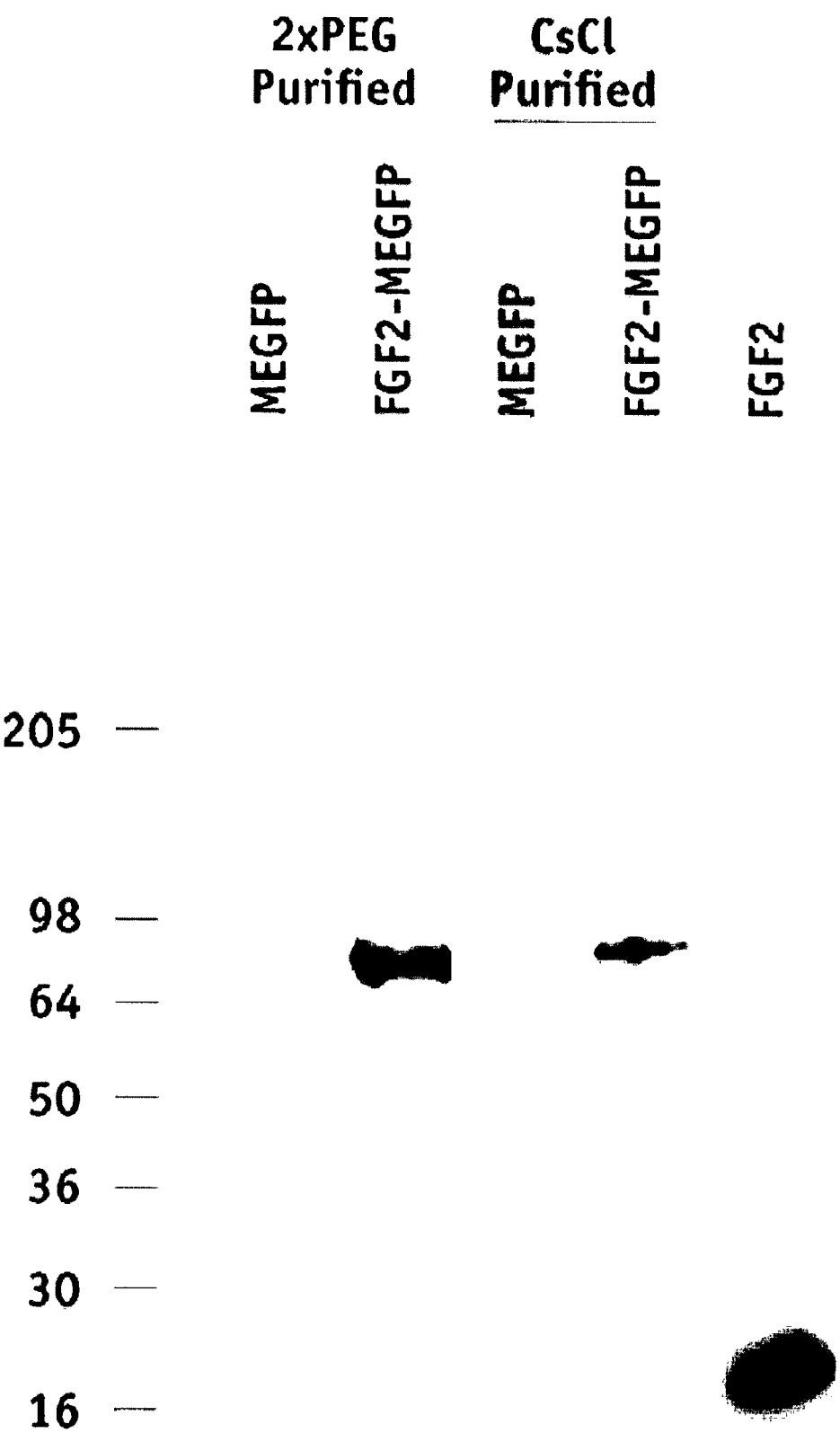
FIG. 6 is a scanned image of a Western Blot analysis representing detection of FGF2-pIII fusion protein in protein extracts from purified FGF2-phage (FGF2-MEGFP).

To facilitate cloning, the FGF2 gene is amplified by PCR using oligonucleotide primers that contain appropriate restriction endonuclease sites in the phage vector gene III or VIII genes. The resulting phage express FGF2 on their surface coat as detected by anti-FGF2 antibodies in western blots (FIG. 6) and by ELISA (FIG. 7). Binding of the FGF2 fusion phage to FGF2 receptor is assessed by ELISA in which recombinant FGF2 receptor is attached to the solid phase and an anti-phage antibody is used as the primary detection antibody.

Western blot detection of FGF2-pIII fusion utilizes extracts from equivalent phage titers of purified FGF2 phage and control phage (MEGFP3) separated by polyacrylamide gel electrophoresis and blotted onto nitrocellulose. FGF2 and FGF2-fusion phage are detected with an anti-FGF2 monoclonal antibody (Transduction Labs; Lexington, Ky.) and HRP conjugated anti-mouse secondary antibody (American Qualex; San Clemente, Calif.) with chemiluminescent development. A single protein band is detected in the cesium chloride purified FGF2-phage extract migrating at about 80 kDa. This is about the size predicted for the FGF2-pIII fusion protein (FGF2 (18 kDa) fused to pIII (migrates ~60 kDa)). CsCl purification is performed to remove any non-covalently bound FGF2 fusion protein from the phage particles.

Figure 7A:
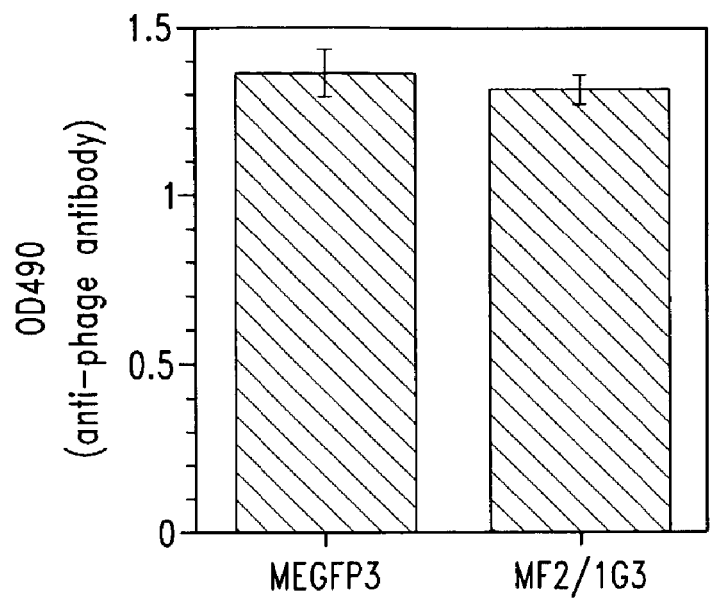
FIGS. 7A and 7B are bar graphs of ELISA detection of FGF2 on FGF2-phage.
Figure 7B:
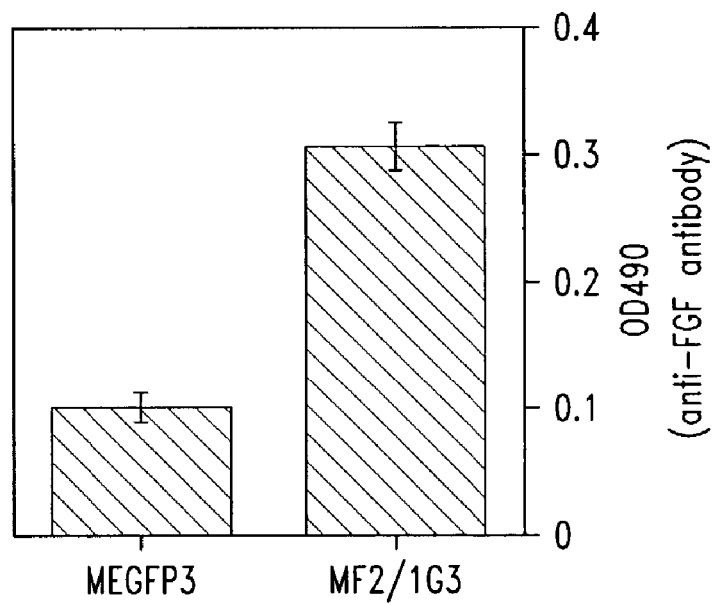

Binding of the FGF2 fusion phage to FGF2 receptor is assessed by ELISA in which recombinant FGF2 receptor is attached to the solid phase and an anti-phage antibody is used as the primary detection antibody. Briefly, phage were captured with an anti-FGF2 rabbit polyclonal antiserum bound to the plate well. An HRP conjugated anti-M13 antibody (Pharmacia Biotech; Piscataway, N.J.) was used to detect the bound phage. When anti-phage antibody is used to capture the phage and equivalent OD is observed for both control (MEGFP3) and FGF2-phage (MF2/1G3) indicating that equivalent phage particles are applied to the plate (FIG. 7A). In FIG. 7B an increased OD indicates the presence of FGF2 on the MF2/1G3 FGF2-phage.

Example 8

Transduction of Mammalian Cells by FGF-Ligand Display Phage

Figure 8A:
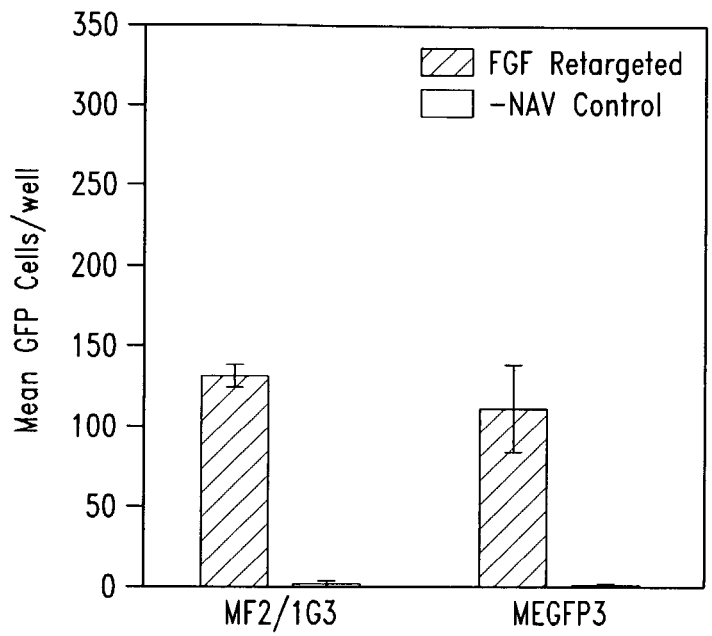
FIGS. 8A and 8B are bar graphs representing the transduction of COS cells by FGF2-phage.
Figure 8B:
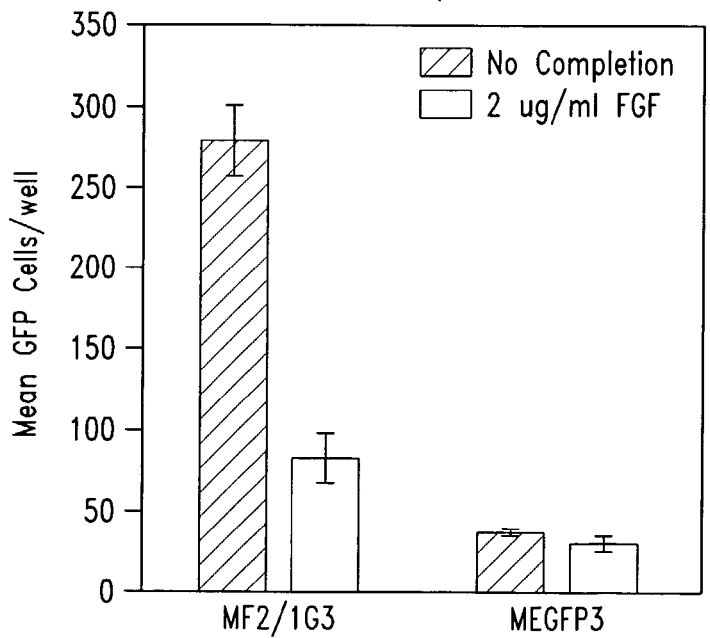

FGF2 display phage (MF2/1G3) and an identical phage that lacks the FGF2 gene (MEGFP3) are compared for receptor mediated internalization and reporter gene expression in COS cells. The phage are incubated with the cells for 4 hours at 37° C. in DME (Dulbecco's modified Eagles medium, Sigma Chemical; St. Louis, Mo.) containing 2% BSA (bovine serum albumin) as a blocking agent. After washing to remove unbound phage the cells are returned to the incubator for an additional 72 hours. Transduction is measured by counting GFP positive autofluorescent cells. As shown in FIG. 8B, the FGF2 display phage result in about a 10 fold greater transduction efficiency than the control phage indicating that the displayed FGF2 ligand on the surface of the phage particles results in receptor mediated binding and internalization of phage with subsequent expression of the phage reporter gene. The specificity of the FGF2-phage mediated transduction is demonstrated by successful inhibition of transduction with excess free FGF2 (2µg/ml) (FIG. 8B). The low level nonspecific uptake and transduction by the control phage (MEGFP3) is not affected by the presence of excess FGF2.

It is important to show that the MEGFP3 control phage is equally capable of transducing mammalian cells as the display phage when appropriately targeted. To compare the transduction ability of both the FGF2-phage and the control phage, equivalent titers of each phage were used to transfect COS cells using the avidin-biotin FGF2 targeting method. In this method biotinylated FGF2 is contacted with the cells and used to capture phage particles via the addition of avidin and a biotinylated anti-phage antibody. The phage/FGF2/cell binding is performed on ice, unbound phage removed by washing, cells returned to the incubator at 37° C., and transduction assessed at 72 hours. As seen in FIG. 8A, there is no significant difference in transduction between FGF2-phage and control phage when FGF2 is attached to the phage via an avidin biotin linkage. In this case the biotinylated FGF2 is in excess of the FGF2 displayed on the phage surface such that internalization is expected to be primarily via the biotinylated FGF2. These data demonstrate specific receptor mediated transduction of mammalian cells by filamentous phage that genetically display a targeting ligand (FGF2).

Example 9

Sustained Expression by Selective Pressure

In order to determine whether transgene expression can be maintained in cells after the introduction of phagemid particles into cells, neomycin resistance was used to select transfected cells. Cells were treated with phagemid particles as described above and 48 hours later, the cells were split at a ratio of 1:10 into fresh medium. The medium was removed and replaced with selective medium containing G418 (700 µg/ml) 24 hours later. As surviving colonies formed (7–10 days), their GFP content was evaluated using fluorescence microscopy. Cell lines derived from these colonies were maintained under G418 selection (>3 months).

Figure 9A:
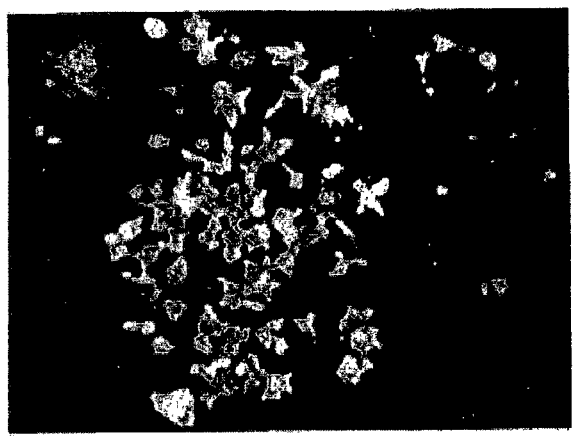
FIGS. 9A and 9B are fluorescent microscopy images of stable transfectants expressing the reporter gene GFP.
Figure 9B:
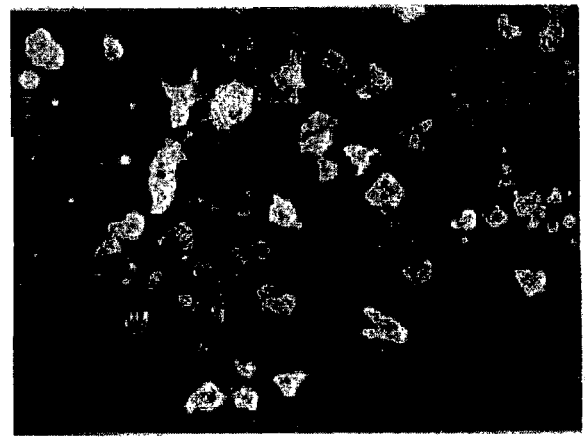

As shown in FIG. 9A (100× magnification), when transduced cells were cultured in the presence of G418, the drug-resistant colonies that appeared where nearly all cells that were positive for GFP activity. The colonies were expanded and maintained as stable cell lines expressing the GFP protein for over 3 months (FIG. 9B (400× magnification)).

Example 10

EGF Mediated Mammalian Cell Transduction

Figure 10:
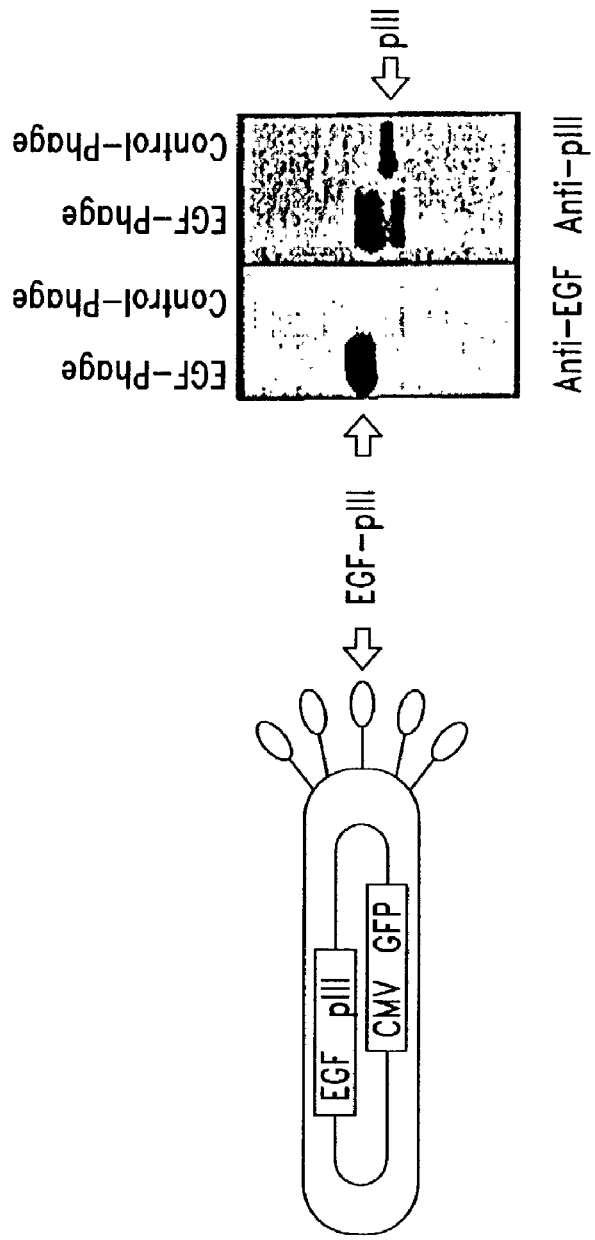
FIG. 10 is a scanned image of a Western Blot analysis representing detection of EGF-pIII fusion protein in protein extracts from purified EGF-phage.

Epidermal growth factor displaying phage were constructed as described above for FGF displaying phage. Western blot analysis demonstrates that EGF was efficiently expressed on the phage coat in a multivalent manner (FIG. 10). Phage were prepared for Western analysis by obtaining the EGF-phage from cultures of infected host bacteria and purified by PEG precipitation and CsCl gradient centrifugation. The phage particle proteins were then separated by gel electrophoresis and blotted onto a nitrocellulose membrane. Blots were then probed with either anti-EGF or anti-pill antibody (mouse anti-human EGF, Biosource International; Camarillo, Calif.) or anti-pill antibody (mouse anti-pIII, MoBiTech; Germany) followed by HRP-goat-anti-mouse (Jackson Laboratories, USA).

Figure 11:
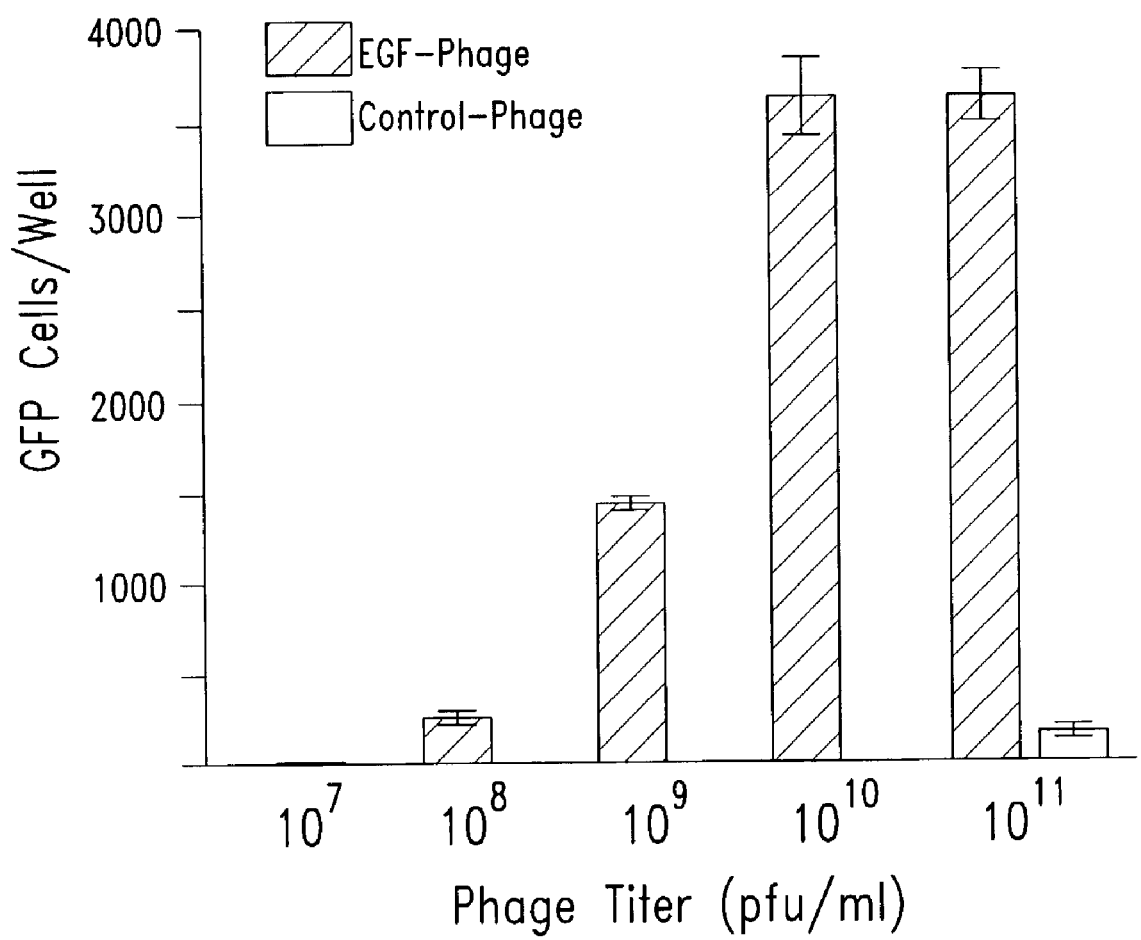
FIG. 11 is a bar graph representing the dose response of COS cells to various phage titers.
Figure 12:
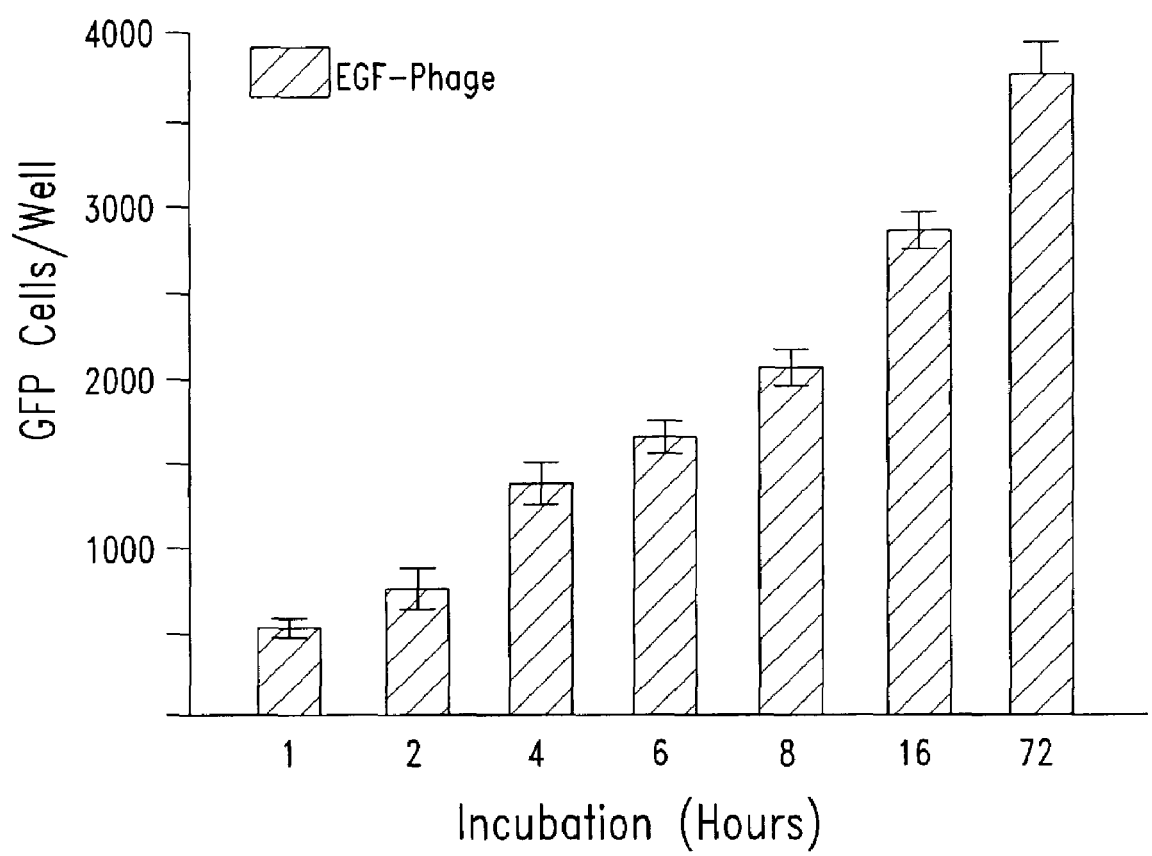
FIG. 12 is a bar graph representing a time course analysis of various incubation times and the effect on transduction.

Following the procedures detailed above, EGF-phage were screened for their ability to effectively transduce COS cells. Briefly, EGF-phage were incubated with COS cells (~75,000 cells/well) for 72 hours with a variety of phage titers. As demonstrated by FIG. 11, the optimal dose was $10^{10}$ pfu/ml which resulted in the highest transduction efficiency with almost no non-specific transduction by untargeted phage. Transduction efficiency also increases with longer incubation times. As demonstrated in FIG. 12, when EGF-phage were incubated with COS cells (~75,000 cells/well) at $10^{11}$ pfu/ml for various times and subsequently measured for GFP expression at 24, 48, 72, 96, and 120 hours, longer incubation times increased transduction efficiency up to 96 h.

Figure 13A:
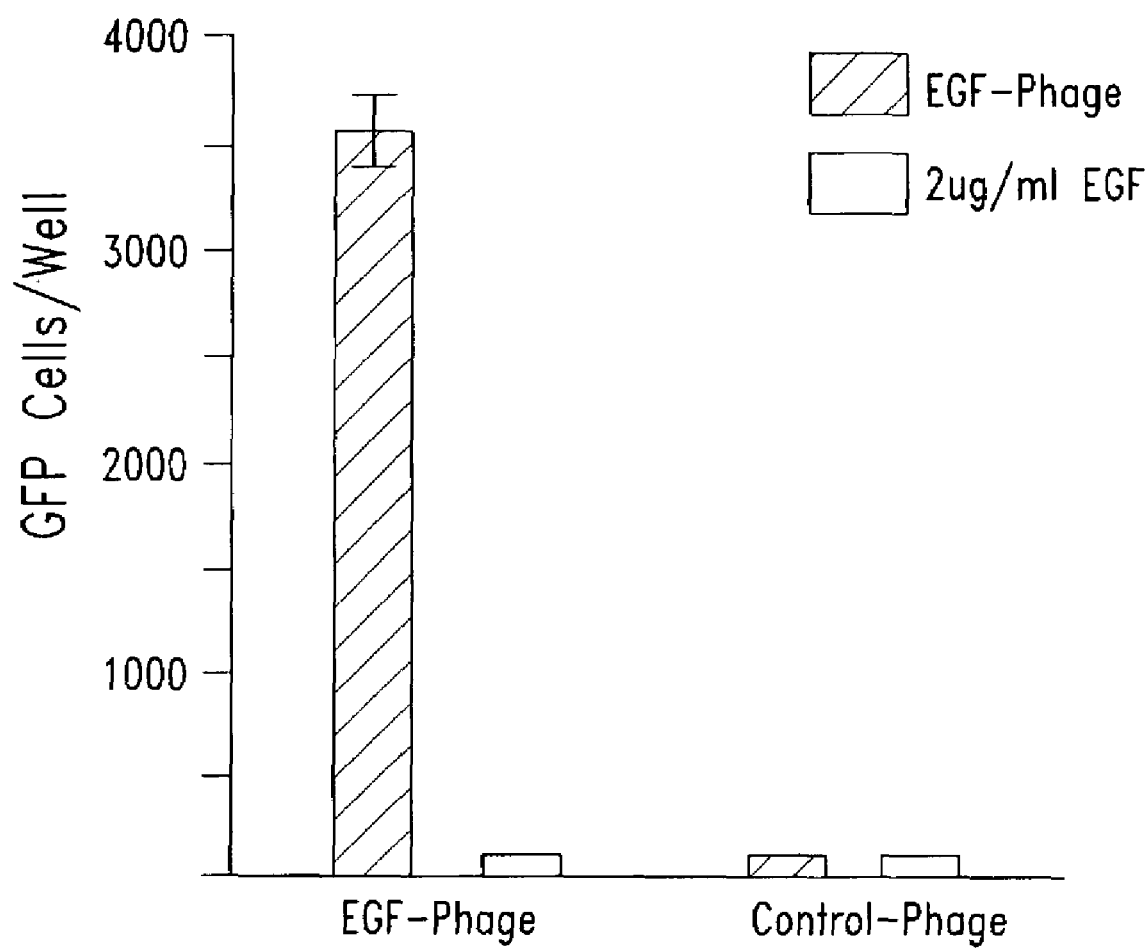
FIGS. 13A and 13B are bar graphs representing the specificity of transduction of COS cells by EGF-phage.
Figure 13B:
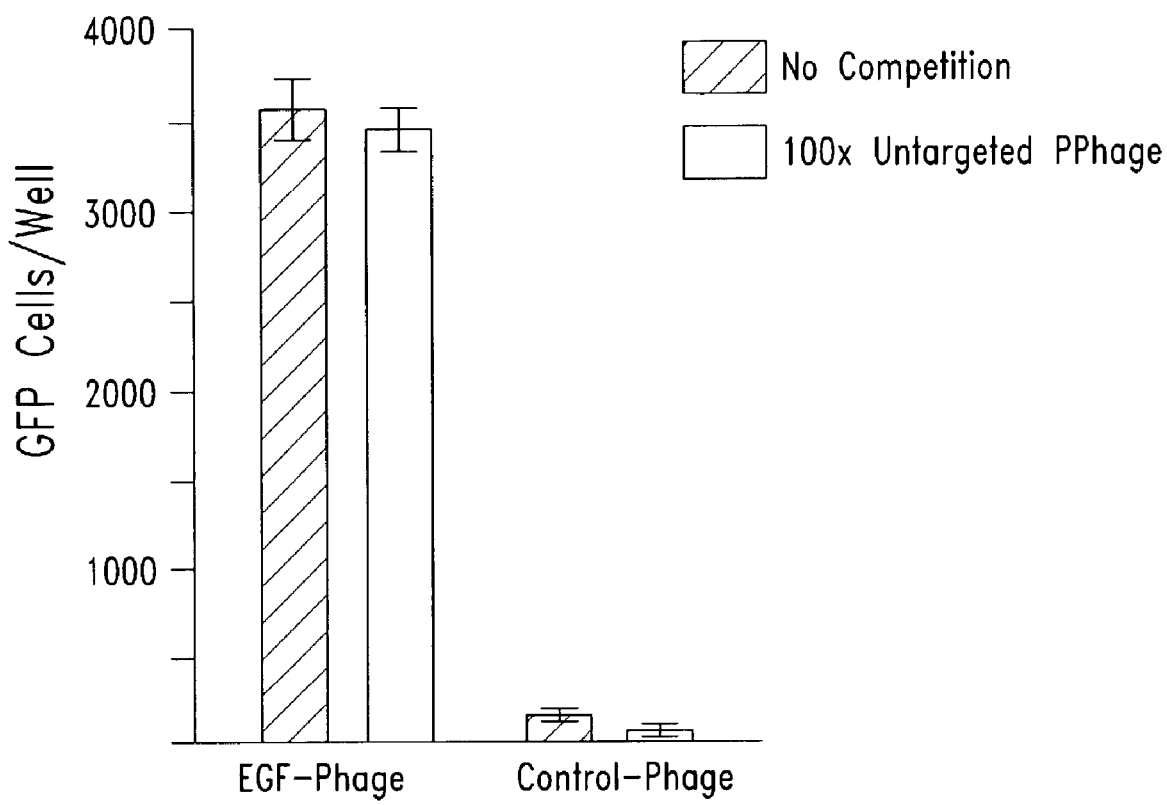

Further, specificity of EGF-phage mediated COS cell transduction was determined by incubating EGF-phage with excess ligand. As depicted in FIGS. 13A and 13B, COS cells incubated with $10^{11}$ pfu/ml of phage for 72 hours with or without excess ligand or untargeted phage demonstrate that targeting is due to the presence of the ligand, and is specific for the cognate high affinity receptor on the surface of the target cells.

Example 11

Transduction of Carcinoma Cells Using EGF Displaying Phage

Phage that display a ligand as a pIII fusion on the phage coat and carry the GFP expression cassette are prepared using standard protocols, as discussed above. Control phage that carry GFP but don't display a ligand are also prepared. Candidate cell targets are seeded into 6 well culture plates at about 40,000 cells/well. At 24 hours after seeding cells, phage are added at ~$10^{10}$ pfu/ml. The plates are incubated at 37° C. for an additional 72 hours. Each cell well is scored by counting GFP positive autofluorescent cells. The cell types that have a ratio of GFP positive cells in the ligand-phage treated well/control phage treated cells of greater than 1.0 are selected as targets for further study and characterization. As an alternative to GFP, a drug resistance gene can be used in which case after 72 hours the cells are allowed to continue growth in selective medium containing the drug. Positive cell types are scored by counting wells that have drug resistant colonies.

Figure 14:
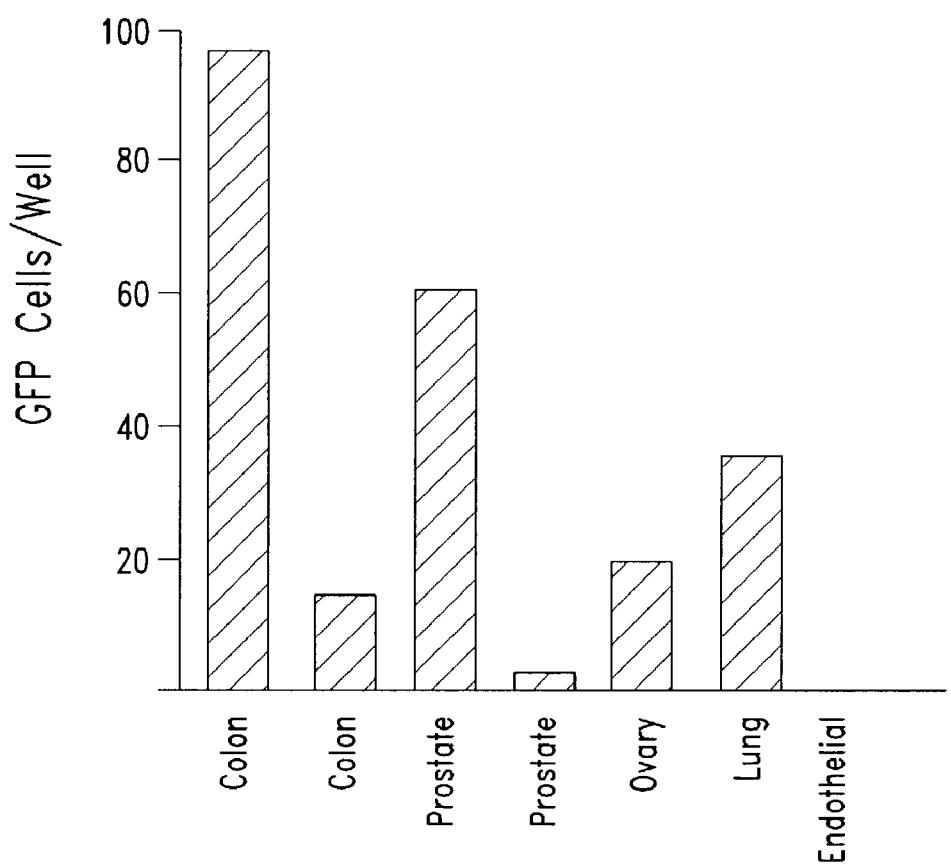
FIG. 14 is a bar graph representing transduction specificity of a variety of human carcinoma cells.

Carcinoma cell lines which are known to express the EGF receptor were screened by the above method using EGF-phage and compared to the control endothelial cell line which is EGF receptor negative (Cell lines obtained from ATCC, Manassas, Va. and grown under standard ATCC culture conditions). As shown in FIG. 14, the carcinoma cell lines derived from various tissues were differentially transduced while the receptor negative, endothelial cells displayed no transduction. Accordingly, identification of target cells or tissues can be accomplished using these methods.

Example 12

Creation of and Transduction with a Hybrid AAV-Phage Vector

Figure 15:
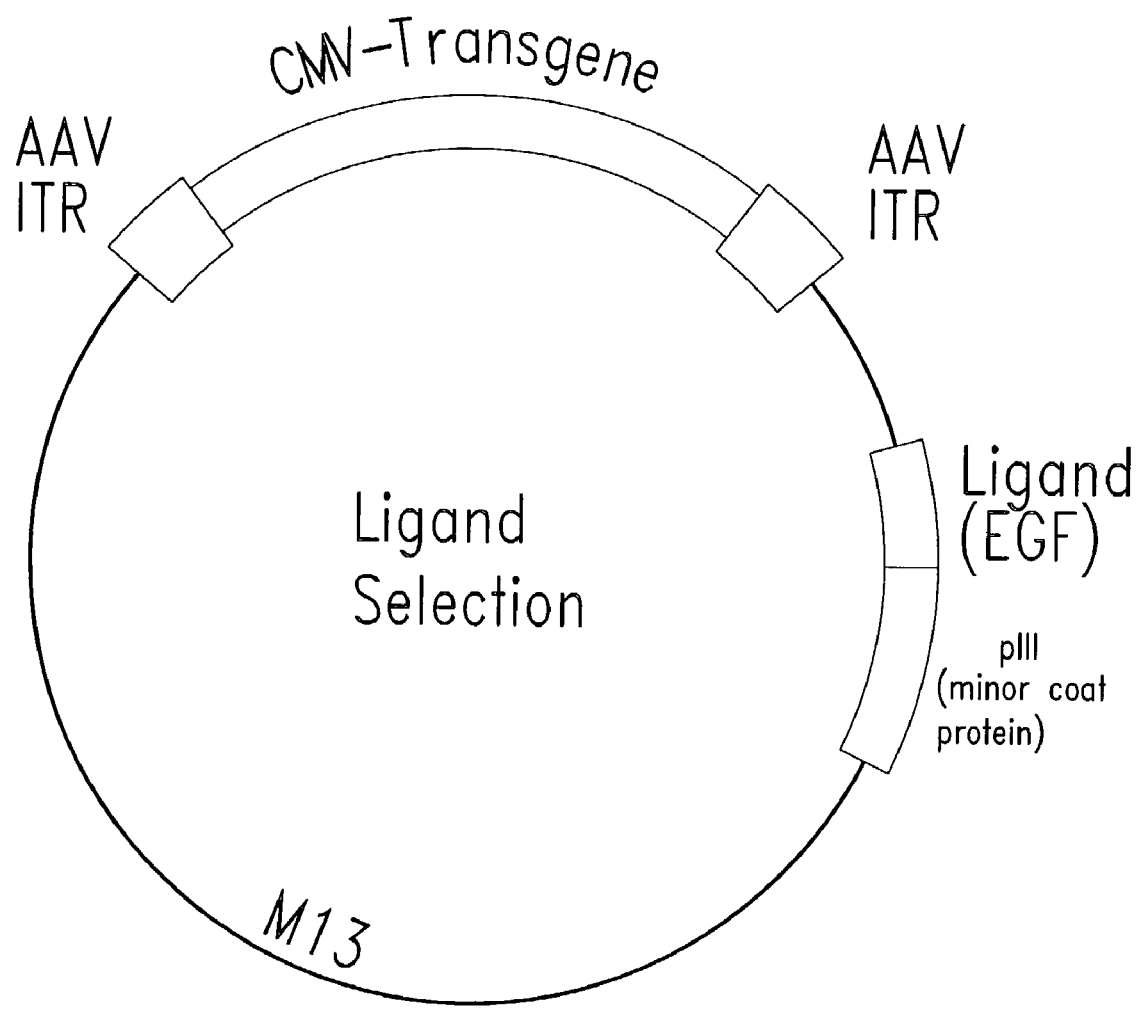
FIG. 15 is a vector map of an AAV-Phage hybrid genome vector.

The AAV-phage vector is created using an M13 (MG3) Bacteriophage vector as a backbone (see, Larocca et al., FASEB, in press, 1999). The vector illustrated in FIG. 15 is created by inserting an ITR flanked transgene cassette (e.g., a promoter driven reporter gene or therapeutic gene) into the intergenic sequence of a MG3 replacing CMV GFP (see, e.g., the vector pAAV/Svneo (ATCC #68065) and pAV.C-MV.LacZ (Fisher et al., *J. Virol.* 70(1):520–532,1996). This vector also contains a genetic fusion of a ligand to the pIII gene as described in Example 7, above. In the present example, however, the nucleic acid sequences encoding EGF are used in place of the FGF sequences used in Example 7 and fused to the N-terminus of the pill coding region.

Figure 16A:
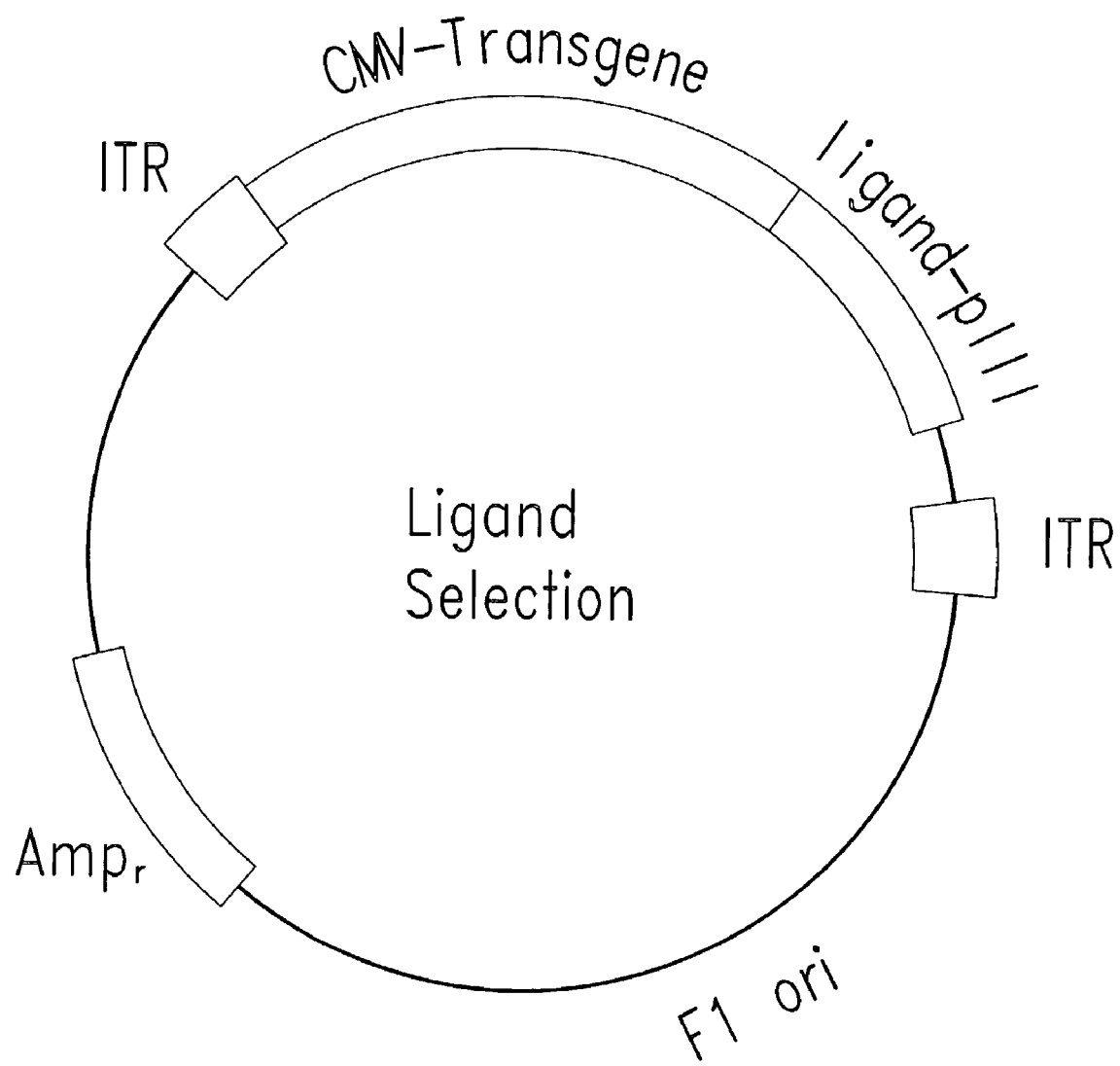
FIGS. 16A and 16B are vector maps of AAV-Phage hybrid phagemid vectors.
Figure 16B:
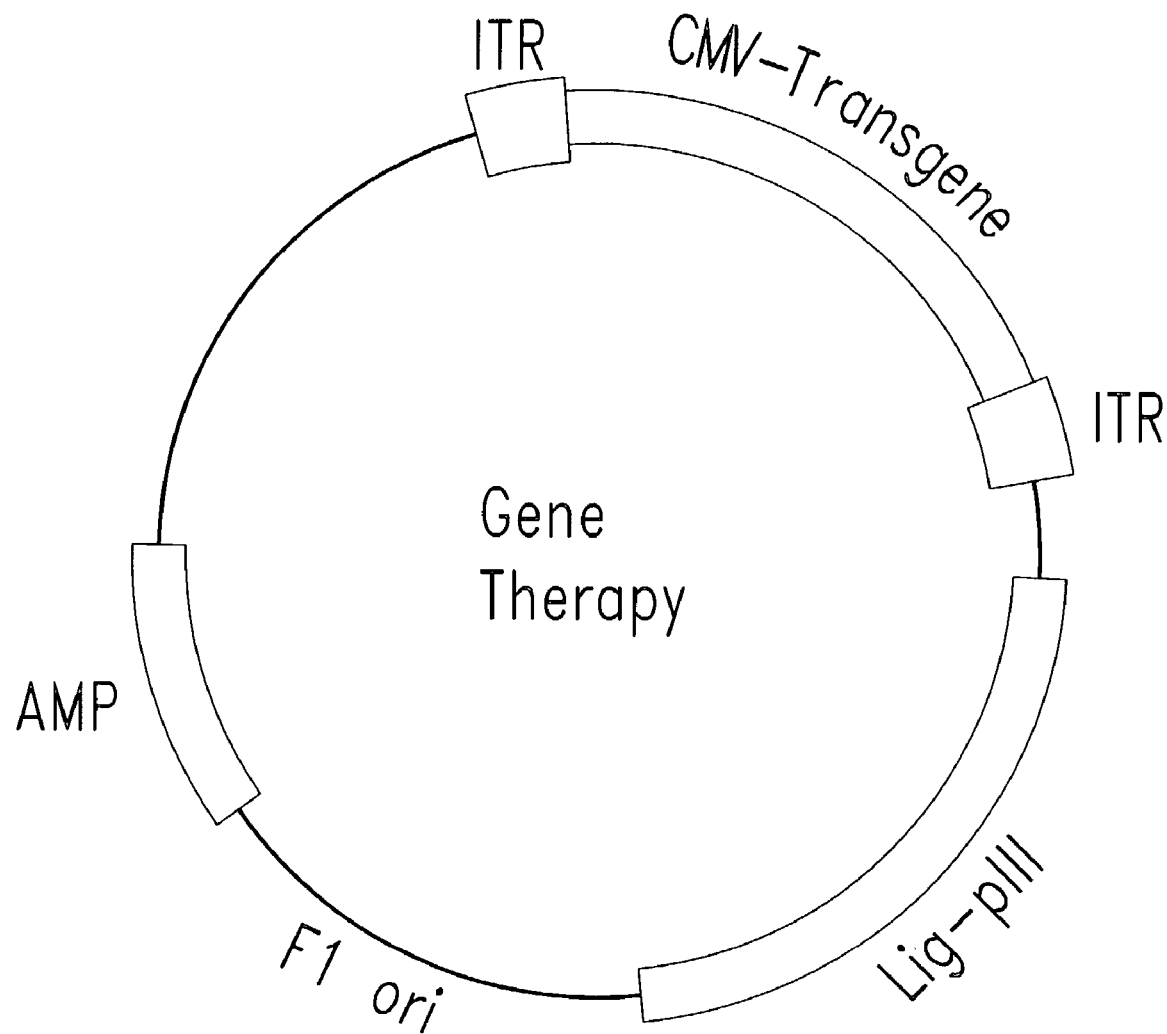

Alternatively, a phagemid vector is created as illustrated in FIG. 16. This vector is created by inserting an ITR flanked transgene cassette (e.g., a promoter driven reporter gene or therapeutic gene) into a suitable cloning site of any currently available phagemid vector (i.e., pCANTABSE, Invitrogen). As illustrated in FIG. 16B, the vector should also contain an insertion point for an pIII/pVIII-ligand fusion construct, such as discussed above, for directing the phage particles into the target cells or tissues.

The hybrid vector is then electroporated into an $F^+$ host strain of bacteria (e.g., DH5α) and phage particles are prepared using standard protocols. If a phagemid vector is used, then the phage particles are rescued by using helper phage to package the particles. The resulting phage are then used to transduce mammalian cells.

Example 13

Transduction and Amplication with a "Trojan Horse" AAV-Phage Vector

Figure 17:
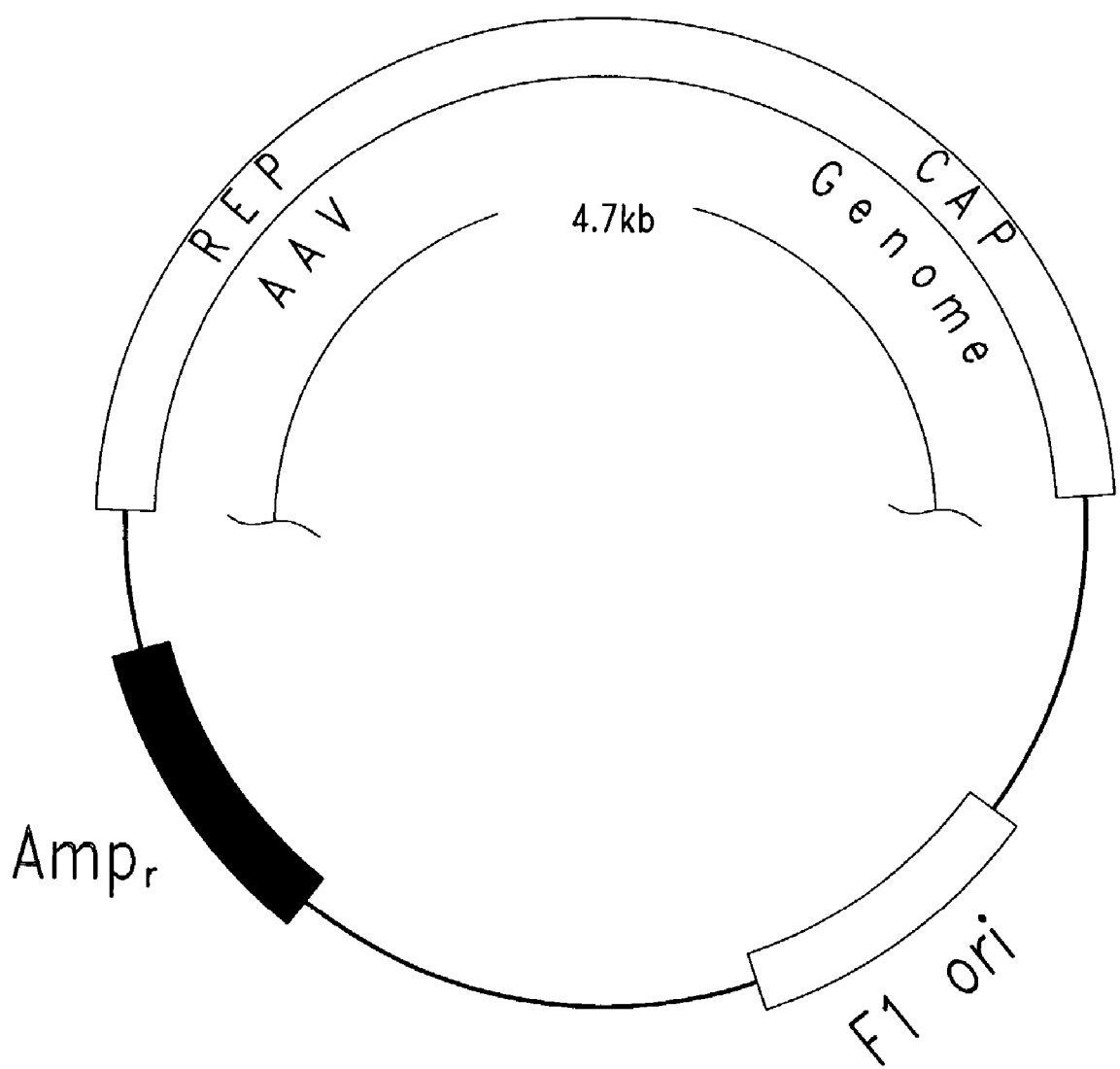
FIG. 17 is a vector map of an AAV-Phage helper vector carrying the rep and cap genes.

AAV-Phage hybrid vectors are prepared as described above, in Example 11. However, the transgene insert is constructed such that it comprises 4.7 kb or less in order to achieve packaging into an AAV particle. An AAV-phage hybrid helper phage is constructed which comprises a standard phagemid vector with an amp resistance gene, an F1 origin, a ligand-pIII/pVIII fusion construct, and the AAV genome, including the rep and cap genes, but no ITRs (FIG. 17). Such helper phage are analogous to a variety of helper plasmids that are known and used in AAV packaging systems and which can be readily modified such that they contain the ligand fusion construct and the F1 origin. The two phagemid vectors (the transgene containing vector and the helper vector) are prepared by using a helper phage to package the phagemids. The resulting phage are used to co-infect target cells via the ligand receptor (e.g., EGFR, FGFR, etc.). Following phage infection the cells are infected with adenovirus particles which rescue the AAV sequences allowing for AAV particle formation and infection of neighboring cells by the transgene containing AAV particles. Alternatively, the rep/cap functions are supplied in the helper virus (i.e., adenovirus, herpes simplex virus), engineered to supply rep and cap polypeptides.

It will be appreciated that, although specific embodiments of the invention have been described herein for purposes of illustration, various modifications may be made without departing from the spirit and scope of the invention. Accordingly, the invention is not limited except as by the appended claims.

We claim:

1. A method of gene delivery, comprising:
    contacting a mammalian cell with filamentous phage particles presenting a ligand on their surfaces, wherein a vector within the phage encodes a gene product under control of a promoter.

2. The method according to claim 1, wherein the ligand is an antibody.

3. The method according to claim 2, wherein the antibody is a single-chain antibody.

4. The method according to claim 2, wherein the antibody reacts with HER2/neu.

5. The method according to claim 1, wherein the ligand is genetically fused with a phage capsid protein.

6. The method according to claim 5, wherein the phage capsid protein is gene III.

7. The method according to claim 5, wherein the phage capsid protein is gene VIII.

8. The method according to claim 1, wherein the ligand is chemically conjugated to a phage capsid protein.

9. The method according to claim 1, wherein the phage genome is a phagemid.

10. The method according to claim 1, wherein the phage genome is a hybrid vector.

11. The method according to claim 1, wherein the phage particles display a nuclear localization sequence on the surface of the phages.

12. The method according to claim 1, wherein the vector encodes a gene product selected from the group consisting of protein, ribozyme, and antisense oligonucleotide.

* * * * *

UNITED STATES PATENT AND TRADEMARK OFFICE
CERTIFICATE OF CORRECTION

PATENT NO.       : 7,148,202 B2  
APPLICATION NO.  : 10/171407  
DATED            : December 12, 2006  
INVENTOR(S)      : Larocca et al.

Page 1 of 1

It is certified that error appears in the above-identified patent and that said Letters Patent is hereby corrected as shown below:

Title Page  
Item 63, Related U.S. Application Data, --This application is a CON of 09/258,584 filed 02/26/99, now Pat. No. 6,448,083, which is a-- should be inserted at line 1.

Signed and Sealed this

Fifth Day of August, 2008

JON W. DUDAS  
*Director of the United States Patent and Trademark Office*